United States Patent
Cho et al.

(10) Patent No.: US 11,316,114 B2
(45) Date of Patent: Apr. 26, 2022

(54) ORGANIC ELECTROLUMINESCENT COMPOUND AND ORGANIC ELECTROLUMINESCENT DEVICE COMPRISING THE SAME

(71) Applicants: DOW GLOBAL TECHNOLOGIES LLC, Midland, MI (US); ROHM AND HAAS ELECTRONIC MATERIALS KOREA LTD., Cheonan-si (KR)

(72) Inventors: Sang Hee Cho, Hwaseong-si (KR); Hong Yeop Na, Hwaseong-si (KR); Zhengming Tang, Shanghai (CN); Shaoguang Feng, Shanghai (CN); Doo-Hyeon Moon, Hwaseong-si (KR)

(73) Assignees: Rohm and Haas Erlectronic Materials Korea Ltd.; DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 16/077,765

(22) PCT Filed: Mar. 15, 2016

(86) PCT No.: PCT/CN2016/076340
§ 371 (c)(1),
(2) Date: Aug. 14, 2018

(87) PCT Pub. No.: WO2017/156698
PCT Pub. Date: Sep. 21, 2017

(65) Prior Publication Data
US 2019/0067593 A1 Feb. 28, 2019

(51) Int. Cl.
*H01L 51/00* (2006.01)
*H01L 51/50* (2006.01)
(Continued)

(52) U.S. Cl.
CPC ........ *H01L 51/0067* (2013.01); *C07D 403/10* (2013.01); *C07D 417/10* (2013.01);
(Continued)

(58) Field of Classification Search
CPC ............ H01L 51/0067; H01L 51/0071; H01L 51/0072; H01L 51/5012; H01L 51/5096;
(Continued)

(56) References Cited

U.S. PATENT DOCUMENTS 8,475,077 B2 7/2013 Howell
8,883,323 B2 11/2014 Kawamura et al.
(Continued)

FOREIGN PATENT DOCUMENTS

| CN | 104292218 A1 | 1/2015 |
|---|---|---|
| CN | 104835921 A1 | 8/2015 |

(Continued)

OTHER PUBLICATIONS

Son, et al., "Electroluminescence characteristics of a novel biphenyl derivative with benzoxazole for organic light-emitting diodes", Current Applied Physics, vol. 5, pp. 75-78 (2005).
(Continued)

*Primary Examiner* — Victor A Mandala
*Assistant Examiner* — Colleen E Snow
(74) *Attorney, Agent, or Firm* — G. Creston Campbell

(57) ABSTRACT

The present invention relates to an organic EL device comprising an electron buffer material, and a first electrode, a second electrode opposing the first electrode, a light-emitting layer disposed between the two electrodes, and an electron transport zone and an electron buffer layer disposed between the light-emitting layer and the second electrode. By using an electron buffer material according to the present invention, the organic EL device having low driving voltage, high luminous efficiency, and excellent lifespan can be provided.

10 Claims, 2 Drawing Sheets

(51) Int. Cl.
*C07D 417/10* (2006.01)
*C07D 403/10* (2006.01)
*C07D 413/04* (2006.01)

(52) U.S. Cl.
CPC ...... *H01L 51/0071* (2013.01); *H01L 51/0072* (2013.01); *H01L 51/5012* (2013.01); *H01L 51/5096* (2013.01); *C07D 413/04* (2013.01); H01L 51/5004 (2013.01); H01L 51/508 (2013.01); H01L 51/5056 (2013.01); H01L 51/5092 (2013.01)

(58) Field of Classification Search
CPC ............. H01L 51/5004; H01L 51/5056; H01L 51/508; H01L 51/5092
See application file for complete search history.

(56) References Cited

U.S. PATENT DOCUMENTS

| | | |
|---|---|---|
| 9,147,849 B2 | 9/2015 | Nam et al. |
| 9,246,108 B2 | 1/2016 | Ober et al. |
| 2004/0234809 A1 | 11/2004 | Chen et al. |
| 2006/0029828 A1 | 2/2006 | Kanno et al. |
| 2011/0196158 A1 | 8/2011 | Zheng |
| 2013/0172570 A1 | 7/2013 | Shi et al. |
| 2013/0274471 A1 | 10/2013 | In et al. |
| 2015/0034938 A1 | 2/2015 | Kang et al. |
| 2017/0005276 A1 | 1/2017 | Kim et al. |
| 2017/0117485 A1 | 4/2017 | Cho et al. |
| 2017/0162801 A1 | 6/2017 | Cho et al. |
| 2017/0207400 A1 | 7/2017 | Benelhadj et al. |
| 2017/0222159 A1 | 8/2017 | Yang et al. |
| 2019/0115536 A1* | 4/2019 | May .................... H01L 51/0056 |

FOREIGN PATENT DOCUMENTS

| | | |
|---|---|---|
| KR | 20120044523 A1 | 5/2012 |
| KR | 20140014956 A1 | 2/2014 |

OTHER PUBLICATIONS

Roh, et al., "Synthesis, Photophysical, and Electroluminescent Device Properties of Zn(ll)-Chelated Complexes Based an Functionalized Benzothiazole Derivatives", Adv. Funct. Mater., vol. 19, pp. 1663-1671 (2009).
Search Report for Chinese Patent Application No. 201680082957.2, Application dated Mar. 15, 2016.

* cited by examiner

ORGANIC ELECTROLUMINESCENT COMPOUND AND ORGANIC ELECTROLUMINESCENT DEVICE COMPRISING THE SAME

TECHNICAL FIELD

The present invention relates to an organic electroluminescent compound and an organic electroluminescent device comprising the same.

BACKGROUND ART

A low molecular green light-emitting organic electroluminescent (EL) device was developed by Tang, etc., of Eastman Kodak in 1987 by using TPD/ALq$_3$ bi-layer consisting of a light-emitting layer and an electron transport layer. Thereafter, the development of organic EL devices was rapidly effected and the devices were currently commercialized. Current organic EL devices mostly use phosphorescent materials with excellent luminous efficiency for panel manufacture. In the case of red and green light-emitting organic EL devices, commercialization of organic EL devices by using phosphorescent materials was succeeded. However, in the case of blue light-emitting organic EL devices, excessively formed excitons were dissipated to decrease roll-off at a high current thereby declining characteristics of devices, lifespan of blue phosphorescent materials themselves has a problem with long-term stability, and a sharp decline of color purity occurred over time, and thus were the obstacles to serve a full color display.

Currently used fluorescent light-emitting materials also have various problems. The first problem is that if the materials are exposed at high temperature in the process of panel production, current property of the devices changes, and thus light-emitting luminance may be accordingly changed. Furthermore, in view of structural feature, interface property between a light-emitting layer and an electron injection layer is declined, and thus luminance of the devices may be decreased. Also, fluorescent light-emitting materials have lower efficiency characteristics than phosphorescent light-emitting materials. Thus, in order to improve efficiency, specific fluorescent light-emitting materials such as the combination of an anthracene-based host and a pyrene-based dopant were used. However, since the materials have a high hole-trapping property, a light-emitting region in a light-emitting layer is leaned to a hole-transport layer, and thus light-emitting tends to happen at the interface of the two layers. The light-emitting at an interface has problems with decrease of lifespan of the devices and unsatisfactory efficiency.

The above problems of fluorescent light-emitting materials are difficult to solve by mere improvement of materials themselves. Thus, in order to solve the problems, there has recently been an attempt to change electron-transport property by improvement of electron-transport materials, or to develop structure of optimized devices.

Korean Patent Application Laying-Open No. 10-2012-0092550 discloses an organic EL device comprising a blocking layer disposed between an electron injection layer and a light-emitting layer, wherein the blocking layer includes aromatic heterocyclic derivatives comprising an azine ring. However, the literature does not recite an organic EL device using the compounds comprising an oxazole or thiazole skeleton in an electron buffer layer.

Japanese Patent No. 4947909 contains a blue fluorescent light-emitting device comprising an electron buffer layer. The device had the insertion of an electron buffer layer, thereby efficiently injecting electrons into a light-emitting layer compared with Alq$_3$ and controlling movement of electrons. This feature inhibited decrease of driving voltage and deterioration of a light-emitting interface, and thus lifespan of the device was improved. However, materials of an electron buffer layer are limited to Alq$_3$ derivatives, restriction of electrons is the purpose, and types of materials are not various, and thus analysis for effective luminous efficiency and lifespan improvement is limited.

Korean Patent Application Laying-Open No. 10-2014-0086861 discloses an organic EL device having the insertion of an electron transport layer including quinoline-benzoxazole derivatives. However, the electron transport layer only plays a role as an electron transport layer co-deposited with lithium quinolate. Thus, the literature has limitation in optimizing devices comprising an electron buffer layer in view of control of electron current property by using pure characteristics of related compounds.

DISCLOSURE OF THE INVENTION

Problems to be Solved

The object of the present invention is to provide an organic EL device having low driving voltage, high luminous efficiency, and excellent lifespan.

Solution to Problems

The above objective can be achieved by an electron buffer material comprising the compound represented by the following formula 1:

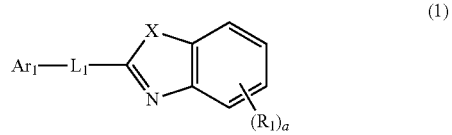

wherein

Ar$_1$ represents a substituted or unsubstituted (C6-C30)aryl group, or a substituted or unsubstituted 5- to 30-membered heteroaryl group;

L$_1$ represents a single bond, a substituted or unsubstituted (C6-C30)arylene group, or a substituted or unsubstituted 3- to 30-membered heteroarylene group;

X represents O, S, or NR$_2$;

R$_1$ and R$_2$ each independently represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted 3- to 7-membered heterocycloalkyl group, a substituted or unsubstituted (C6-C30)aryl group, a substituted or unsubstituted 3- to 30-membered heteroaryl group, —NR$_3$R$_4$, or —SiR$_5$R$_6$R$_7$; or are linked to an adjacent substituent(s) to form a substituted or unsubstituted mono- or polycyclic (C3-C30) alicyclic or aromatic ring whose carbon atom(s) may be replaced with at least one hetero atom selected from nitrogen, oxygen, and sulfur;

R$_3$ to R$_7$ each independently represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted 3- to 7-membered heterocycloalkyl group, a substituted or unsubstituted (C6-C30)aryl group, or a substituted or unsubstituted 3- to 30-membered heteroaryl group;

a represents an integer of 1 to 4; where a is an integer of 2 or more, each $R_1$ is the same or different; and the heteroaryl(ene) and heterocycloalkyl groups each independently contain at least one hetero atom selected from B, N, O, S, P(=O), Si, and P.

Effects of the Invention

The organic EL device according to the present invention comprises an electron buffer layer, thereby controlling injection of electrons and improving characteristics of interface disposed between a light-emitting layer and an electron injection layer. Thus, the present invention can provide an organic EL device with excellent luminous efficiency. Primarily, when an electron buffer layer is present between a light-emitting layer and an electron transport layer, electron current is inhibited, and thus driving voltage may be increased and efficiency may be decreased. However, when the light-emitting compounds according to the present invention are used, an organic EL device with low driving voltage, excellent luminous efficiency such as current efficiency and power efficiency, excellent lifespan, and implementation possibility of high purity color may be provided by rapid election injection characteristics and improvement of interface property.

EMBODIMENTS OF THE INVENTION

Figure 1:
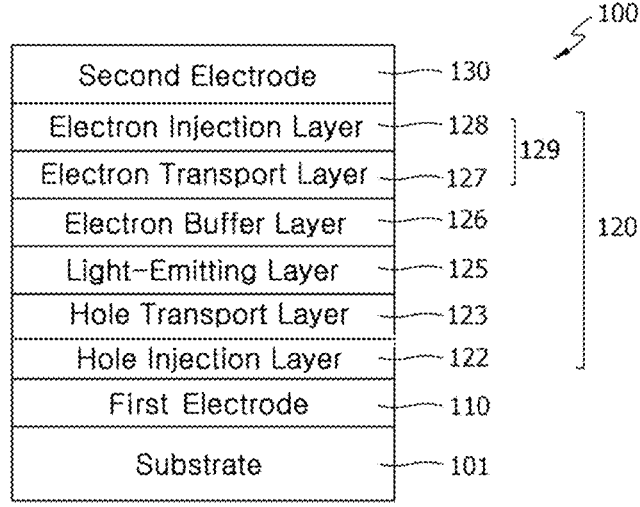
FIG. 1 shows one embodiment of the structure of the organic EL device comprising an electron buffer layer according to the present invention.
Figure 2:
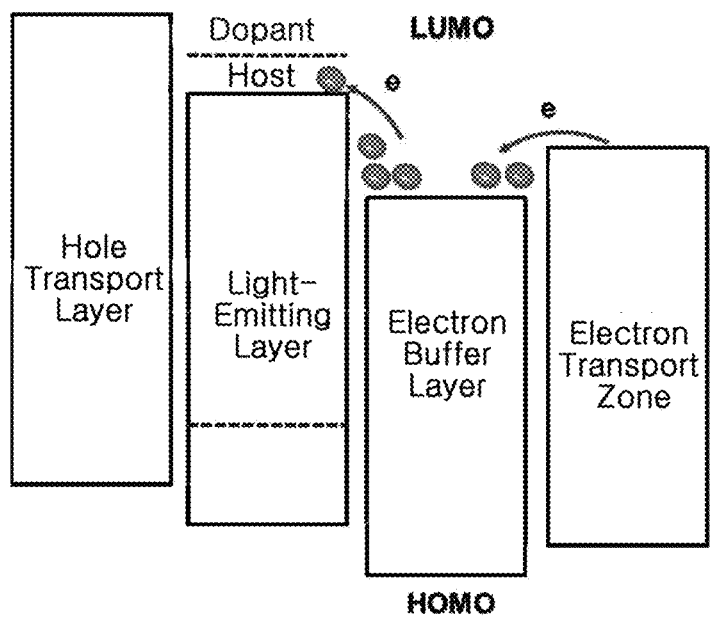
FIG. 2 shows an energy diagram of the organic EL device comprising an electron buffer layer according to the present invention.

Hereinafter, the present invention will be described in detail. However, the following description is intended to explain the invention, and is not meant in any way to restrict the scope of the invention.

The compound of formula 1 is represented by one of the following formulae 2 to 5:

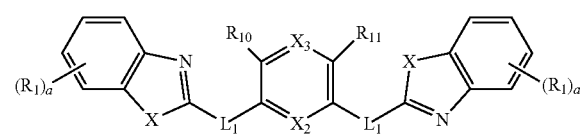

(2)

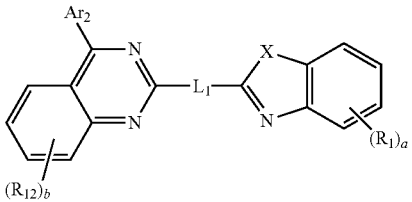

(3)

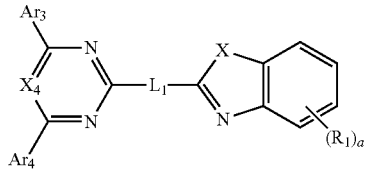

(4)

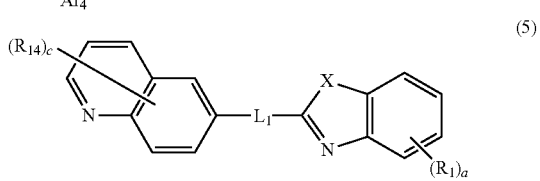

(5)

wherein
$L_1$, X, $R_1$, and a are as defined in formula 1;
$X_2$ represents N or $CR_8$;
$X_3$ represents N or $CR_9$;
with the proviso that when $X_2$ represents N, $X_3$ represents $CR_9$, and if $X_2$ represents $CR_8$, $X_3$ represents N;
$R_8$ to $R_{11}$ each independently have the same meaning as the definition of $R_3$ of formula 1;
$Ar_2$ has the same meaning as the definition of $Ar_1$ of formula 1;
$R_{12}$ has the same meaning as the definition of $R_1$ of formula 1;
$Ar_3$ and $Ar_4$ have the same meaning as the definition of $Ar_1$ of formula 1;
$X_4$ represents N or $CR_{13}$;
$R_{13}$ has the same meaning as the definition of $R_1$ of formula 1;
$R_{14}$ has the same meaning as the definition of $R_1$ of formula 1; and
b and c have respectively the same meaning as the definition of a of formula 1.

Herein, "(C1-C30)alkyl" is meant to be a linear or branched alkyl having 1 to 30 carbon atoms, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C1-C30)alkoxy" is meant to be a linear or branched alkoxy having 1 to 30 carbon atoms, in which the number of carbon atoms is preferably 1 to 20, more preferably 1 to 10, and includes methoxy, ethoxy, propoxy, isopropoxy, 1-ethylpropoxy, etc. "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is a cycloalkyl having at least one heteroatom selected from B, N, O, S, P(=O), Si, and P, preferably O, S, and N, and 3 to 7 ring backbone atoms, and includes pyrrolidine, thiolan, tetrahydropyran, etc. "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc. "3- to 30-membered heteroaryl(ene)" is an aryl group having at least one, preferably 1 to 4 heteroatoms selected from the group consisting of B, N, O, S, P(=O), Si, and P, and 3 to 30 ring backbone atoms; is a monocyclic ring, or a fused ring condensed with at least one benzene ring; has preferably 3 to 20, more preferably 3 to 15 ring backbone atoms; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or group, i.e. a substituent. Substituents of the substituted alkyl group, the substituted aryl(ene) group, the substituted heteroaryl(ene) group, the substituted cycloalkyl group, the substituted cycloalkenyl group, the substituted heterocycloalkyl group, or the substituted mono- or polycyclic (C3-C30) alicyclic or aromatic ring in formula 1 are each independently at least one selected from the group consisting of deuterium; a halogen; a cyano group; a carboxyl group; a nitro group; a hydroxyl group; a (C1-C30)alkyl group; a halo(C1-C30) alkyl group; a (C2-C30)alkenyl group; a (C2-C30)alkynyl group; a (C1-C30)alkoxy group; a (C1-C30)alkylthio group; a (C3-C30)cycloalkyl group; a (C3-C30)cycloalkenyl group; a 3- to 7-membered heterocycloalkyl group; a (C6-C30)aryloxy group; a (C6-C30)arylthio group; a 5- to 30-membered heteroaryl group which is unsubstituted or substituted with a (C6-C30)aryl group; a (C6-C30)aryl group which is unsubstituted or substituted with a 5- to 30-membered heteroaryl group; a tri(C1-C30)alkylsilyl group; a tri(C6-C30)arylsilyl group; a di(C1-C30)alkyl(C6-C30)arylsilyl group; a (C1-C30)alkyldi(C6-C30)arylsilyl group; an amino group; a mono- or di(C1-C30)alkylamino group; a mono- or di(C6-C30)arylamino group; a (C1-C30) alkyl(C6-C30)arylamino group; a (C1-C30)alkylcarbonyl group; a (C1-C30)alkoxycarbonyl group; a (C6-C30)arylcarbonyl group; a di(C6-C30)arylboronyl group; a di(C1-C30)alkylboronyl group; a (C1-C30)alkyl(C6-C30)arylboronyl group; a (C6-C30)aryl(C1-C30)alkyl group; and a (C1-C30)alkyl(C6-C30)aryl group.

In a preferable embodiment of the present invention, the electron buffer material wherein X in formula 1 is $NR_2$ or X in formula 1 is O or S is provided. In formula 1, compounds wherein X is O or S have an effect of improving device efficiency. In formula 1, compounds wherein X is N have an effect of contributing to increase device lifespan.

The organic EL compound of formula 1 may be selected from the group consisting of the following compounds, but is not limited thereto:

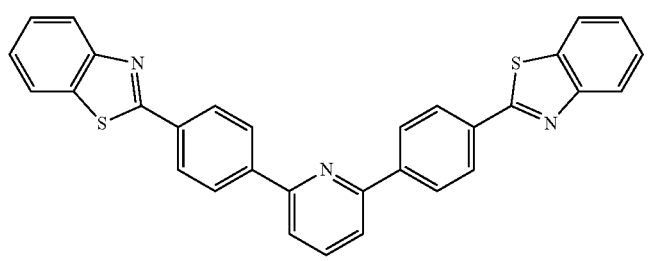

B-1

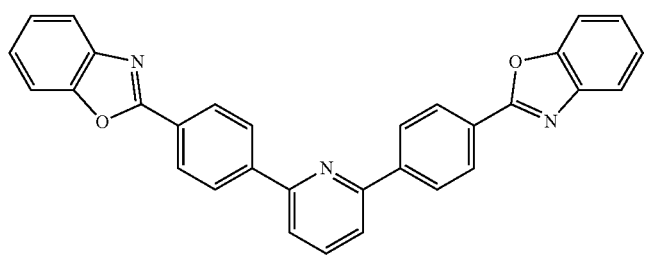

B-2

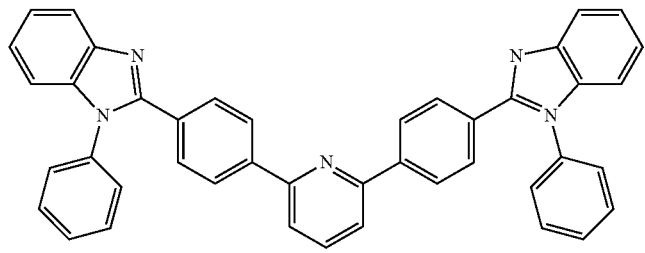
B-3
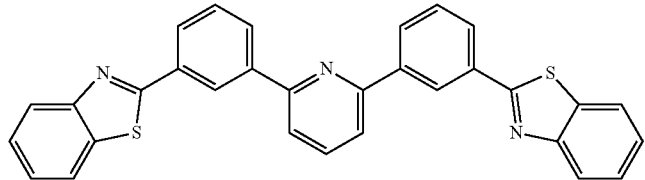
B-4
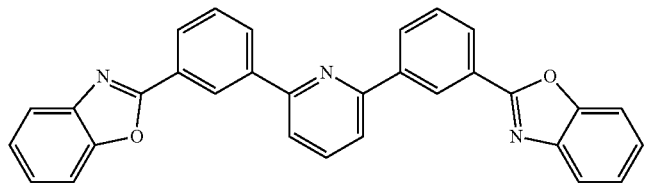
B-5
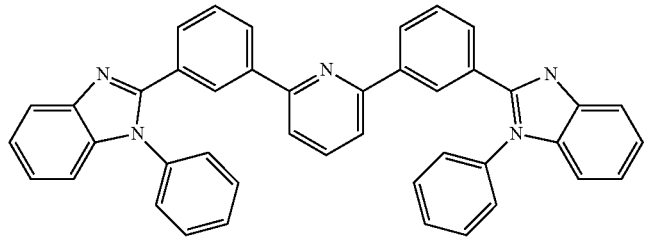
B-6
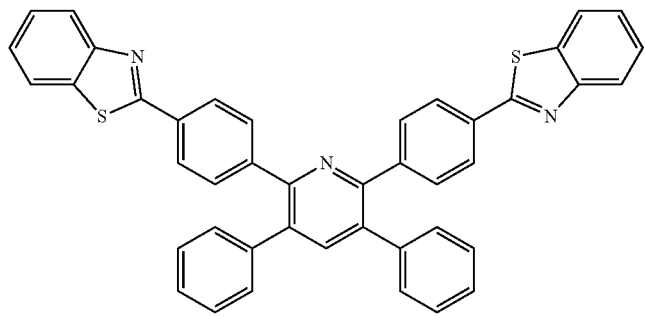
B-7
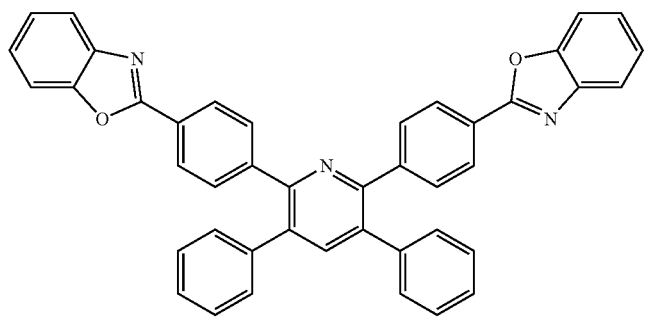
B-8

B-9
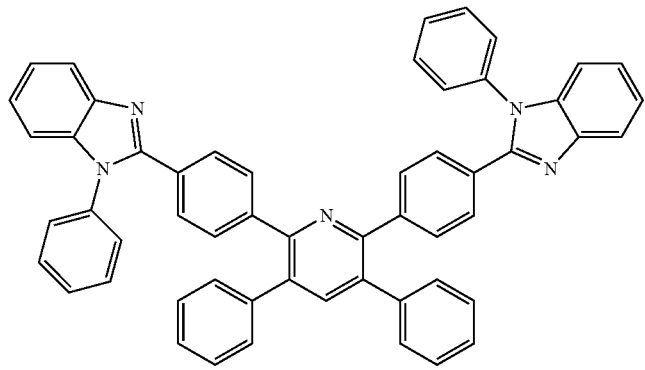
B-10
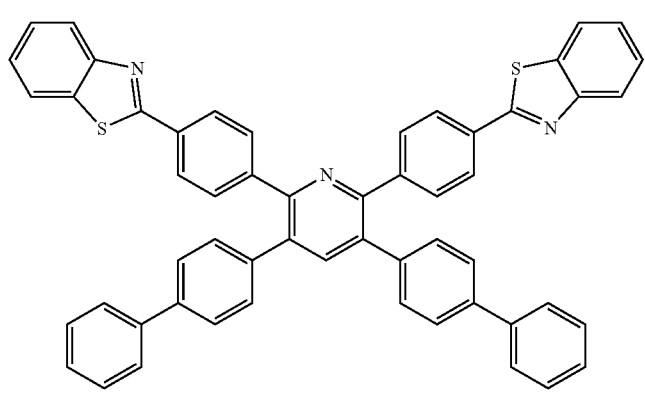
B-11
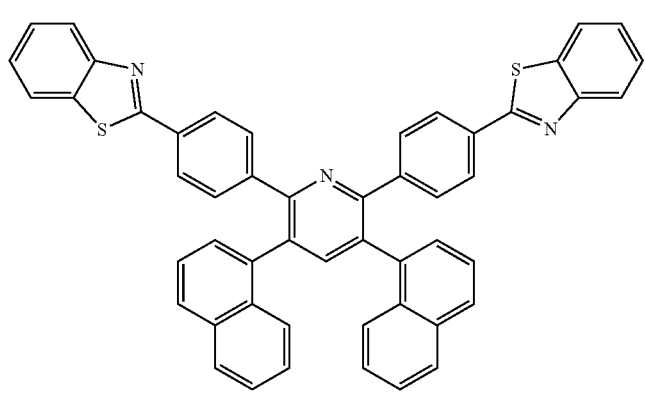
B-12
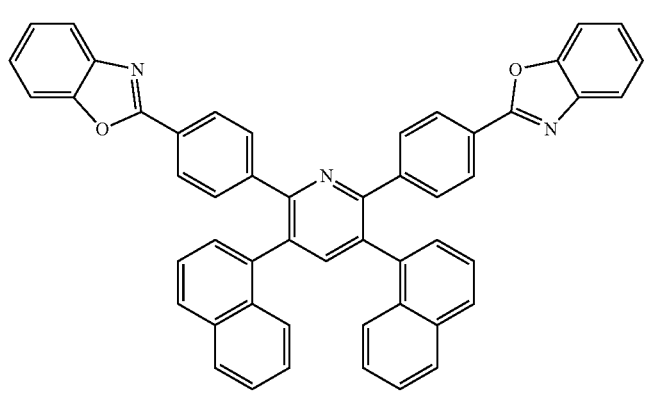

-continued
B-13
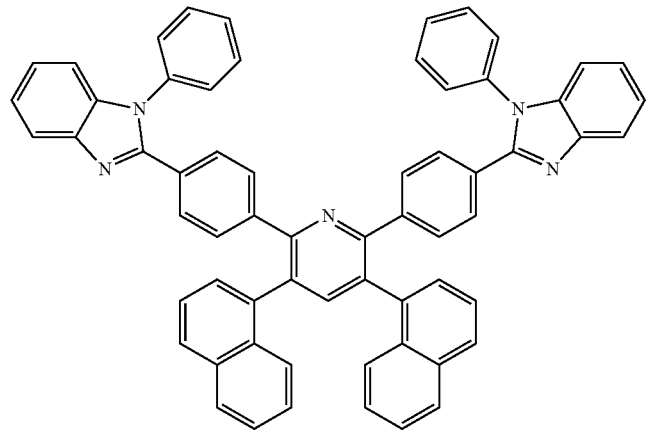
B-14
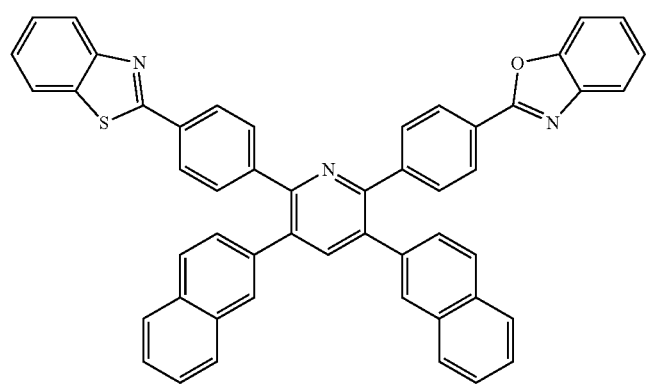
B-15
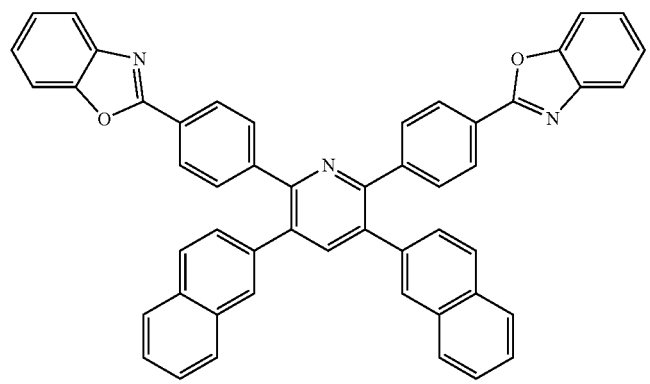
B-16
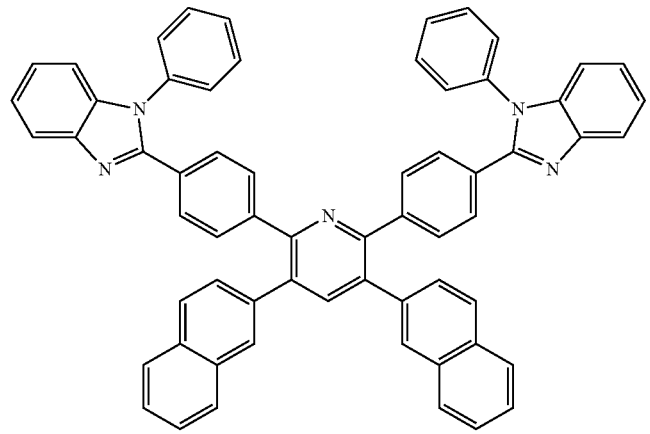

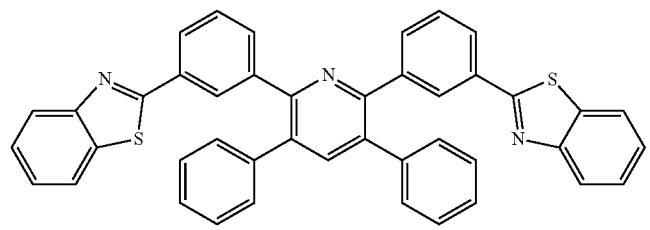
B-17
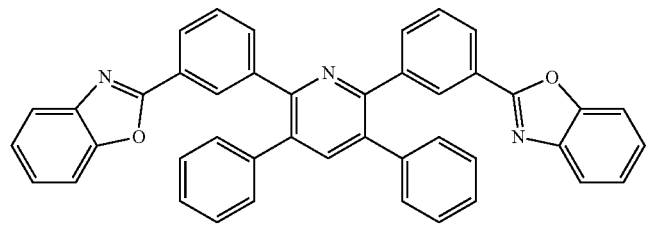
B-18
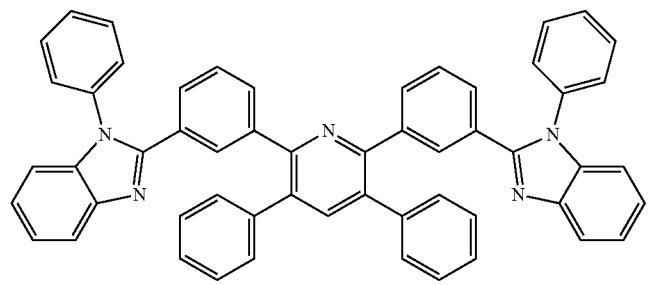
B-19
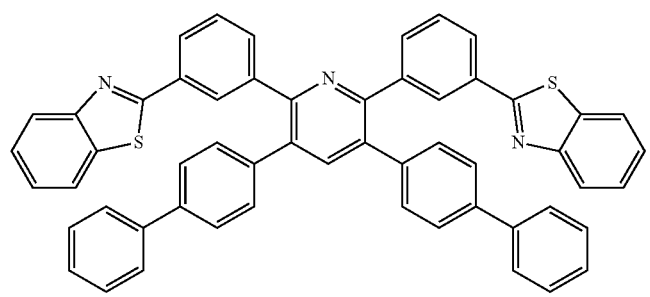
B-20
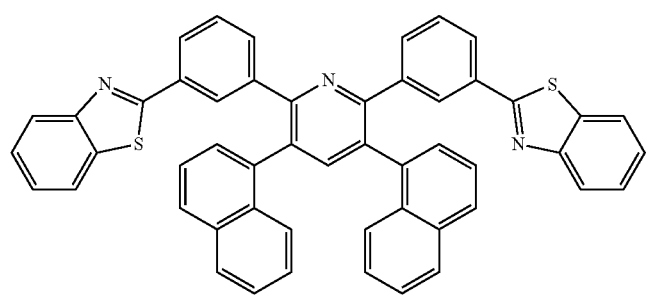
B-21
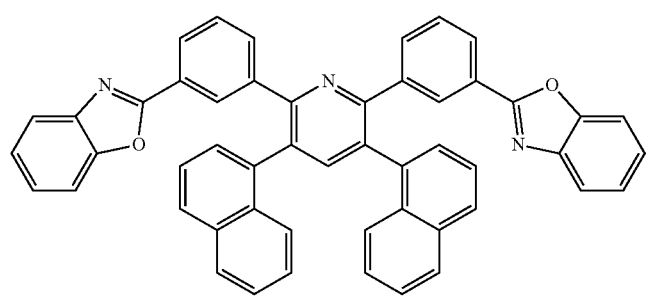
B-22

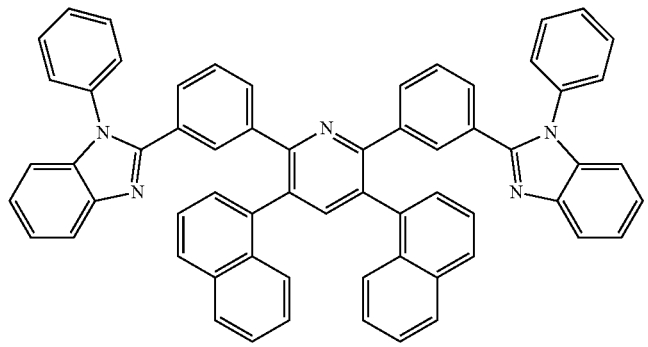
B-23
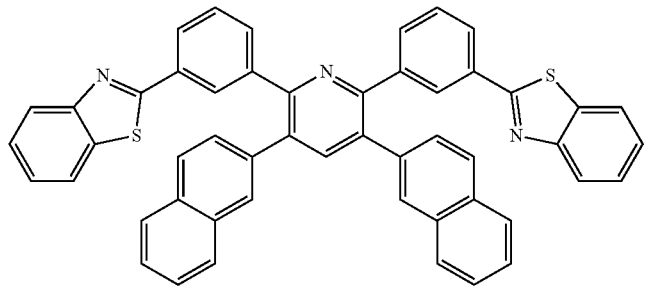
B-24
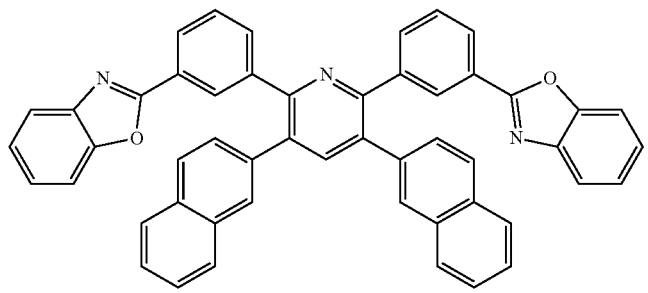
B-25
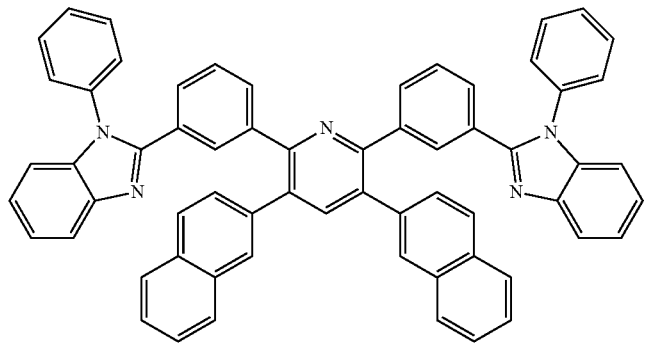
B-26
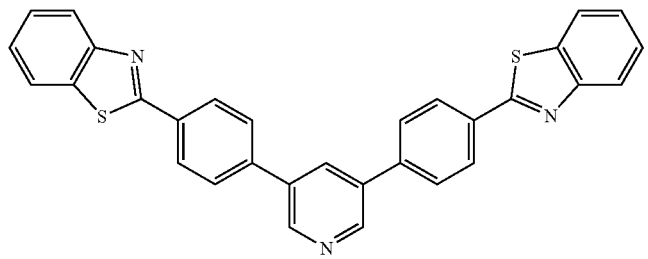
B-27

-continued
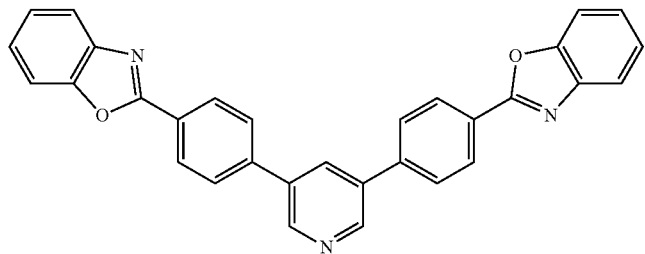
B-28
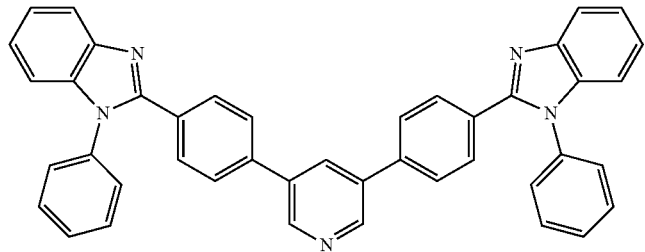
B-29
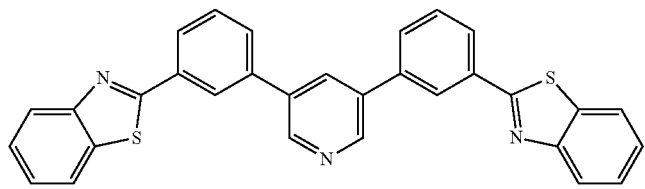
B-30
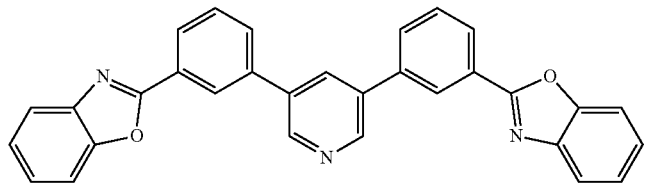
B-31
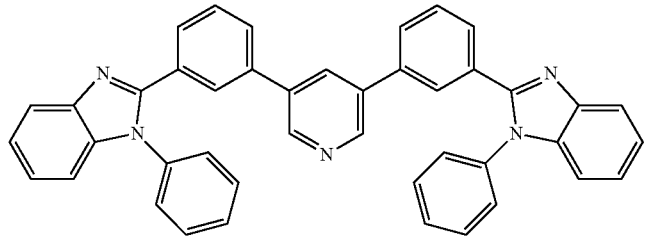
B-32
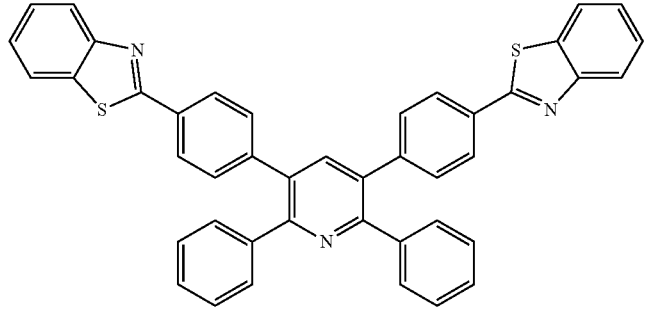
B-33

-continued
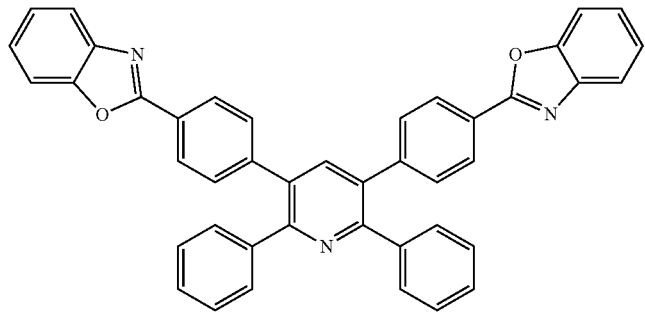
B-34
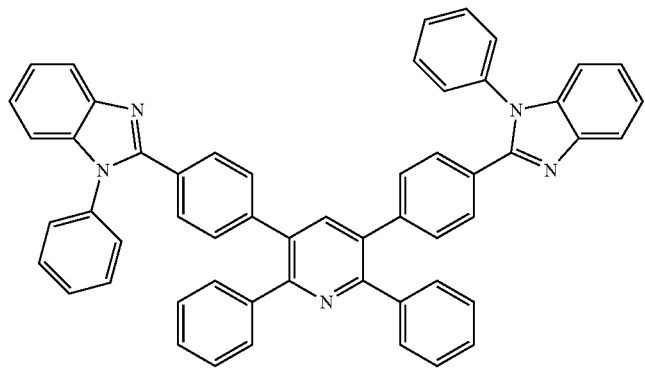
B-35
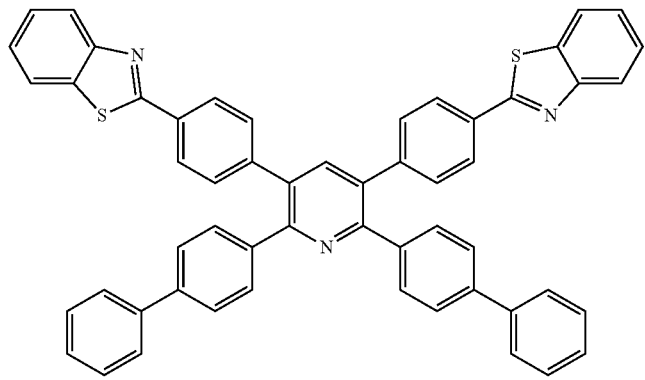
B-36
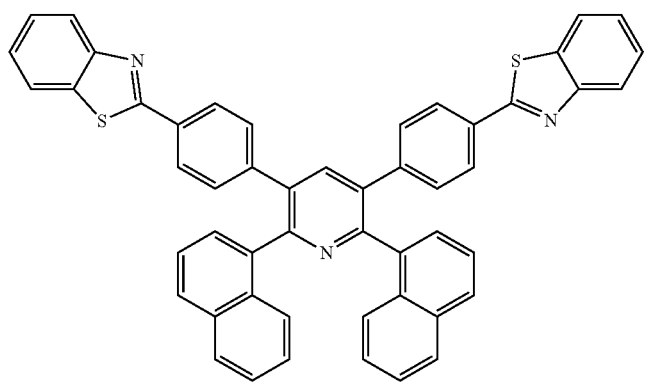
B-37

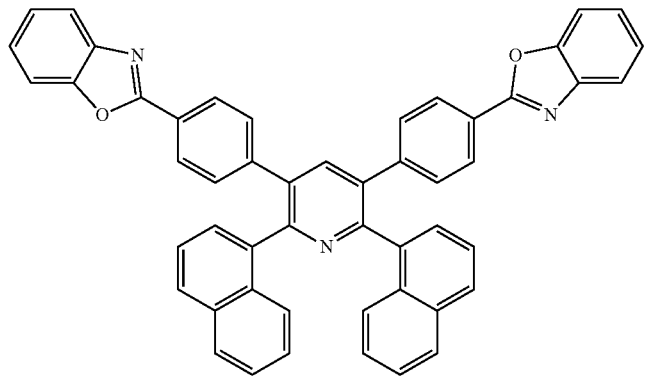
B-38
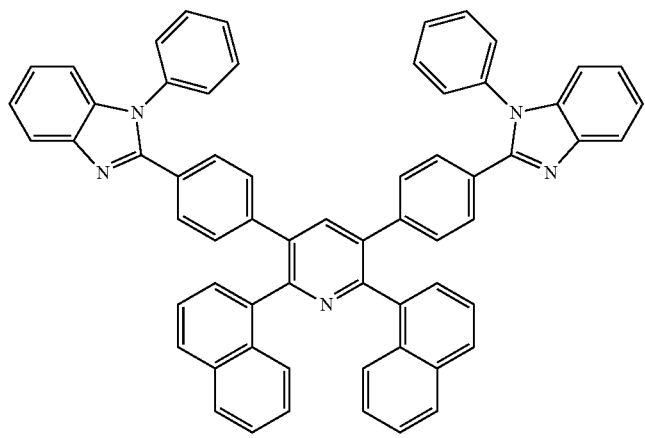
B-39
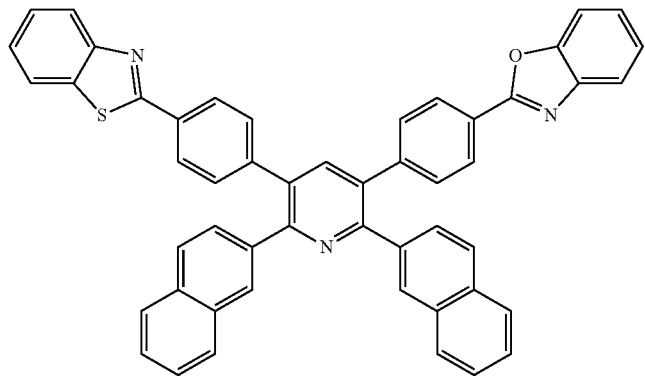
B-40
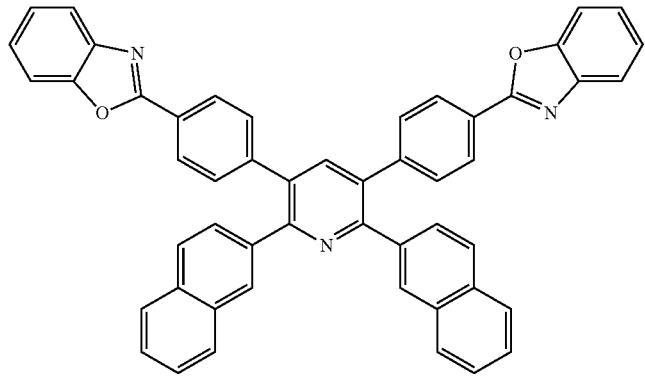
B-41

-continued
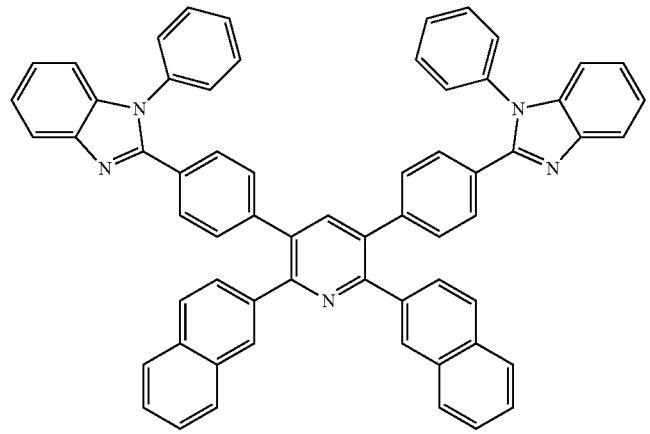
B-42
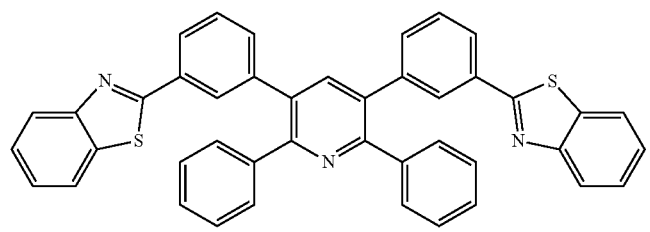
B-43
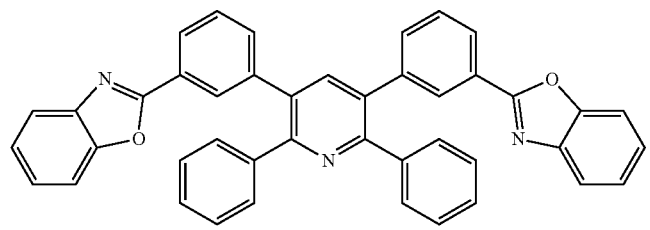
B-44
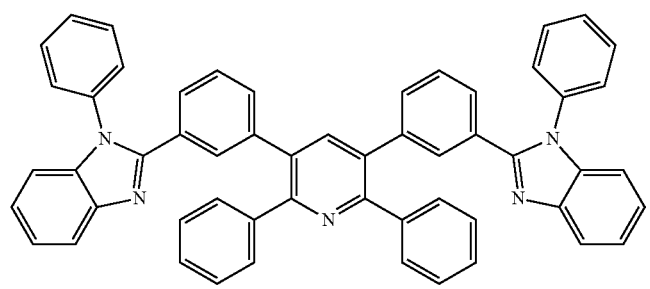
B-45
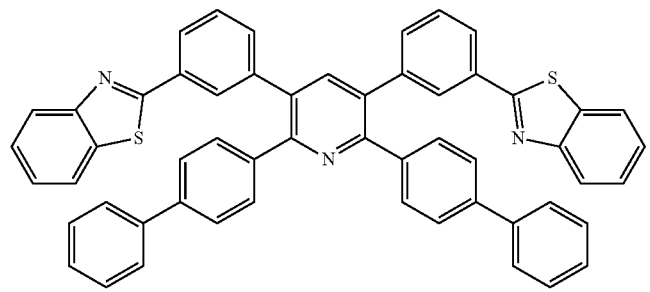
B-46

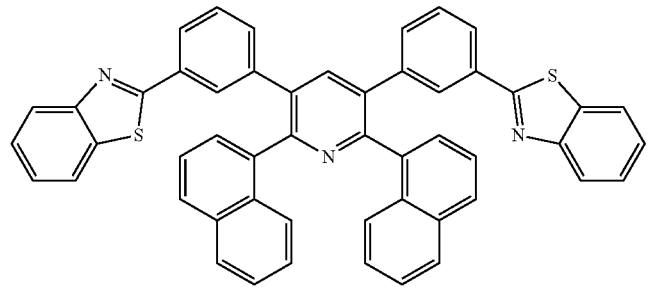
B-47
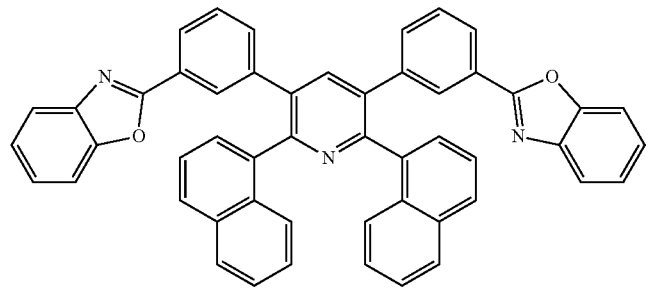
B-48
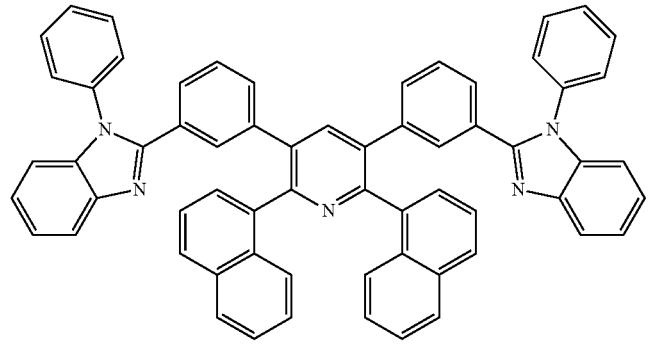
B-49
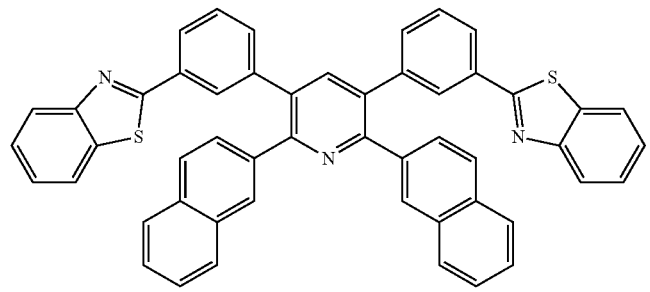
B-50
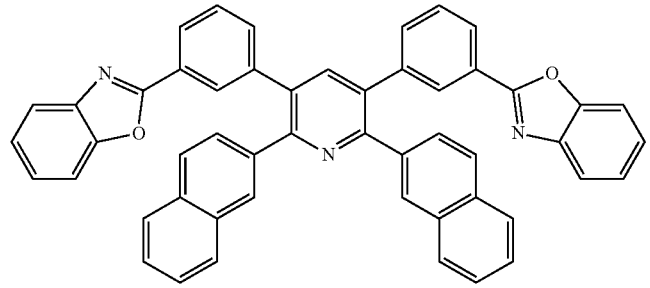
B-51

-continued
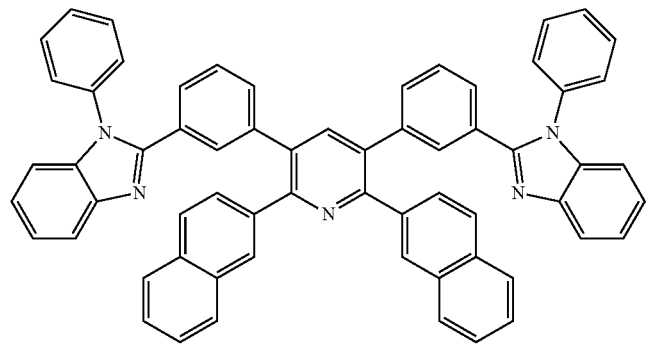
B-52
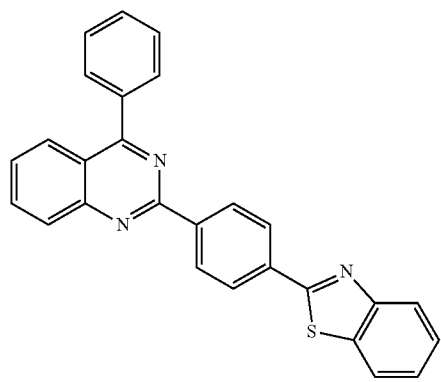
B-53
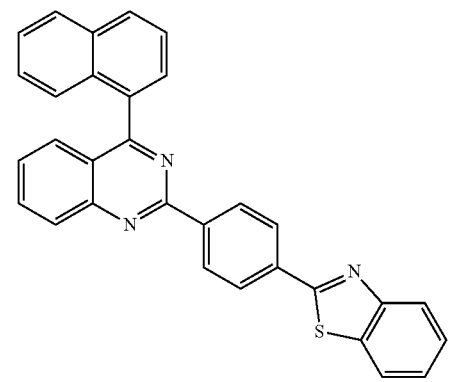
B-54
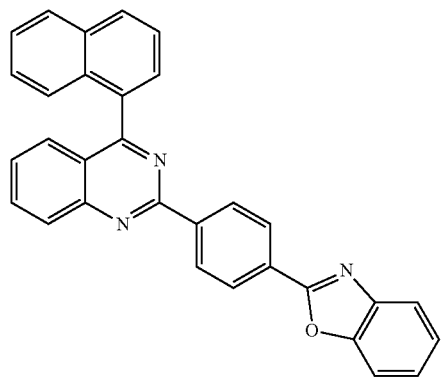
B-55
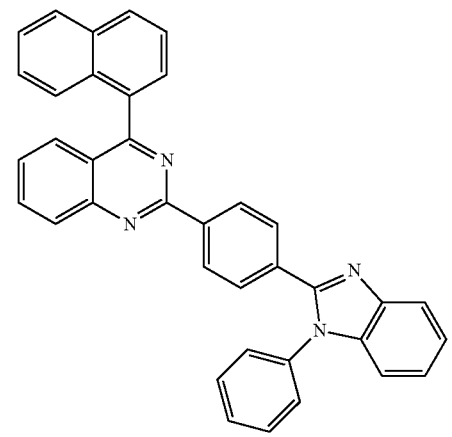
B-56
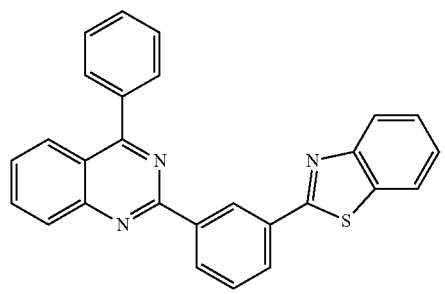
B-57
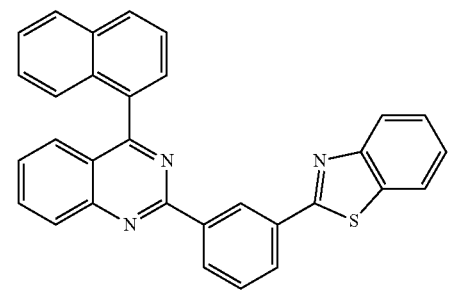
B-58

B-59
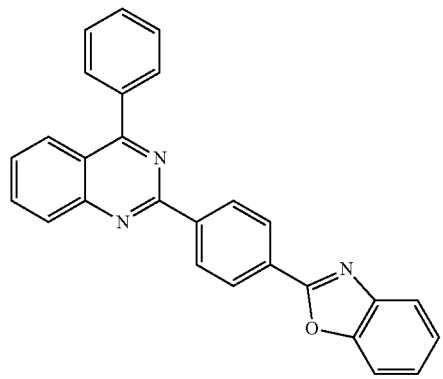
B-60
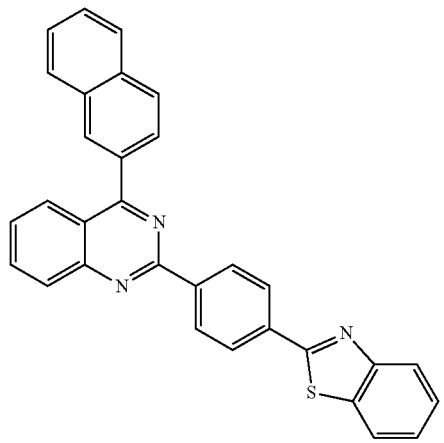
B-61
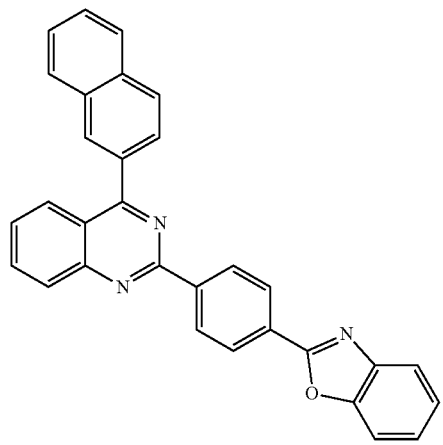
B-62
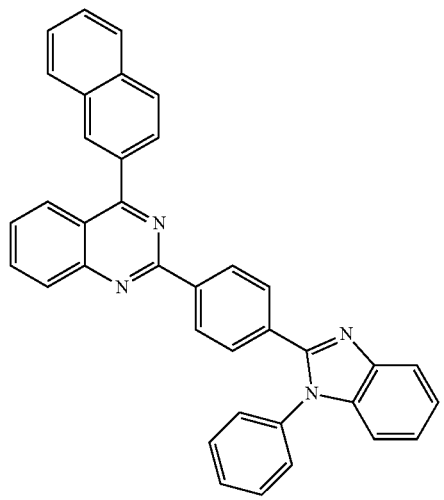
B-63
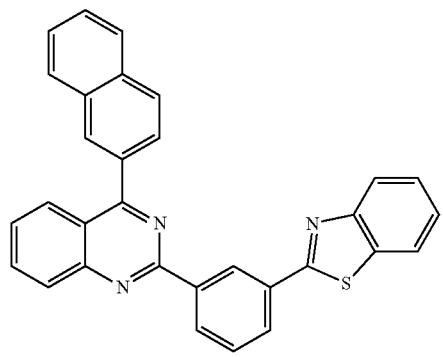
B-64
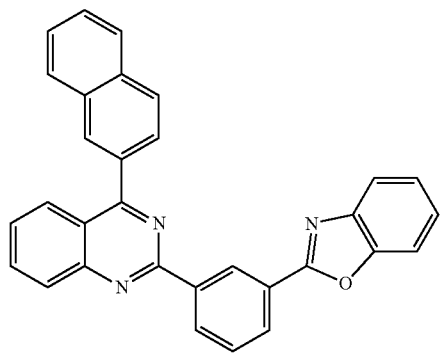

B-65
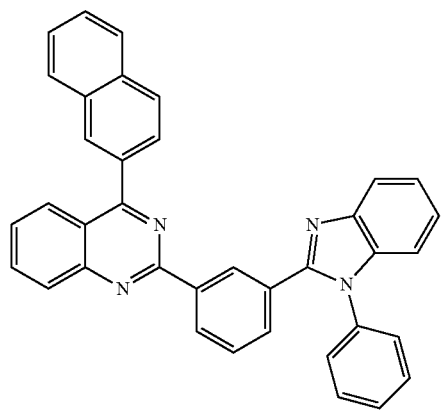
B-66
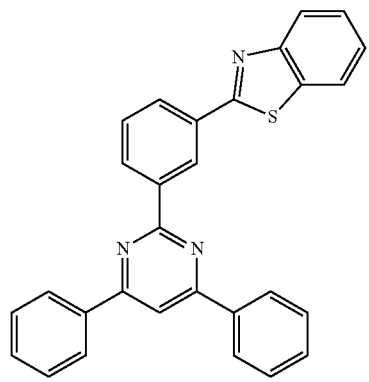
B-67
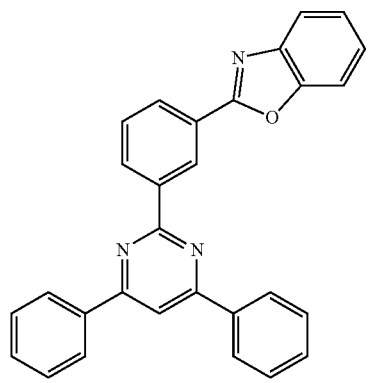
B-68
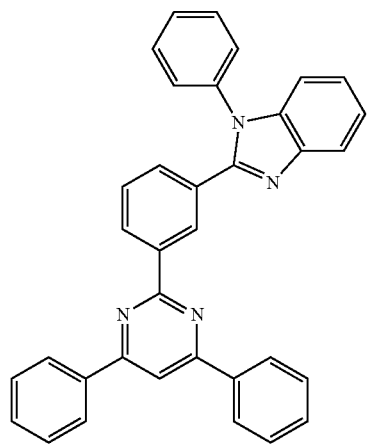
B-69
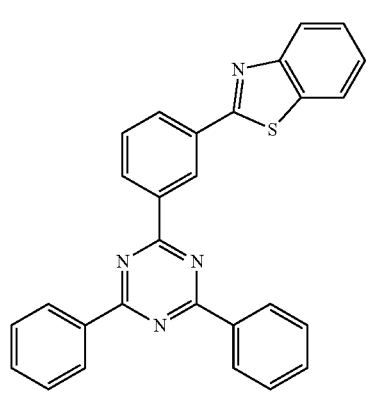
B-70
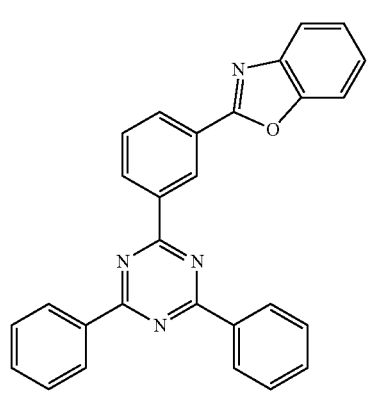

-continued
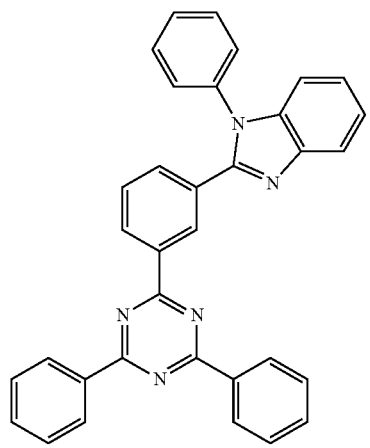
B-71
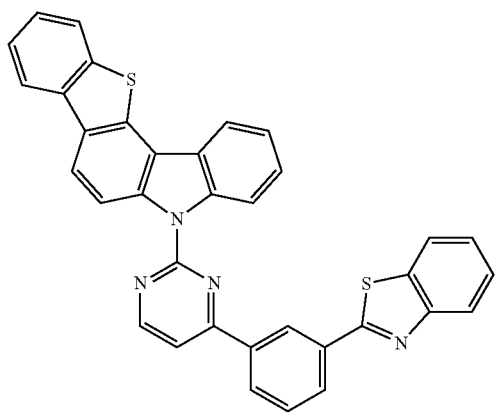 [SMILES: c1cc(-c2ccnc(-n3c4ccccc4c4c5sc6ccccc6c5ccc43)n2)cc(-c2nc3ccccc3s2)c1]
B-72
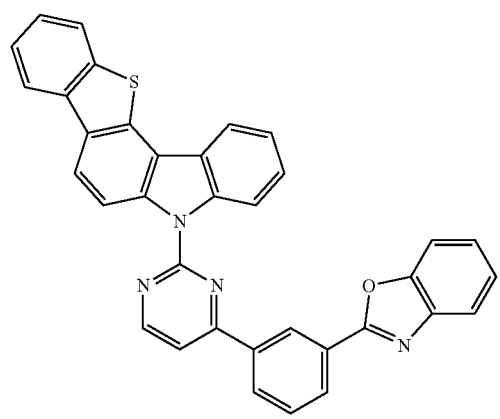
B-73
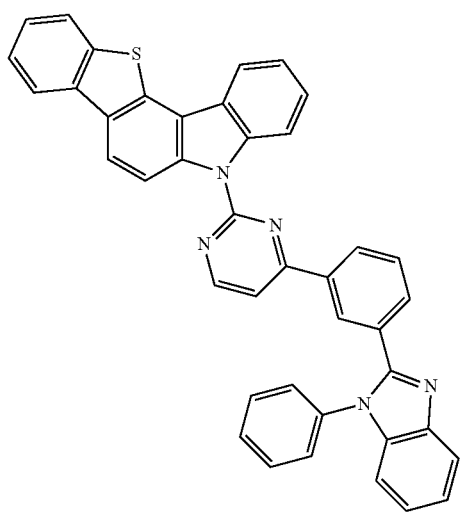
B-74
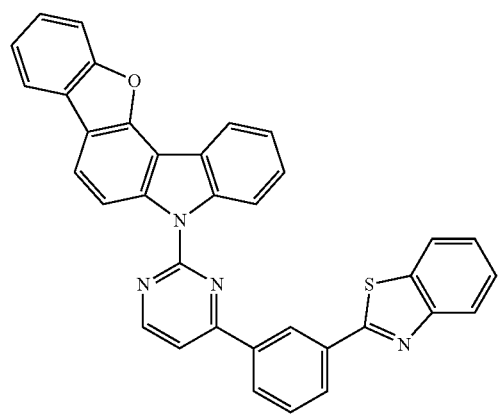
B-75
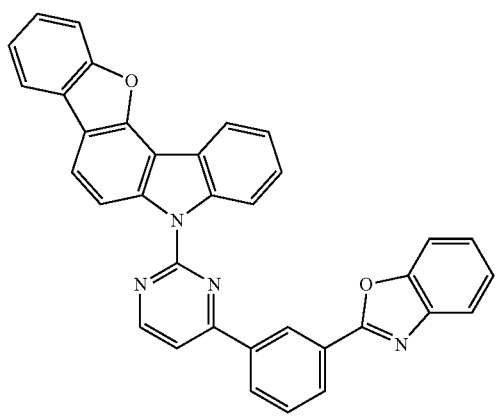
B-76

-continued
B-77
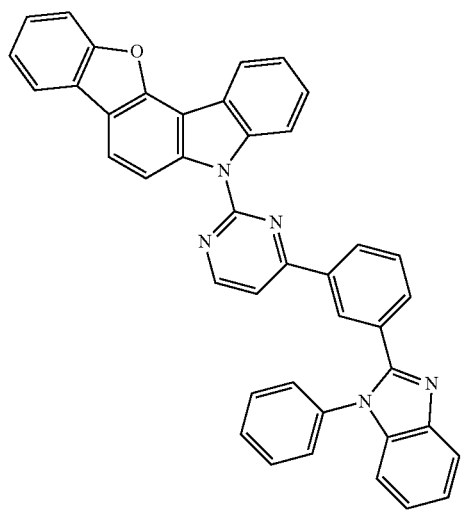
B-78
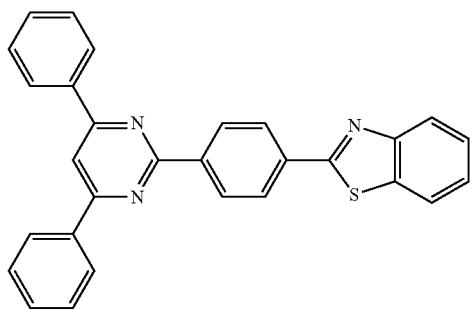
B-79
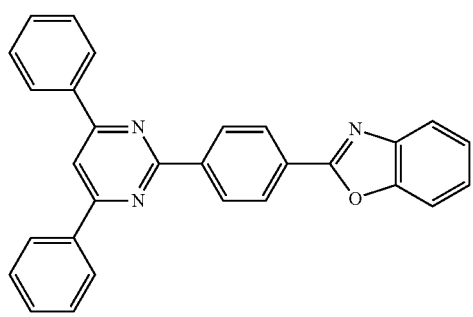
B-80
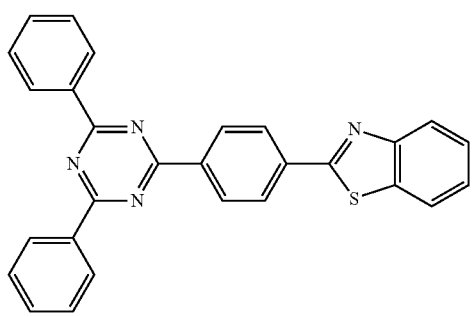
B-81
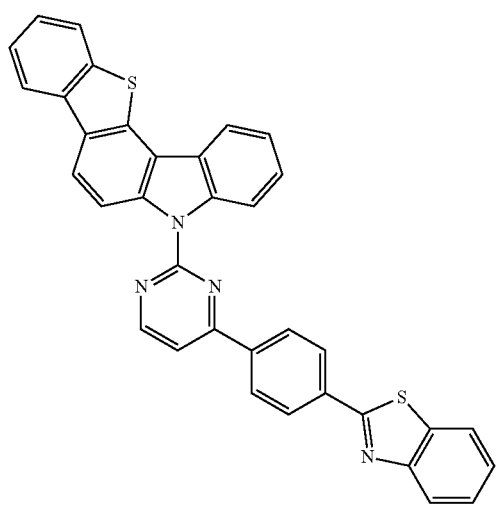
B-82
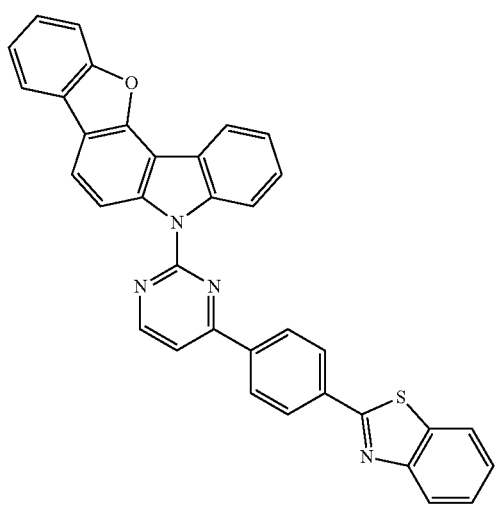

-continued
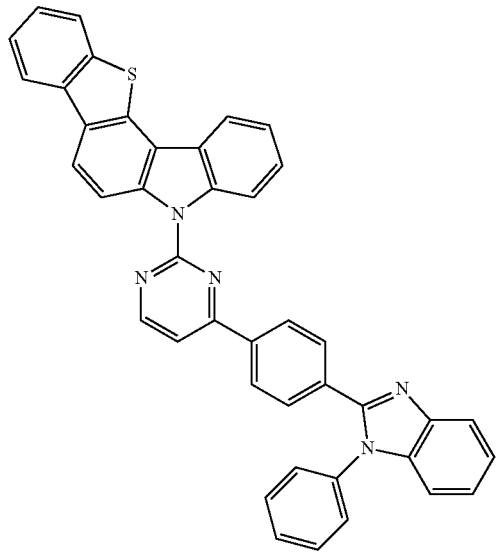
B-83
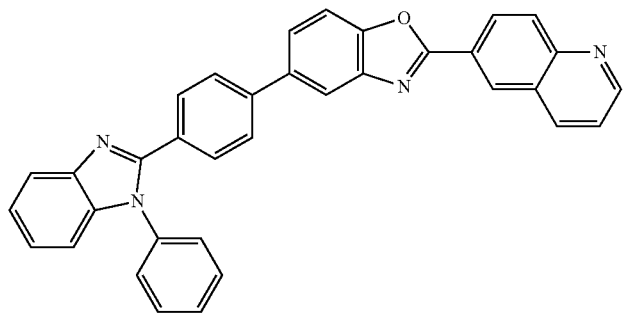
B-84
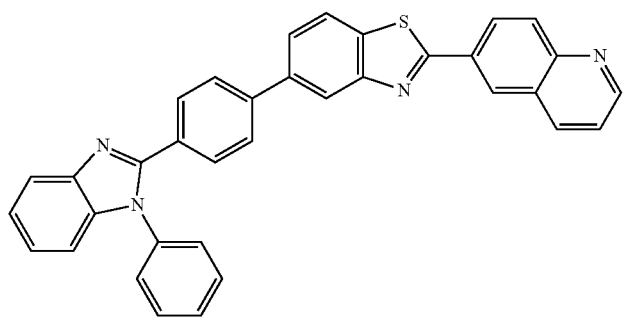
B-85
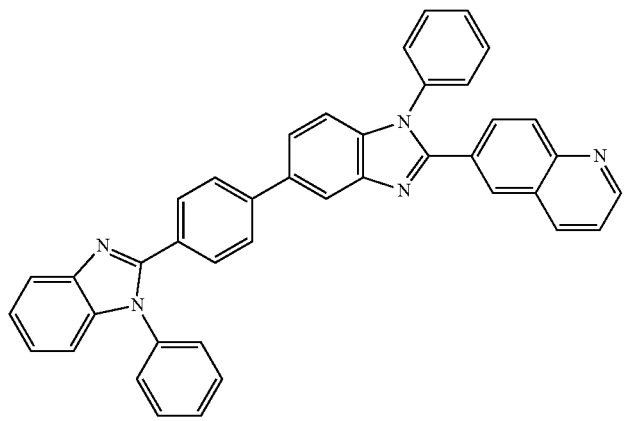
B-86

-continued
B-87
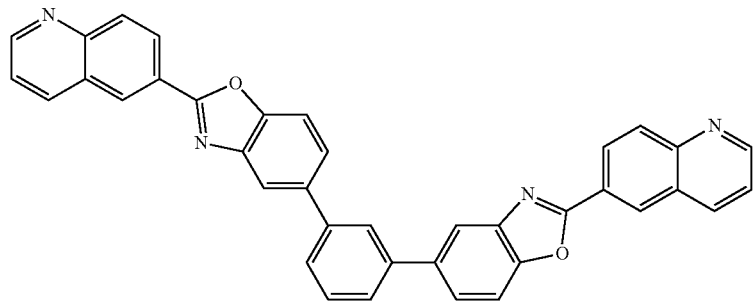
B-88
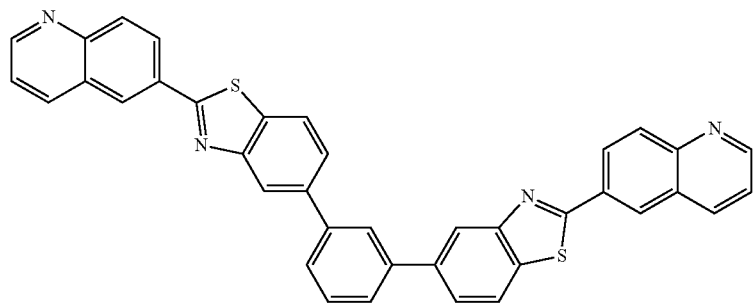
B-89
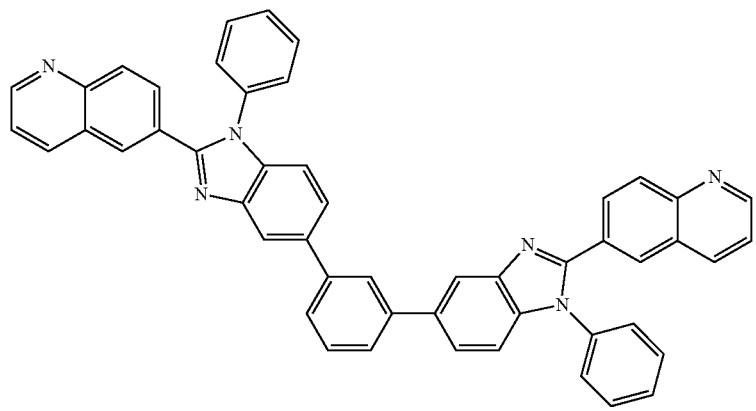
B-90
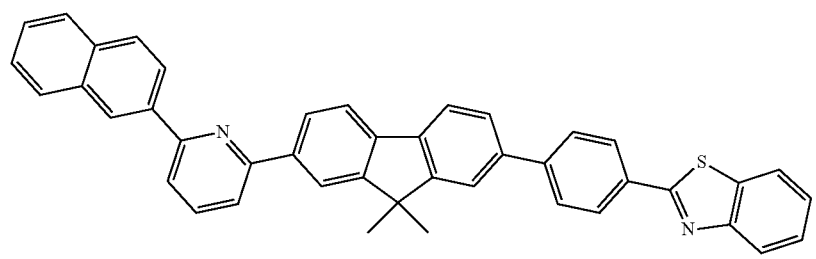
B-91
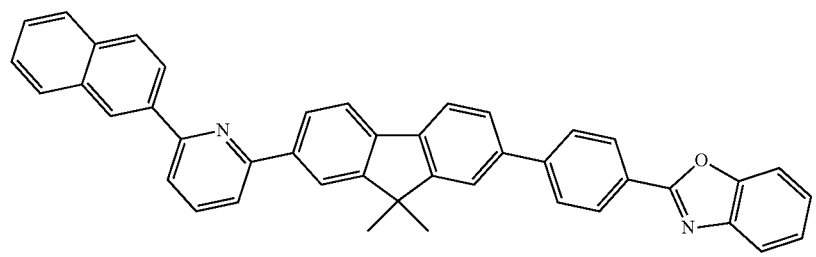

-continued
B-92
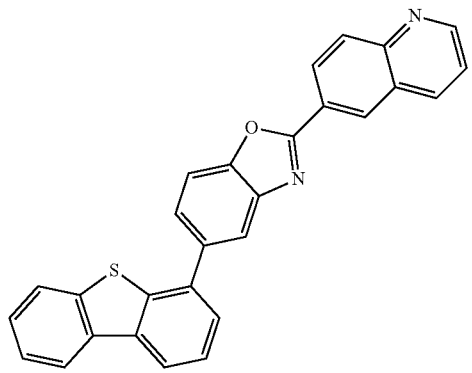
B-93
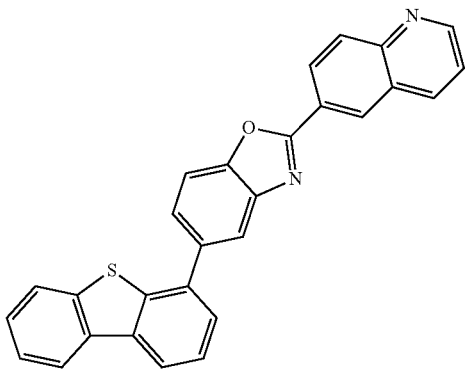
B-94
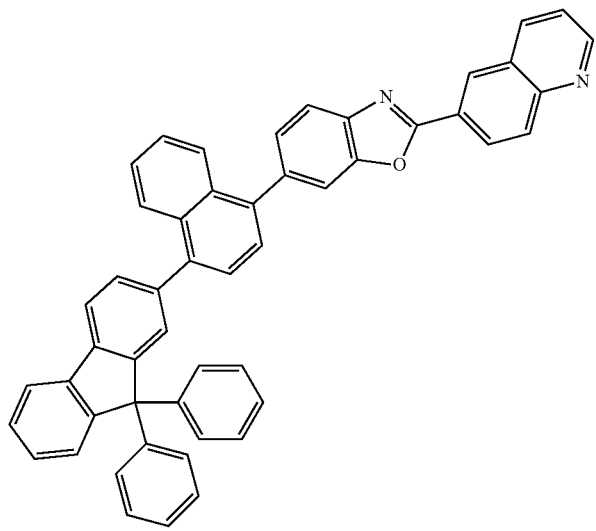
B-95
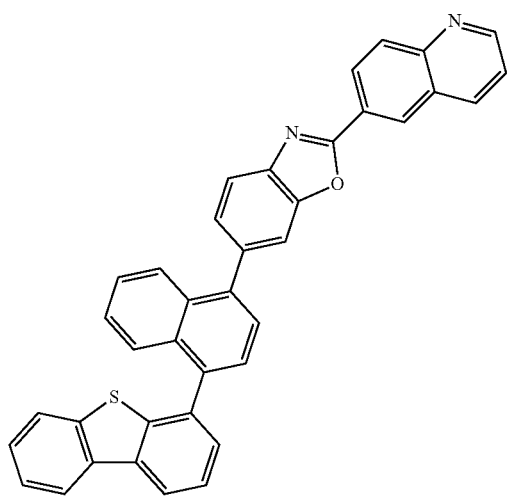
B-96
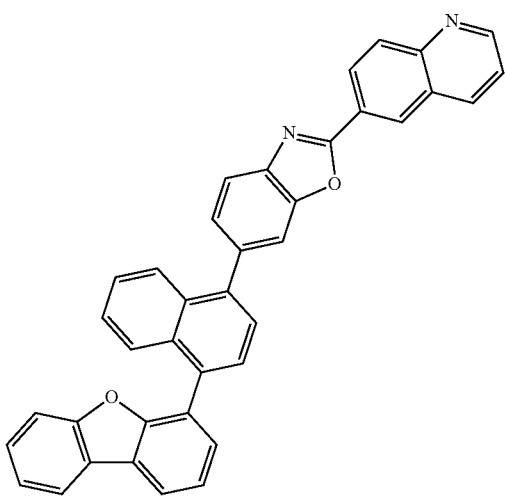
B-97
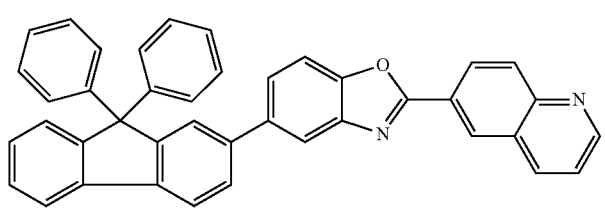

-continued
B-98
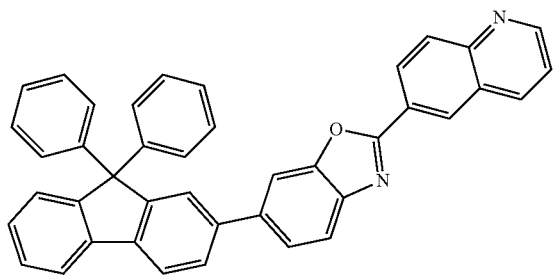
B-99
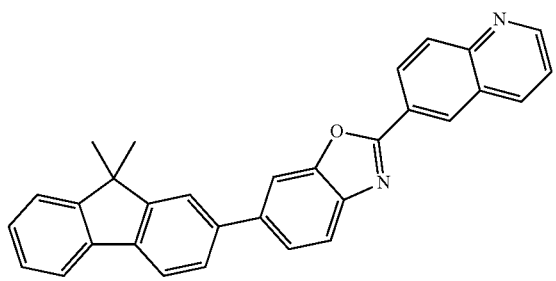
B-100
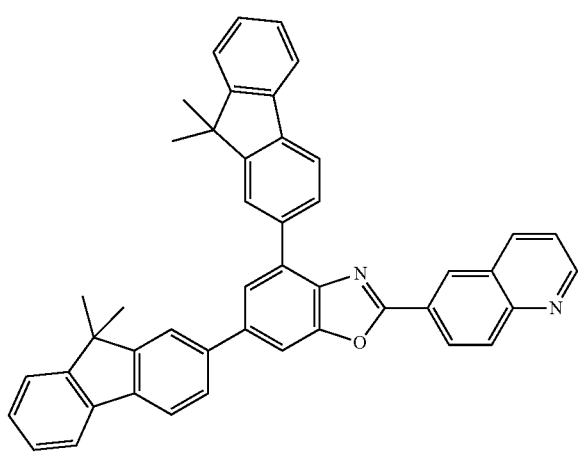
B-101
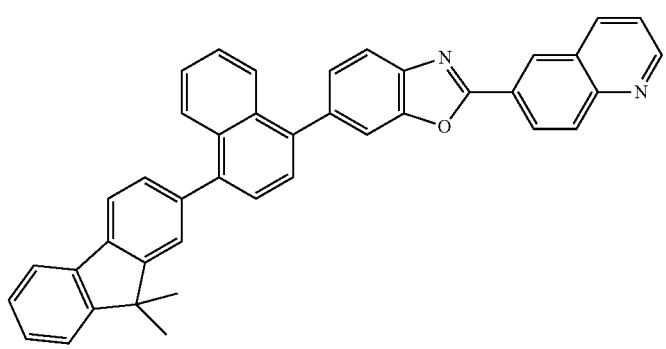
B-102
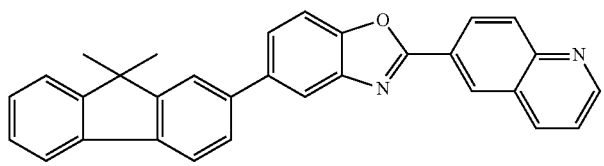

-continued
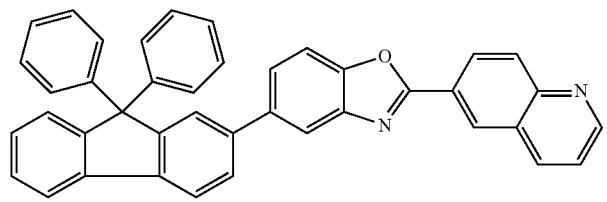
B-103
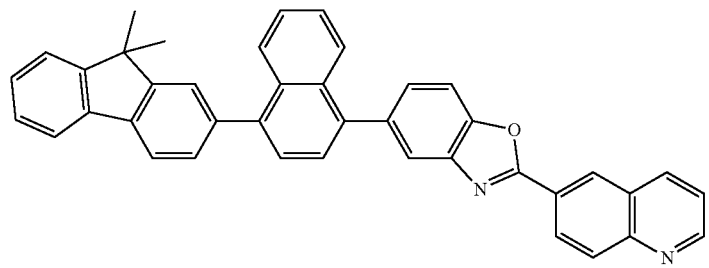
B-104
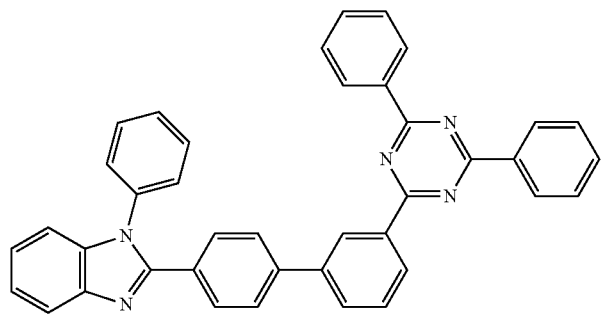
B-105
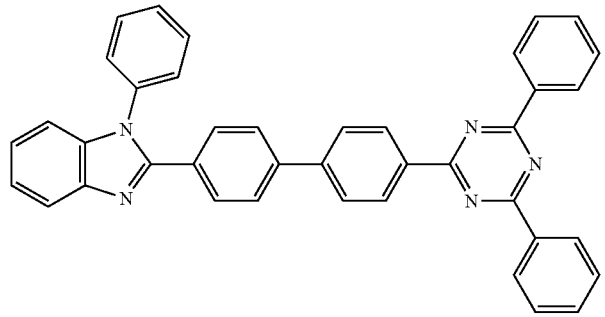
B-106
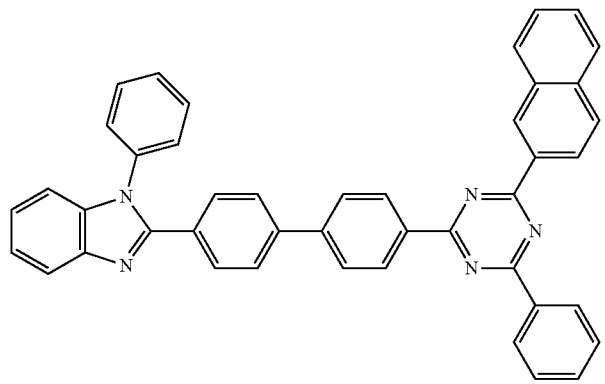
B-107

-continued
B-108
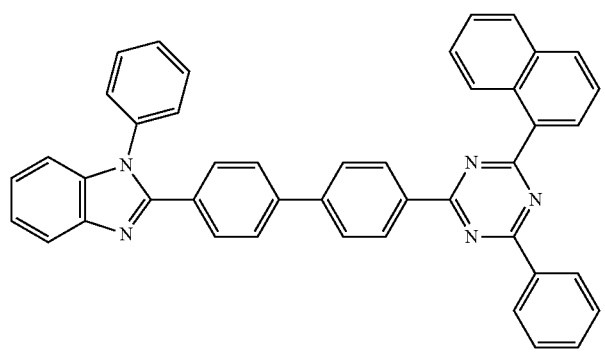
B-109
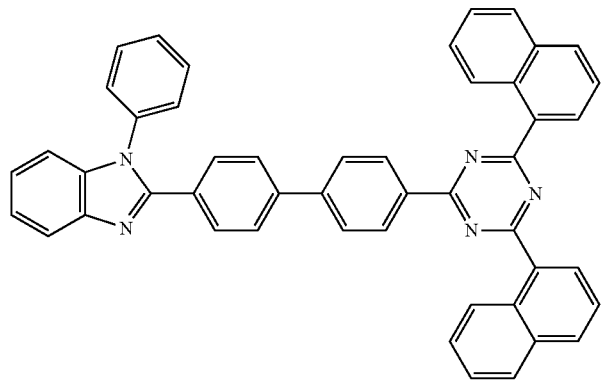
B-110
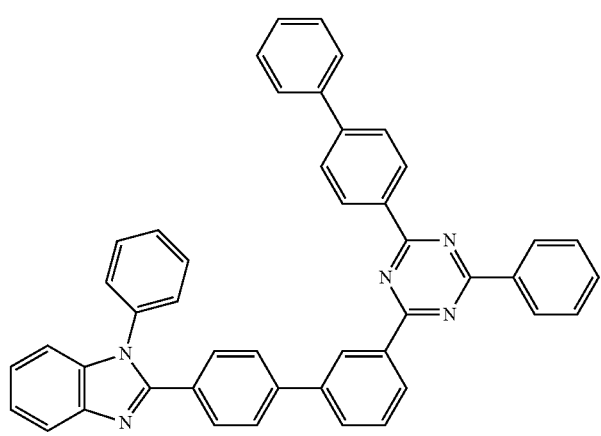
B-111
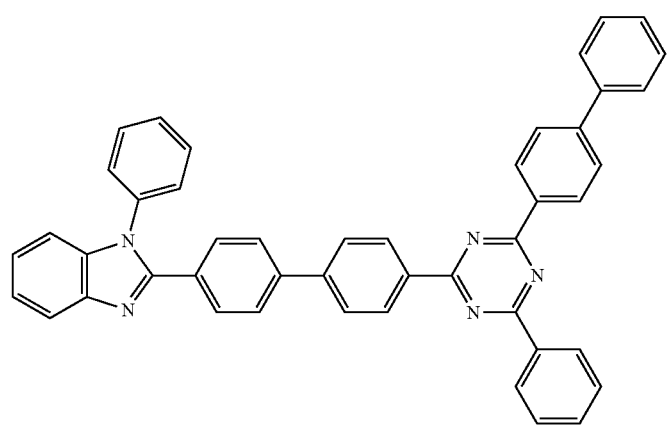

-continued
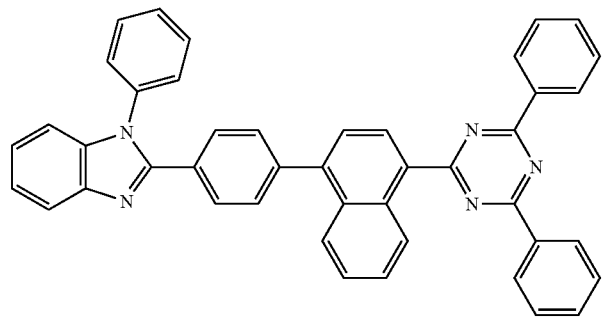
B-112
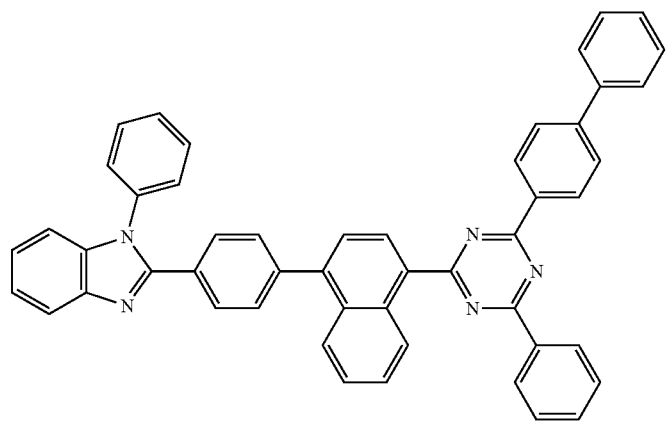
B-113
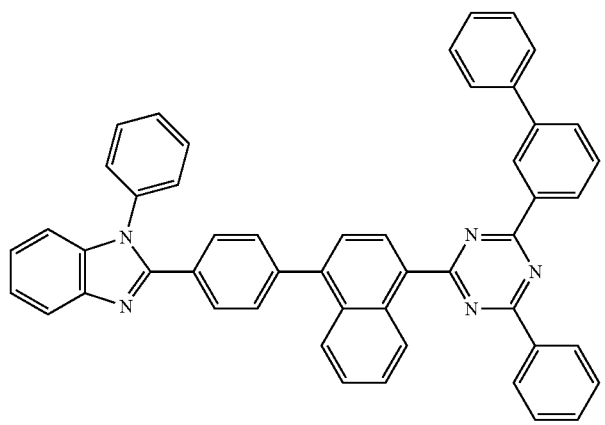
B-114
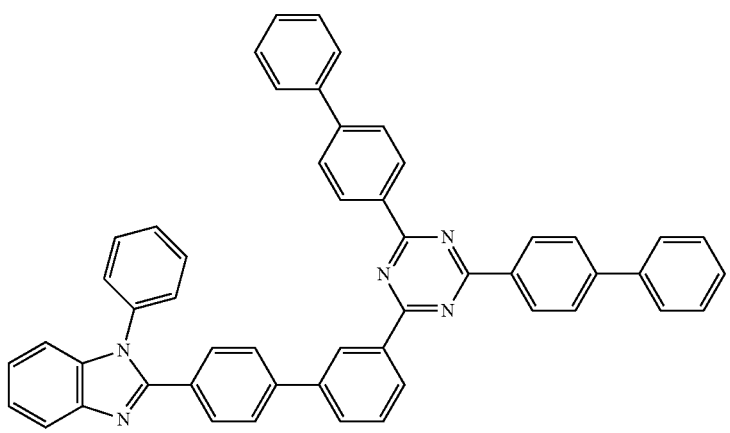
B-115

-continued
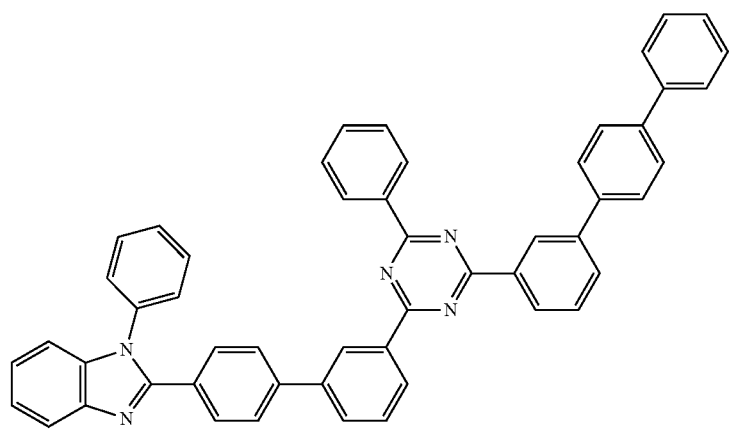
B-116
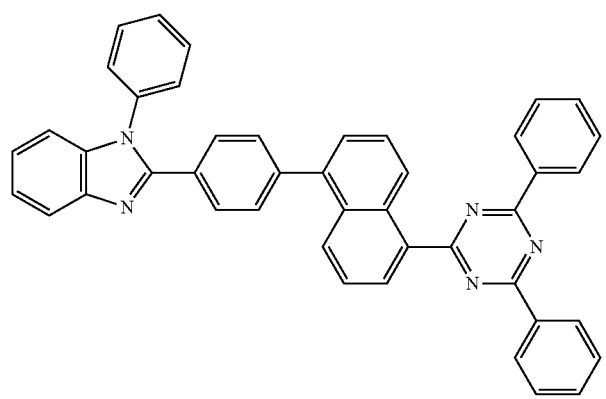
B-117
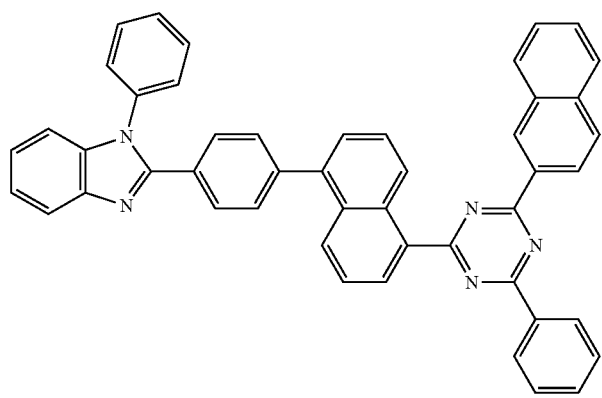
B-118
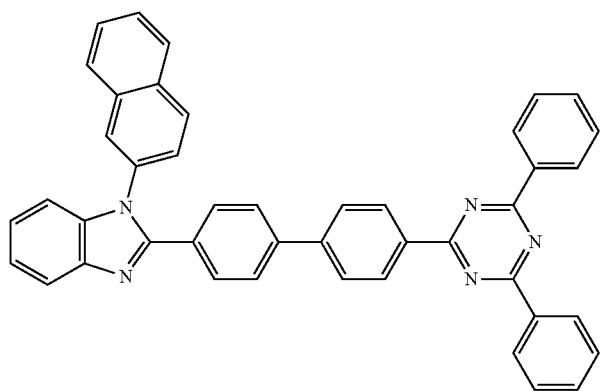
B-119

-continued
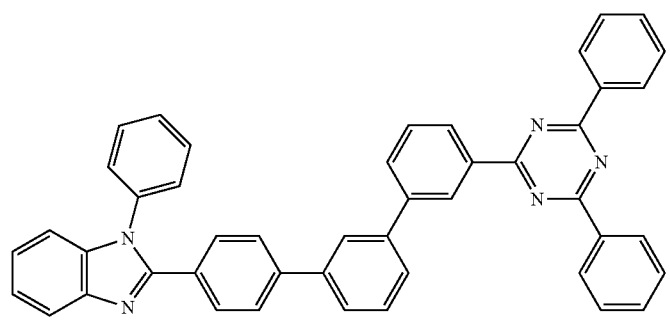
B-120
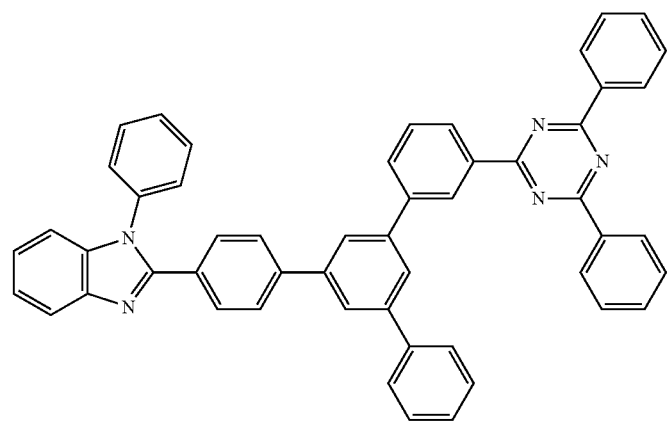
B-121
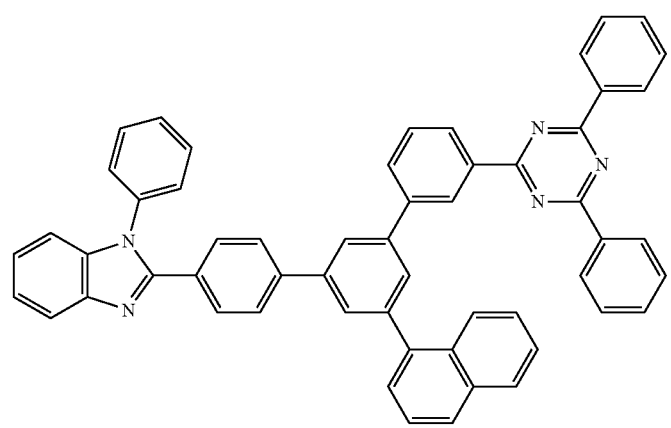
B-122
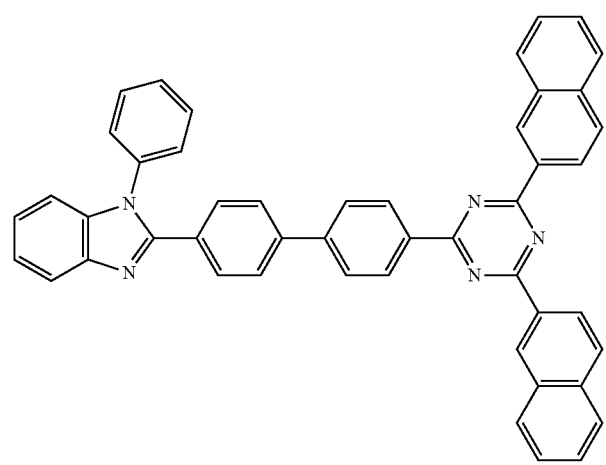
B-123

B-124

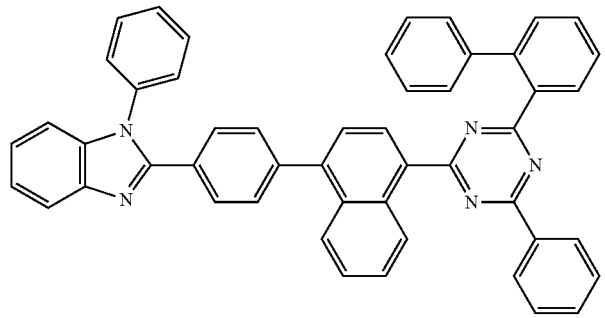

B-125

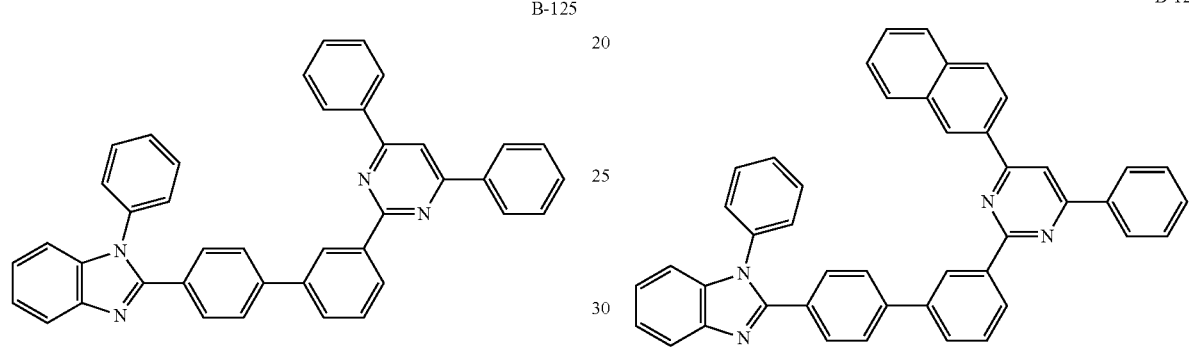

B-128

B-126

B-129

B-127

B-130

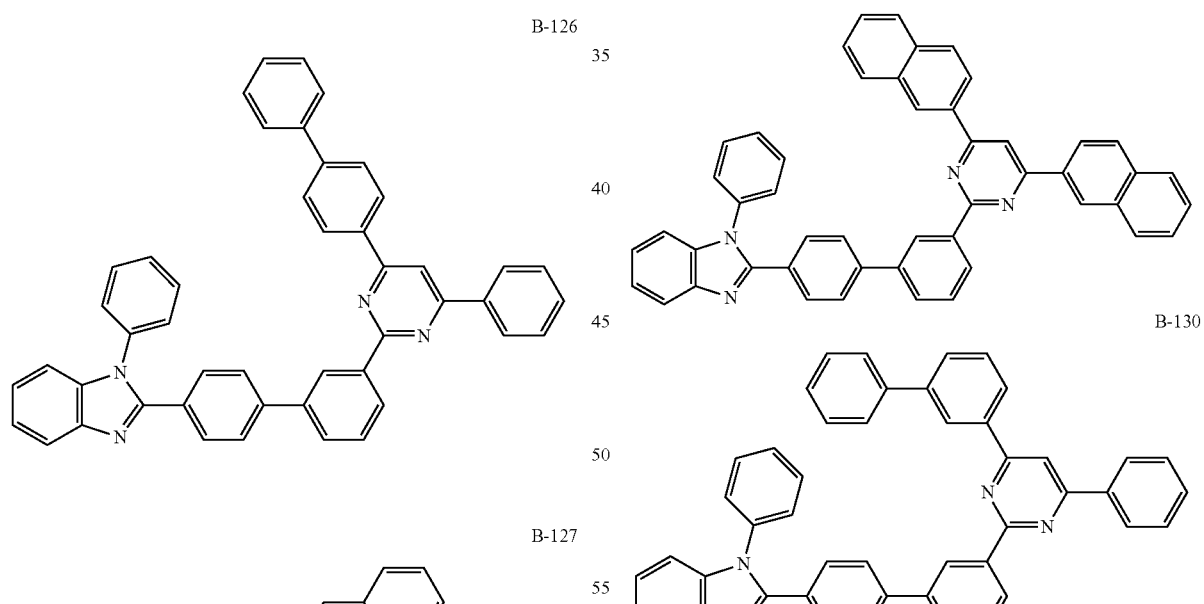

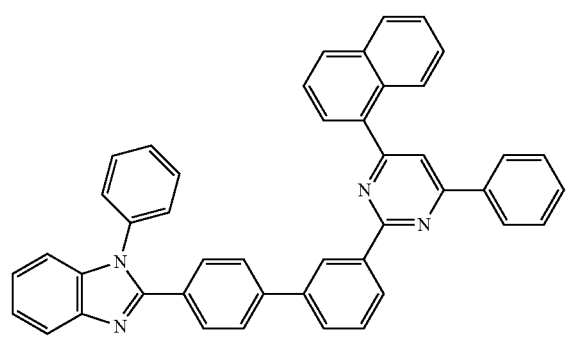

The present invention relates to the organic EL compound represented by formula 1 and an organic EL device comprising the same.

The organic EL device of the present invention comprises a first electrode, a second electrode opposing the first electrode, a light-emitting layer disposed between the two electrodes, and an electron transport zone and an electron buffer layer disposed between the light-emitting layer and the second electrode, wherein the electron buffer layer may comprise the compound represented by formula 1. When using the compound, driving voltage and efficiency of the device may be improved.

An electron buffer layer can be used to solve the problem that when the devices are exposed at high temperature in the process of panel production, current property of the devices changes, and light-emitting luminance may be accordingly changed. Thus, the characteristics of compounds which are included in an electron buffer layer are important to secure devices with similar current property to devices free from an electron buffer layer and stability for exposure at high temperature. The compound represented by formula 1 is a benzoxazole-based, benzothiazole-based, or benzoimidazole-based compound, and has excellent thermal stability and is an electron-rich group having strong electronegativity. Thus, the compound was mainly used as a light-emitting layer material, or in an electron-transport layer and a hole blocking layer. The literature specifically discloses characteristics and use of the corresponding derivatives (see Current Applied Physics., 5, 2005, 75; US 2004/0234809 A1 and US 2011/0196158 A1). Furthermore, the literature recites that intramolecular hydrogen bonding by using polarity property of Zn complexes and benzothiazole ligands in the corresponding derivatives results in excited-state intramolecular proton transfer (ESI PT) which is a type of energy transfer, and thus the derivatives are used in an electron-transport layer (see Adv. Funct. Mater., 2009, 19, 1663). However, none of the literature refer to the use of an electron buffer layer. The present invention places emphasis on driving at low voltage, efficiency improvement, and thermal stability of the devices by using optimized LUMO (lowest unoccupied molecular orbital) energy values and great electron current property of the respective corresponding compounds rather than of hole-blocking ability of the corresponding compounds as an electron-transport layer.

The compounds of the present invention have a molecular sieve size of 3 Å, and thus can be produced through simple synthesis procedure, have competitive yield and price, and have easy intermolecular electron transition due to large intramolecular overlap by small size of a molecular sieve. When the intermolecular stacking strengthens, the horizontal molecular orientation is easy, and thus realization of rapid electron current property may be possible.

Thus, the compounds according to the present invention can greatly contribute driving at low voltage, and improvement of efficiency and lifespan of organic EL devices. Such improvement of device characteristics is greatly effective in securing stability for exposure to high temperature in the process of panel production and improving performance of devices.

In organic EL devices comprising a first electrode, a second electrode, and a light-emitting layer, electron injection may be controlled by electron affinity LUMO energy value of an electron buffer layer by inserting the electron buffer layer between a light-emitting layer and the second electrode.

LUMO energy value and HOMO (highest occupied molecular orbital) energy value have inherently a negative number, but LUMO energy value and HOMO energy value in the present invention are conveniently expressed in their absolute values. Furthermore, the comparison between LUMO energy values is based on their absolute values. LUMO energy value and HOMO energy value in the present invention are calculated by Density Functional Theory (DFT).

In the organic EL device of the present invention, LUMO energy value of the electron buffer layer may be larger than that of the host compound. The difference in LUMO energy values of the electron buffer layer and the host compound may be specifically 0.2 to 0.3 eV or less. For example, LUMO energy values of the electron buffer layer and the host compound may be 1.8 to 1.9 eV and 1.6 eV, respectively, and the difference in their LUMO energy values may be 0.2 to 0.3 eV. Although LUMO barrier between the host compound and the electron buffer layer may be a factor in increasing driving voltage, when the compound represented by formula 1 is included in the electron buffer layer, it makes it easier to transport electrons to the host compound compared with other compounds. Therefore, the organic EL device of the present invention may have low driving voltage, excellent luminous efficiency, and long lifespan. In the present invention, LUMO energy values in the electron buffer layer represent specifically LUMO energy values of the compound represented by formula 1 included in the electron buffer layer.

In the organic EL device of the present invention, the electron transport zone means the zone transports electrons from the second electrode to the light-emitting layer. The electron transport zone may comprise an electron transport compound, a reducing dopant, or the combination thereof. The electron transport compound may be at least one selected from the group consisting of oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes. The reducing dopant may be at least one selected from the group consisting of an alkaline metal, an alkaline metal compound, an alkaline earth metal, a rare-earth metal, halides thereof, oxides thereof, and complexes thereof. The electron transport zone may comprise an electron transport layer, an electron injection layer, or both of them. Respective electron transport layer and electron injection layer may consist of two or more layers. LUMO energy value of the electron buffer layer may be lower or higher than that of the electron transport zone. For example, LUMO energy values of the electron buffer layer and the electron transport zone may be 1.9 eV and 1.8 eV, respectively, and the difference in their LUMO energy values may be 0.1 eV. Since the electron buffer layer has the LUMO energy value above, electrons can be easily injected to the light-emitting layer through the electron buffer layer. However, LUMO energy value of the electron transport zone may be 1.7 eV and higher or 1.9 eV and higher. For example, LUMO energy values of the electron buffer layer and the electron transport layer may be 1.7 eV and 1.9 eV, respectively, and the difference in their LUMO energy values may be 0.2 eV. Although the barrier is present between the electron buffer layer and the electron transport layer, if the compound of the present invention is used in the electron buffer layer, rapid electron current property may be realized.

Generally, LUMO energy values of the electron buffer layer may be higher than those of the host compound and the electron transport zone. For example, LUMO energy values may have the relationship of the electron buffer layer>the electron transport zone>the host compound. In view of the relation of LUMO energy values in respective layers, electrons may be restricted between the light-emitting layer and the electron buffer layer and electron injection may be hindered, and thus driving voltage may be increased. However, the electron buffer layer having the compound of formula 1 easily transports electrons to the light-emitting layer, and thus the organic EL device of the present invention may have low driving voltage, excellent luminous efficiency, and long lifespan.

The LUMO energy values can be easily measured according to various known processes. The LUMO energy values can be commonly determined by using cyclic voltammetry or ultraviolet photoelectron spectroscopy (UPS). Thus, one skilled in the art can embody the present invention by easily understanding the electron buffer layer, the host compound, and the electron transport zone which satisfy the relations of LUMO energy values according to the present invention. HOMO energy values can be easily measured in the same manner as LUMO energy values.

Hereinafter, the representative compounds of the present invention, the preparation method thereof, and luminous properties of devices comprising the compounds in an electron buffer layer will be explained in detail with reference to the following examples:

Example 1: Preparation of Compound B-7

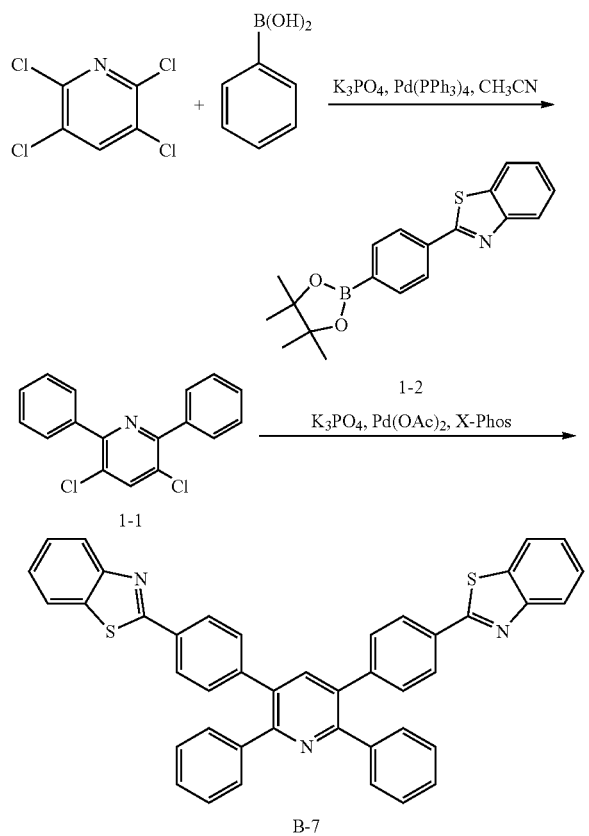

Preparation of Compound 1-1

Acetonitrile (60.0 mL) was added to a mixture of tetrachloropyridine (2.17 g, 10.0 mmol, 217.0 g/mol), phenylboronic acid (2.56 g, 21.0 mmol, 122.0 g/mol), $K_2CO_3$ (2.76 g, 20.0 mmol, 138.0 g/mol, 2M in deionized water), and tetrakis(triphenylphosphine)palladium(0) ($Pd(PPh_3)_4$) (58.0 mg, 0.05 mmol, 1155.0 g/mol) in a two-neck flask under $N_2$ atmosphere, and then the mixture was stirred under reflux for 4 hrs. The reaction results were monitored by using Thin-layer chromatography (TLC). After cooling the mixture to room temperature, white crystals were precipitated from the solution. The crystals were filtered and directly used in a next step.

$^1$H NMR (400 MHz, $CDCl_3$, ppm): 7.94 (s, 1H), 7.79-7.80 (d, J=6.8 Hz, 4H), 7.42-7.48 (m, 6H). LC-MS-ESI (m/z): $C_{17}H_{11}Cl_2N$ calculated 299.03, found $(M+H)^+$ 300.0349.

Preparation of Compound B-7

Dioxane (150.0 mL) was added to a mixture of compound 1-1 (3.00 g, 10.0 mmol, 300.0 g/mol), compound 1-2 (7.08 g, 21.0 mmol, 337.0 g/mol), $K_3PO_4$ (4.45 g, 21.0 mmol, 212.0 g/mol, 2M in deionized water), palladium(II) acetate ($Pd(OAc)_2$) (22.0 mg, 0.1 mmol, 224.0 g/mol), and X-Phos (48.0 mg, 0.1 mmol, 476.0 g/mol) in a two-neck flask under $N_2$ atmosphere, and then the mixture was stirred under reflux for 12 hrs. The reaction results were monitored by TLC. After cooling the mixture to room temperature, the residue was purified with silica gel and recrystallized to obtain white powder as a final product.

$^1$H NMR (400 MHz, $CDCl_3$, ppm): 8.05-8.08 (m, 6H), 7.91-7.93 (d, J=8.0 Hz, 2H), 7.88 (s, 1H), 7.53-7.56 (m, 4H), 7.49-7.51 (d, J=8.0 Hz, 2H), 7.38-7.45 (m, 6H), 7.28-7.30 (m, 6H). LC-MS-ESI (m/z): $C_{43}H_{27}N_3S_2$ calculated 649.16, found $(M+H)^+$ 650.1695.

Example 2: Preparation of Compound B-24

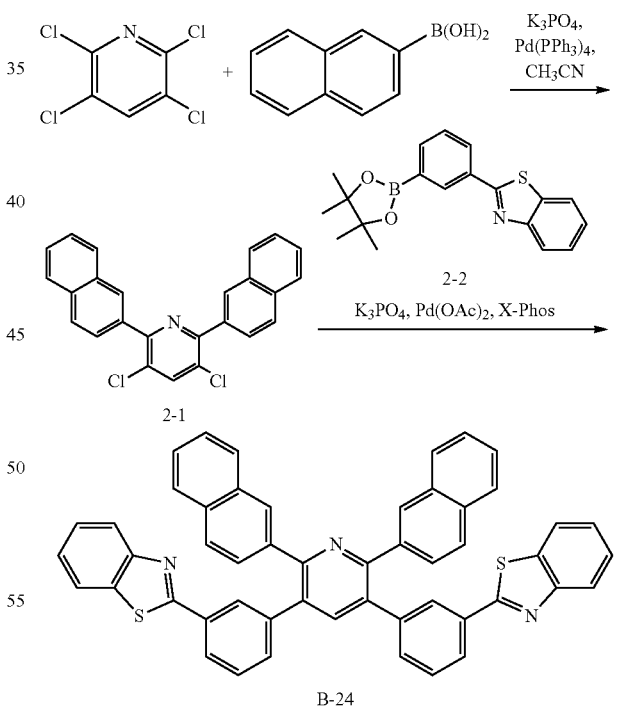

Preparation of Compound 2-1

Acetonitrile (60.0 mL) was added to a mixture of tetrachloropyridine (2.17 g, 10.0 mmol, 217.0 g/mol), naphthalene-2-yl-boronic acid (3.61 g, 21.0 mmol, 172.0 g/mol), $K_2CO_3$ (8.70 g, 63.0 mmol, 138.0 g/mol, 2M in deionized water), and Pd(PPh$_3$)$_4$ (58.0 mg, 0.05 mmol, 1155.0 g/mol) in a 250 mL two-neck flask under N$_2$ atmosphere, and then the mixture was stirred under reflux for 4 hrs. The reaction results were monitored by using TLC. After cooling the mixture to room temperature, a lot of white powder was precipitated from the solution. The powder was filtered and recrystallized in alcohol to obtain white powder as a final product.

$^1$H NMR (400 MHz, CDCl$_3$, ppm): 8.33 (s, 2H), 8.02 (s, 1H), 7.88-7.94 (m, 8H), 7.50-7.56 (m, 4H). LC-MS-ESI (m/z): C$_{25}$H$_{15}$Cl$_2$N calculated 399.06, found (M+H)$^+$ 400.0654.

Preparation of Compound B-24

Dioxane (150.0 mL) was added to a mixture of compound 2-1 (4.00 g, 10.0 mmol, 400.0 g/mol), compound 2-2 (7.08 g, 21.0 mmol, 337.0 g/mol), K$_3$PO$_4$ (4.45 g, 21.0 mmol, 212.0 g/mol, 2M in deionized water), Pd(OAc)$_2$ (22.0 mg, 0.1 mmol, 224.0 g/mol), and X-Phos (48.0 mg, 0.1 mmol, 476.0 g/mol) in a two-neck flask under N$_2$ atmosphere, and then the mixture was stirred under reflux for 12 hrs. The reaction results were monitored by TLC. After cooling the mixture to room temperature, the residue was purified with silica gel and recrystallized to obtain white powder as a final product.

$^1$H NMR (400 MHz, CDCl$_3$, ppm): 8.25 (s, 2H), 8.20 (s, 2H), 7.88 (s, 1H), 8.09 (s, 1H), 8.01-8.06 (m, 4H), 7.86-7.88 (d, J=8.0 Hz, 2H), 7.78-7.80 (d, J=8.0 Hz, 2H), 7.72-7.74 (d, J=8.4 Hz, 2H), 7.62-7.64 (d, J=8.4 Hz, 2H), 7.44-7.50 (m, 6H), 7.35-7.39 (m, 6H). LC-MS-ESI (m/z): C$_{51}$H$_{31}$N$_3$S calculated 749.20, found (M+H)$^+$ 750.2013.

Example 3: Preparation of Compound B-56

1-Phenyl-2-(4-(4,4,5,5-tetramethyl-1,3,2-dioxaborolan-2-yl)phenyl)-1H-benz[d]imidazole

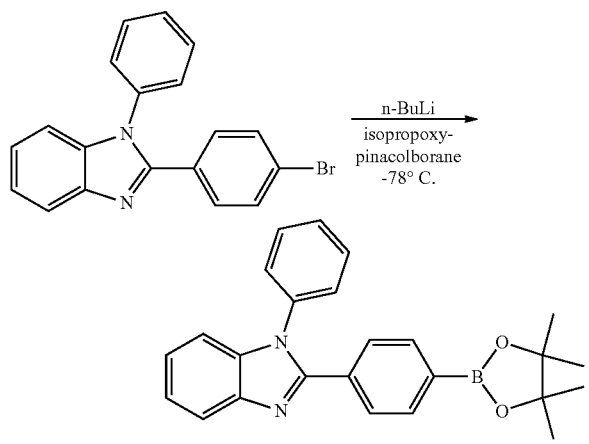

A 500 mL four-neck round-bottomed flask (RBF) equipped with an overhead stirrer, a nitrogen inlet, a 125 mL addition funnel, and a thermocouple was purged with anhydrous nitrogen for 10 min. The flask was charged with 2-(4-bromophenyl)-1-phenyl-1H-benzo[d]imidazole (25.0 g, 71.59 mmol) and THF (250.0 mL), and then cooled to −71° C. of internal temperature. 1.6 M n-butyl lithium solution (67.0 mL, 107.2 mmol) in hexane was added dropwise into the flask via an addition funnel for 30 min, and the mixture was further stirred at an internal temperature of −72° C. of for 30 min. 2-isopropoxy-4,4,5,5-tetramethyl-1,3,2-dioxaborolane (32.0 mL, 171.99 mmol) was added to the resulting dark red solution via an addition funnel for 30 min while maintaining the temperature of below −70° C. After removing a cooling bath, the brown slurry was warmed to room temperature and stirred for 16 hrs. The reactants were concentrated by using a rotary evaporator, dissolved in dichloromethane (350.0 mL), and washed with water (200.0 mL) to obtain a cloudy mixture. The aqueous layer was extracted with dichloromethane (2×150.0 mL), and the combined organic layers were dried with MgSO$_4$, filtered, and concentrated by using a rotary evaporator. The resulting yellow solid was washed with hexane (100.0 mL) and tan colored solids (22.2 g) were obtained by mostly removing the color. The solids were divided into two crops and recrystallized from acetonitrile (~180.0 mL per crop) to obtain pale orange crystalline solids as a title compound (16.5 g, 41.6 mmol, 58%).

2-Chloro-4-(naphthalen-1-yl)quinazoline (Precursor 7)

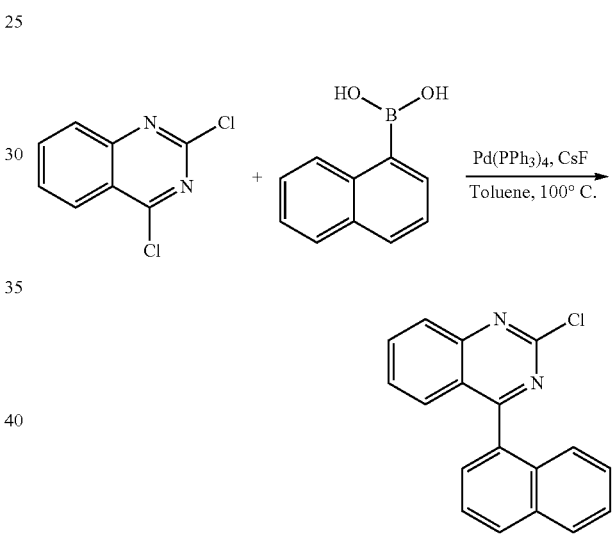

A magnetic stirred mixture of 2,4-dichloroquinazole (7.5 g, 38.0 mmol), 1-naphthyl boronic acid (6.5 g, 38.0 mmol, 1 equivalent), and CsF powder (11.5 g, 76.0 mmol, 2 equivalents) in anhydrous toluene (150.0 mL) was charged into a glove box with Pd(PPh$_3$)$_4$ (2.2 g, 1.9 mmol, 5.0 mol %). The reaction mixture was heated at 100° C. overnight. The solvent was removed from the mixture, the crude product was dissolved in chloroform and washed with water, the obtained organic layers were concentrated into a small volume followed by loading into a small silica gel plug and removing color and residual boronic ester. The product was loaded into ISCO purification system under anhydrous condition and eluted with gradient of chloroform/hexane to obtain a target compound (9.0 g, 31.0 mmol, 81%).

$^1$H NMR (500 MHz, CDCl$_3$) δ 8.14-8.08 (m, 1H), 8.05 (t, J=9.2 Hz, 1H), 8.00-7.90 (m, 2H), 7.69-7.58 (m, 3H), 7.57-7.45 (m, 3H), 7.45-7.38 (m, 1H); $^{13}$C NMR (126 MHz, CDCl$_3$) δ 172.37, 157.10, 152.56, 135.25, 133.58, 133.11, 131.25, 130.46, 128.49, 128.13, 128.03, 127.96, 127.73, 127.11, 126.47, 125.24, 124.99, 123.30.

4-(Naphthalene-1-yl)-2-(4-(1-phenyl-1H-benz[d]imidazol-2-yl)phenyl) quinazoline

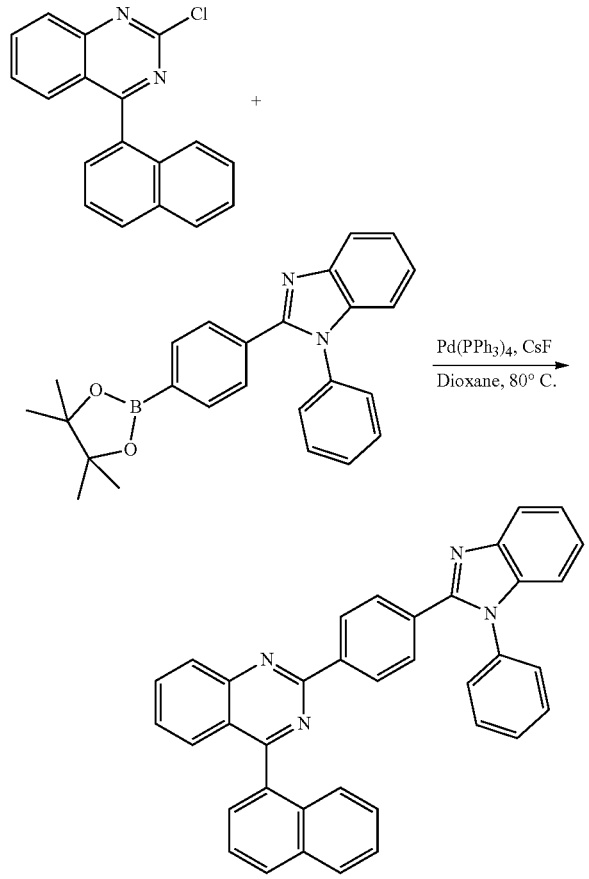

A magnetic stirred mixture of 2-naphthyl-4-chloroquinazole (3.5 g, 12.0 mmol), 1-phenyl-2-(4-(4,4,5,5-tetramethyl-1,3,2-dioxaborolan-2-yl)phenyl)-1H-benzo[d]imidazole (4.8 g, 12.0 mmol, 3 equivalents), and KOAc powder (2.94 g, 30.0 mmol, 2.5 equivalents) in dioxane (100.0 mL) was charged into a glove box with [1,1'-bis(diphenylphosphine)ferrocene]dichloropalladium(II) (Pd(dppf)Cl$_2$) (0.3 g, 0.36 mmol, 3.0 mol %). The reaction mixture was heated at 80° C. overnight. Water was added to the solid and the organic matters were extracted with chloroform. The obtained organic layers were dried, the solvent was removed from the layers, and the product was purified via preparative chromatography (ISCO Teledyne purification system) by using a chloroform/EtOAc gradient system to obtain a target compound (~5.5 g, Yield: 87%, Purity by LC: ~99%). The product was recrystallized from boiling chlorobenzene to obtain a target compound (4.5 g, Purity by LC: >99.8%).

$^1$H NMR (500 MHz, CDCl3) δ 8.68-8.61 (m, 2H), 8.19 (ddd, J=8.5, 1.1, 0.7 Hz, 1H), 8.10-8.04 (m, 1H), 8.01-7.97 (m, 1H), 7.95-7.87 (m, 2H), 7.77-7.71 (m, 2H), 7.69-7.58 (m, 4H), 7.57-7.33 (m, 9H), 7.33-7.28 (m, 1H), 7.27-7.23 (m, 1H); $^{13}$C NMR (126 MHz, CDCl3) δ 168.99, 159.58, 151.99, 151.38, 143.00, 138.89, 137.29, 136.93, 134.70, 133.90, 133.61, 131.69, 131.51, 129.84, 129.71, 129.56, 128.94, 128.54, 128.33, 127.81, 127.37, 127.23, 127.19, 126.64, 126.17, 125.60, 124.98, 123.39, 123.36, 122.97, 119.84, 110.39.

Example 4: Preparation of Compound B-104

Quinoline-6-carbonyl chloride (Precursor 1)

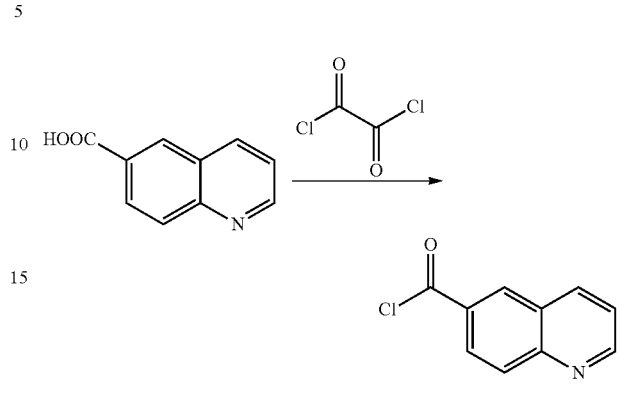

1,4-Dioxane (250.0 mL) was added with 10 drops of dimethylformamide (DMF) to quinoline-6-carboxylic acid (25.4 g, 146.5 mmol) which was charged under nitrogen to a 1 L RBF equipped with a drying tube attached to a gas scrubber and a septum. In a glove box, oxalyl chloride (25.1 g, 197.8 mmol, 1.35 equivalents) was weighed into a septum vial. The vial was closed and was then removed from the glove box. The weighed oxalyl chloride was added several times to the reactants via a syringe under nitrogen. The reactants were stirred until gas-forming mostly ceased. The reactants were stirred at room temperature overnight. The volatile materials were removed from the reactants by using a rotary evaporator. Anhydrous toluene was added several times to remove trace HCl, and continuously evaporated by using a rotary evaporator. The final product was obtained in the form of colorless to pale yellow powder (28.0 g, 146.4 mmol, 100%).

$^1$H-NMR: (500 MHz, CDCl3) δ 9.35 (dd, J=5.2, 1.5 Hz, 1H), 9.09 (d, J=8.5 Hz, 1H), 9.09 (d, J=9.0 Hz, 1H), 9.01 (d, J=2.0 Hz, 1H), 8.64 (dd, J=9.1, 2.0 Hz, 1H), 8.14 (dd, J=8.4, 5.2 Hz, 1H); $^{13}$C-NMR (126 MHz, CDCl$_3$) δ 122.92, 123.90, 128.21, 133.44, 133.79, 134.55, 140.95, 146.44, 147.11, 166.69.

N-(2,5-Dibromophenyl)quinoline-6-carboxamide (Precursor 2)

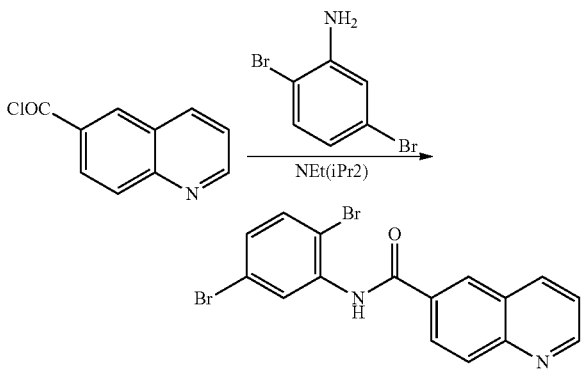

2,5-Dibromoaniline was recrystallized from a mixture of toluene/hexane solvents. Under nitrogen, 2,6-dibromoaniline (36.1 g, 144.0 mmol) and quinoline-6-carbonyl chloride (Precursor 1, 27.3 g, 142.0 mmol, 0.99 equivalent) were dissolved in anhydrous 1,4-dioxane (350.0 mL) in a 1 L one-neck RBF equipped with a large stirrer bar and a reflux condenser. While stirring the solution, a Hünig base (37.2 g, 288.0 mmol, 2.0 equivalents) was added to the solution. The contents in the flask were heated to about 40° C. by an exothermic reaction. The mixture was stirred and cooled to room temperature. The reactants were heated to 100° C. in an oil bath for 20 hrs. A complete consumption of 2,5-dibromoaniline was monitored by TLC. The reactants were poured into warm water (1.5 L) and fine deposits were then formed. The solution was neutralized with sodium carbonate and filtered. The collected residue was dried by suction and rinsed with acetone (25.0 mL) and toluene (25.0 mL). The filter cake was transported to a 1 L flask, trace water was removed by azeotropic distillation with toluene on a rotary evaporator, and the cake was kept under high-degree vacuum overnight. The dried residue was recrystallized from monochlorobenzene (1.5 L) by using activated carbon as a decolorant. The crystals were separated by filtration and dried under high-degree vacuum (45.05 g, 111.0 mmol, 77.1%, off-white needles). Addition purification was effected by recrystallization from 1,4-dioxane (~0.9 L). The final product was obtained in the form of off-white crystal (plate) (40.0 g, 98.5 mmol, 68.5%).

$^1$H NMR (500 MHz, DMSO-$d_6$) δ 10.38 (s, 1H), 9.03 (dd, J=4.2, 1.7 Hz, 1H), 8.68 (d, J=2.0 Hz, 1H), 8.55 (ddd, J=8.3, 1.6, 0.8 Hz, 1H), 8.28 (dd, J=8.8, 2.0 Hz, 1H), 8.16 (d, J=8.8 Hz, 1H), 7.87 (d, J=2.4 Hz, 1H), 7.71 (d, J=8.6 Hz, 1H), 7.65 (dd, J=8.3, 4.2 Hz, 1H), 7.46 (dd, J=8.6, 2.4 Hz, 1H); $^{13}$C-NMR (126 MHz, DMSO-$d_6$) δ 119.73, 120.70, 122.78, 127.59, 128.26, 129.19, 129.77, 131.01, 131.25, 132.09, 134.78, 137.63, 138.58, 149.45, 152.86, 165.52. GC/CI$^+$ m/z (%): 404.96 (50) [M+H, 2×$^{79}$Br]$^+$, 406.97 (100) [M+H, $^{79}$Br, $^{81}$Br]$^+$, 408.96 (50) [M+H, 2×$^{81}$Br]$^+$.

5-Bromo-2-(quinolin-6-yl)benz[d]oxazole (Precursor 3)

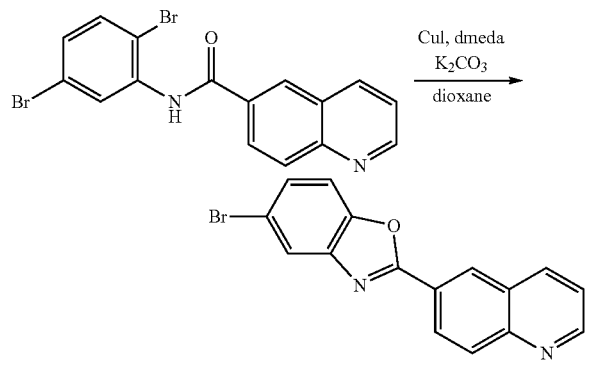

All the reaction steps were carried out in a glove box. CuI (821.0 mg, 4.31 mmol, 0.05 equivalent) was dissolved in 1,4-dioxane (8.0 mL), and N,N'-dimethylethylenediamine (928.0 µL, 760.0 mg, 8.62 mmol, 0.1 equivalent) was added thereto. Precursor 2 (35.0 g, 86.2 mmol, 1.0 equivalent) was weighed into a separate 1 L flask. K$_3$PO$_4$ (54.9 g, 259.0 mmol, 3.0 equivalents) was finely ground with a mortar in the glove box and added to the flask with 1,4-dioxane (300.0 mL). The reaction was initiated by the addition of a CuI/N,N'-dimethylethylenediamine solution, vigorously stirred, and heated to 90° C. overnight. The contents of the reaction vessel were added to the diluted aqueous ammonium hydroxide to precipitate the product. The precipitate was separated by filtration, washed with water, rinsed with a small volume of acetone, and dried under high-degree vacuum. The dried precipitate was dissolved in chloroform and filtered through a short plug of silica and basic alumina. The eluted product was collected and the solvent was removed by a rotary evaporator. The residue was dissolved in the minimum quantity of boiling ethyl acetate (approximately 1 L). The residue was slowly cooled in a Dewar vessel and pure benzoxazole was crystallized in the form of colorless microcrystal. The product was separated by filtration and dried under high-degree vacuum (17.0 g, 52.3 mmol, 60.7%).

$^1$H-NMR (500 MHz, CDCl$_3$) δ 9.00 (dd, J=4.2, 1.7 Hz, 1H), 8.71 (d, J=1.9 Hz, 1H), 8.51 (dd, J=8.9, 2.0 Hz, 1H), 8.31-8.24 (m, 1H), 8.23 (d, J=8.8 Hz, 1H), 7.93 (t, J=1.2 Hz, 1H), 7.53-7.45 (m, 3H); $^{13}$C-NMR (126 MHz, CDCl$_3$) δ 111.84, 117.55, 122.13, 123.17, 124.67, 127.57, 127.95, 128.19, 128.44, 130.56, 136.81, 143.74, 149.58, 149.91, 152.18, 163.47; GC/ESI$^+$ m/z (%): 326.03 (100) [M+H, $^{79}$Br]$^+$, 328.03 (100) [M+H, $^{81}$Br]$^+$.

5-(4-(9,9-Dimethyl-9H-fluoren-3-yl)naphthalen-1-yl)-2-(quinoline-6-yl)benz[d]oxazole In a glove box, Pd(OAc)$_2$ (9.2 mg, 41.0 µmol) and s-Phos (33.7 mg, 82.1 µmol) were dissolved in 1,4-dioxane (1.0 mL). K$_3$PO$_4$ (5.23 g, 24.6 mmol, 3.0 equivalents) was weighed into a 20 mL vial and water (5.16 mL) was added thereto. 5-Bromo-2-(quinoline-6-yl)benz[d]oxazole (Precursor 3, 2.67 g, 8.21 mmol) and 2-(4-(9,9-dimethyl-9H-fluoren-2-yl)naphthalen-1-yl)-4,4,5,5-tetramethyl-1,3,2-dioxaborolane (4.40 g, 9.85 mmol, 1.2 equivalent; the synthesis of this compound was known, for example, in WO 2009/139499 A1) were dissolved in 1,4-dioxane (33.0 mL), and an aqueous K$_3$PO$_4$ solution followed by a catalytic solution were added thereto. The reactants were stirred at room temperature overnight. Chloroform and water were added to the reactants and worked up until the two phases became clear. The chloroform phase was separated and the water phase was re-extracted with chloroform. The combined organic phases were dried with MgSO$_4$ and treated with an activated carbon. The mixture was filtered through a short plug of silica and basic alumina, and dried by using vacuum concentration. The residue was purified by preparative chromatography by using a gradient of normal phase silica cartridge (220.0 g) (Grace) and 0-12% ethyl acetate in toluene. The pure fractions were collected by TLC and the solvent

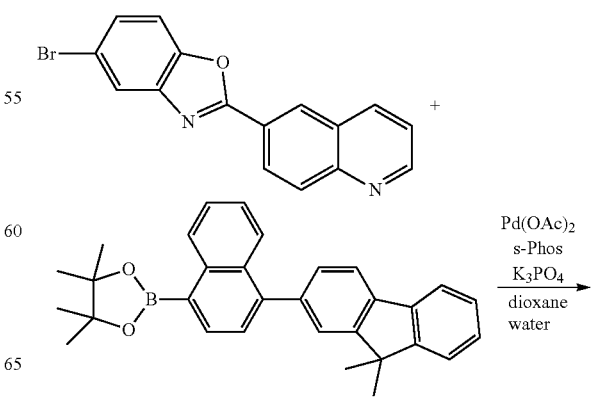

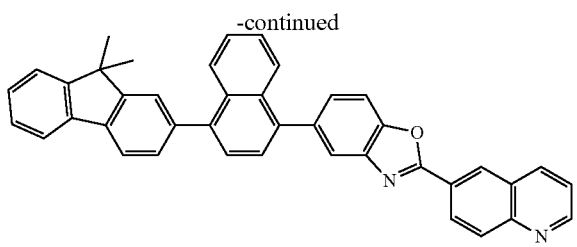

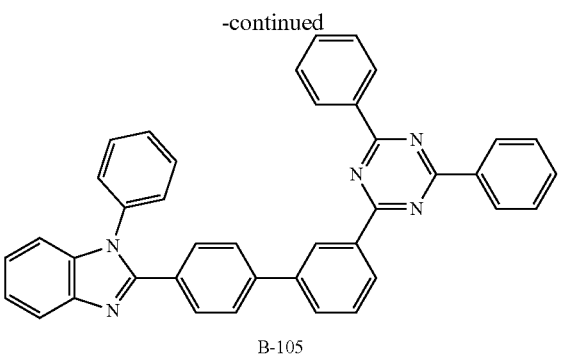

B-105 was removed under reduced pressure. The glassy residue was dissolved in a small volume of toluene (~30.0 to 50.0 mL) and hexane was slowly added thereto shortly before the precipitation point. The solution was kept overnight to be crystallized.

The crystals were separated by filtration and dried at 45° C. under high-degree vacuum overnight. The product was obtained in the form of colorless microcrystal (2.92 g, 5.67 mmol, 69.1%, Purity by HPLC: 99.8%). The mother liquid was completely evaporated, the crystals were re-dissolved in a small volume of toluene, and hexane was added thereto shortly before the precipitation point to obtain a second batch (0.76 g, 1.48 mmol, 18.1%, Purity by HPLC: 99.6%). The product was further purified by sublimation to obtain the purity of the two batches as 99.8% and 99.7%, respectively.

$^1$H-NMR (500 MHz, CDCl$_3$) δ 9.01 (dd, J=4.2, 1.7 Hz, 1H), 8.82 (d, J=1.9 Hz, 1H), 8.62 (dd, J=8.8, 1.9 Hz, 1H), 8.32 (ddd, J=8.6, 1.6, 0.7 Hz, 1H), 8.28 (dd, J=8.8, 0.8 Hz, 1H), 8.09 (ddt, J=6.8, 3.3, 1.7 Hz, 1H), 8.04-7.97 (m, 2H), 7.86 (dd, J=7.7, 0.6 Hz, 1H), 7.83-7.77 (m, 1H), 7.76 (dd, J=8.2, 0.6 Hz, 1H), 7.63 (dd, J=1.6, 0.6 Hz, 1H), 7.62-7.42 (m, 8H), 7.42-7.31 (m, 2H), 1.57 (s, 6H); $^{13}$C-NMR (126 MHz, CDCl$_3$) δ 27.24, 47.01, 110.33, 119.79, 120.10, 121.64, 122.11, 122.66, 124.52, 125.23, 125.99, 126.05, 126.33, 126.54, 126.58, 126.91, 127.07, 127.34, 127.72, 127.91, 128.00, 128.09, 129.04, 130.55, 132.15, 132.22, 136.87, 137.95, 138.48, 138.95, 139.16, 139.73, 140.57, 142.42, 149.56, 150.44, 152.06, 153.81, 153.89, 163.10; ESI/LC/MS/MS: m/z=565 (standard peak, [M+H]$^+$), fragmenting to 549, 129, 155, 352. C Log P: 11.32 (ChemBio-Draw Ultra, Version 12.0.2.1076, CambridgeSoft 2010). Additional calculated data: HOMO: -5.41 eV, LUMO: -1.92 eV, Triplet Energy: 2.47 eV.

Example 5: Preparation of Compound B-105

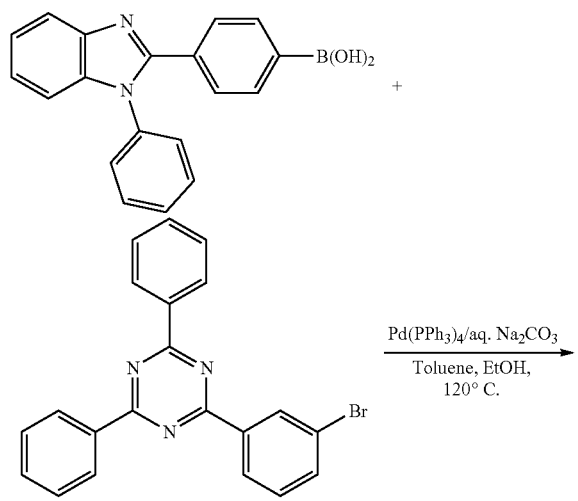

After introducing to a reaction vessel (4-(1-phenyl-1H-benz[d]imidazol-2-yl)phenyl)boronic acid (5.4 g, 17.00 mmol), 2-(3-bromophenyl)-4,6-diphenyl-1,3,5-triazine (6 g, 15.45 mmol), tetrakis(triphenylphosphine)palladium (0.6 g, 0.46 mmol), sodium carbonate (4.1 g, 38.63 mmol), toluene 78 mL, and ethanol 19 mL, distilled water 19 mL was added thereto, and the mixture was stirred at 120° C. for 6 hours. After completing the reaction, the mixture was washed with distilled water and extracted with ethyl acetate. The organic layer was dried with magnesium sulfate, and the solvent was removed with a rotary evaporator. The residue was purified with column chromatography to obtain compound B-105 (5.5 g, yield: 62%).

|       | MW     | UV     | PL     | M.P    |
|-------|--------|--------|--------|--------|
| B-105 | 577.68 | 356 nm | 389 nm | 282° C.|

Comparative Examples 1 and 2: Production of a Blue Light-Emitting OLED Device which does not Comprise an Electron Buffer Layer According to the Present Invention OLED devices were produced as follows: A transparent electrode indium tin oxide (ITO) thin film (10 Ω/sq) on a glass substrate for an OLED device (GEOMATEC CO., LTD., Japan) was subjected to an ultrasonic washing with acetone, ethanol, and distilled water, sequentially, and was then stored in isopropanol. Next, the ITO substrate was mounted on a substrate holder of a vacuum vapor depositing apparatus. N$^4$,N$^{4'}$-diphenyl-N$^4$,N$^{4'}$-bis(9-phenyl-9H-carbazol-3-yl)[1,1'-biphenyl]-4,4'-diamine (compound HI-1) was introduced into a cell of the vacuum vapor depositing apparatus, and the pressure in the chamber of the apparatus was then controlled to 10$^{-6}$ torr. Thereafter, an electric current was applied to the cell to evaporate the introduced material, thereby forming a first hole injection layer having a thickness of 60 nm on the ITO substrate. Dipyrazino[2,3-f:2',3'-h]quinoxaline-2,3,6,7,10,11-hexacarbonitrile (HAT-CN) (compound HI-2) was then introduced into another cell of the vacuum vapor depositing apparatus, and an electric current was applied to the cell to evaporate the introduced material, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluoren-2-amine (compound HT-1) was introduced into another cell of the vacuum vapor depositing apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor depositing apparatus, and an electric current was applied to the cell to evaporate the introduced material, thereby forming a second hole transport layer having a thickness of 5 nm on the first hole transport layer. Thereafter, compound BH-1 as a host was introduced into one cell of the vacuum vapor depositing apparatus and compound BD-1 as a dopant was introduced into another cell. The two materials were evaporated at a different rate and the dopant was deposited in a doping amount of 2 wt %, based on the total weight of the host and dopant, to form a light-emitting layer having a thickness of 20 nm on the second hole transport layer. Next, 2-(4-(9,10-di(naphthalene-2-yl)anthracene-2-yl)phenyl)-1-phenyl-1H-benzo[d]imidazole (compound ETL-1) was introduced into one cell and lithium quinolate was introduced into another cell of the vacuum vapor depositing apparatus. The two materials were evaporated at the same rate and were respectively deposited in a doping amount of 50 wt % to form an electron transport layer having a thickness of 35 nm on the light-emitting layer. After depositing lithium quinolate (compound EIL-1) having a thickness of 2 nm as an electron injection layer on the electron transport layer, an Al cathode having a thickness of 80 nm was then deposited by another vacuum vapor deposition apparatus on the electron injection layer. Thus, OLED devices were produced. All the materials used for producing the OLED device were purified by vacuum sublimation at $10^{-6}$ torr prior to use.

Figure 3:
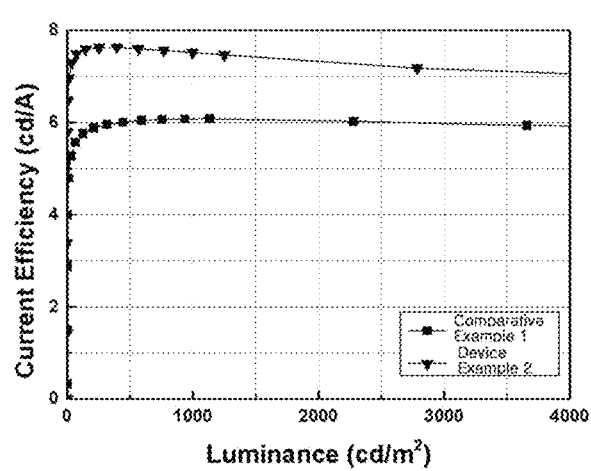
FIG. 3 shows graphs of current efficiency (cd/A) vs. luminance (cd/m$^2$) of the organic EL devices which are respectively produced according to Device Example 2 and Comparative Example 1.

The current efficiency vs. luminance of the OLED device produced in Comparative Example 1 is depicted in FIG. 3. In addition, driving voltage at a luminance of 1,000 nit, luminous efficiency, and CIE color coordinate of the OLED devices produced in the Comparative Examples are as provided in Table 1 below.

Device Examples 1 to 6: Production of a Blue Light-Emitting OLED Device According to the Present Invention OLED devices were produced in the same manner as in Comparative Example 1, except that the thickness of the electron transport layer was 30 nm and an electron buffer layer having a thickness of 5 nm was inserted between the light-emitting layer and the electron transport layer. The current efficiency vs. luminance of the OLED device produced in Device Example 2 is depicted in FIG. 3. Also, evaluation results of the devices of Device Examples 1 to 6 are as provided in Table 1 below.

TABLE 1

| | Electron Buffer Layer | Voltage (V) | Efficiency (cd/A) | Color Coordinate (x) | Color Coordinate (y) | LUMO | HOMO |
|---|---|---|---|---|---|---|---|
| Comparative Example 1 | — | 4.4 | 6.1 | 140 | 101 | | |
| Comparative Example 2 | BF-1 | 4.6 | 6.1 | 139 | 102 | 1.95 | 4.98 |
| Device Example 1 | B-72 | 4.3 | 7.3 | 140 | 100 | 1.97 | 5.44 |
| Device Example 2 | B-7 | 4.4 | 7.5 | 139 | 100 | 1.91 | 5.65 |
| Device Example 3 | B-66 | 4.2 | 7.5 | 139 | 99 | 1.80 | 5.94 |
| Device Example 4 | B-102 | 4.3 | 7.2 | 139 | 100 | 1.91 | 5.55 |
| Device Example 5 | B-30 | 4.4 | 7.5 | 139 | 100 | 1.70 | 5.95 |
| Device Example 6 | B-68 | 4.4 | 6.8 | 139 | 100 | 1.73 | 5.62 |

From Table 1 above, it can be seen that since the devices of Device Examples 1 to 6 had rapid electron current property of the electron buffer layer, the devices had high efficiency and long lifespan compared with the devices of the Comparative Examples having no electron buffer layer or not using the material of the present invention in the electron buffer layer. Furthermore, upon comparing Comparative Example 2 with the Device Examples, although compound BF-1 used in Comparative Example 2 had similar LUMO energy value to the compounds of the Device Examples, electron injection was not relatively smooth to show high voltage and low efficiency.

Analysis of Property

Relative electron current property of the devices according to the present invention was compared with the device having no electron buffer layer and not comprising the material of the present invention in the electron buffer layer by preparing an Electron Only Device (EOD) comprising a light-emitting layer.

The device was produced as follows: Barium and 2,9-dimethyl-4,7-diphenyl-1,10-phenanthroline (BCP) were introduced into cells in a vacuum vapor depositing apparatus. Thereafter, an electric current was applied to the cells to evaporate the introduced materials, thereby forming a hole blocking layer (HBL) having a thickness of 10 nm on the ITO substrate. Thereafter, compound BH-1 as a host was introduced into one cell and compound BD-1 as a dopant was introduced into another cell of the vacuum vapor depositing apparatus. The two materials were evaporated at a different rate and the dopant was deposited in a doping amount of 2 wt %, based on the total weight of the host and dopant, to form a light-emitting layer having a thickness of 20 nm on a hole transport layer. Next, 2-(4-(9,10-di(naphthalene-2-yl)anthracene-2-yl)phenyl)-1-phenyl-1H-benzo[d]imidazole was introduced into one cell and lithium quinolate was introduced into another cell of the vacuum vapor depositing apparatus. The two materials were evaporated at the same rate and were respectively deposited in a doping amount of 50 wt % to form an electron transport layer having a thickness of 35 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use. If an electron buffer layer is present, the thickness of the electron transport layer was decreased to 30 nm and an electron buffer layer having a thickness of 5 nm was inserted between the light-emitting layer and the electron transport layer. Voltages at 10 and 100 $mA/cm^2$ according to each material of the electron buffer layer are provided in Table 2 below.

TABLE 2

| Electron Buffer Layer | Voltage (V) (10 $mA/cm^2$) | Voltage (V) (100 $mA/cm^2$) |
| --- | --- | --- |
| — | 3.6 | 5.2 |
| BF-1 | 4.3 | 5.7 |
| B-66 | 3.8 | 5.3 |
| B-102 | 3.8 | 5.3 |
| B-30 | 3.9 | 5.4 |

From Table 2 above, it can be seen that the devices comprising the compounds of the present invention in an electron buffer layer showed similar electron current property to the device having no electron buffer layer. Although the electron buffer layer of Comparative Example 2 had similar LUMO energy value to the compounds of the present invention, it had poor driving voltage. These results are conformity with driving voltage tendency of devices and if the compound having rapid electron current property is used in an electron buffer layer, if inserted, the devices have the merit of improvement of driving voltage and efficiency.

Comparative Example 3: Production of a Blue Light-Emitting OLED Device which does not Comprise an Electron Buffer Layer According to the Present Invention In Comparative Example 3, an OLED device was produced and evaluated in the same manner as in Comparative Example 1, except that compound HT-2 was replaced with compound HT-3, and compound ETL-1 was replaced with compound ETL-2.

The driving voltage at a luminance of 1,000 nit, emitted wavelength, and the lifespan time taken to be reduced from 100% to 90% of the luminance at 2,000 nit and a constant current of the OLED device produced in Comparative Example 3 are as provided in Table 3 below.

Device Examples 7 and 8: Production of a Blue Light-Emitting OLED Device According to the Present Invention In Device Examples 7 and 8, OLED devices were produced and evaluated in the same manner as in Comparative Example 3, except that the thickness of the electron transport layer was 30 nm and an electron buffer layer having a thickness of 5 nm was inserted between the light-emitting layer and the electron transport layer. The evaluation results of the devices of Device Examples 7 and 8 are as provided in Table 3 below.

TABLE 3

| | Electron Buffer Layer | Voltage (V) | Emitted Wavelength (nm) | Lifespan (hr) |
| --- | --- | --- | --- | --- |
| Comparative Example 3 | — | 4.2 | 456 | 41.8 |
| Device Example 7 | B-105 | 4.3 | 456 | 68.0 |
| Device Example 8 | B-68 | 4.5 | 456 | 52.6 |

As shown from Table 3 above, the electron buffer materials of Device Examples 7 and 8, which are benzoimidazole based compounds, showed excellent lifespan while having similar efficiency to Comparative Example 3 having no electron buffer layer due to having relatively slow but more suitable electron current characteristic than the results of Device Examples 1 to 5 using benzoxazole and benzothiazole based compounds. It can be seen that the compounds of the present invention contribute to the electron current characteristic in order of electronegativity. Thus, fast electron current characteristic is shown in order of O (oxygen), S (sulfur), and N (nitrogen). Therefore, compounds comprising oxygen or sulfur can provide high efficiency through relatively fast electron current characteristic. Whereas, compounds comprising nitrogen contribute to long lifespan by maintaining more suitable electron current characteristic due to electronegativity.

It is obvious that the organic EL compounds according to the present invention have excellent luminous property compared with conventional materials. Furthermore, a device comprising the organic EL compounds according to the present invention in an electron buffer layer shows excellent luminous property and lowers driving voltage, thereby enhancing power efficiency and improving consumer power and shows improved lifespan.

TABLE 4

Compounds used in Comparative Examples and Device Examples

| Hole Injection Layer/ Hole Transport Layer | HI-1 | HI-2 | HT-1 | HT-2 |

TABLE 4-continued
Compounds used in Comparative Examples and Device Examples
HT-3
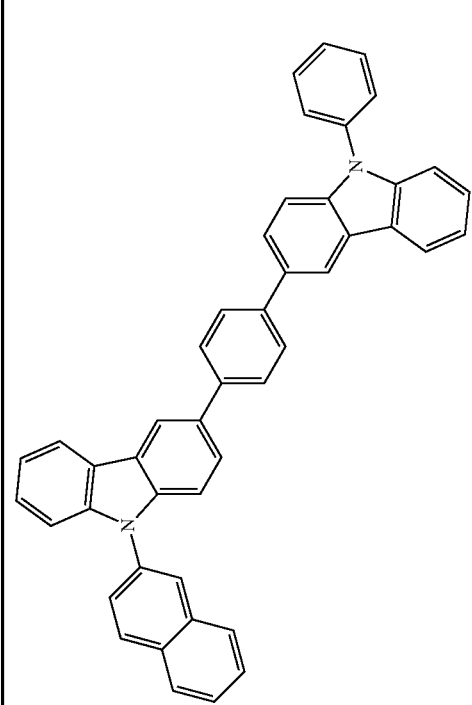
BD-1
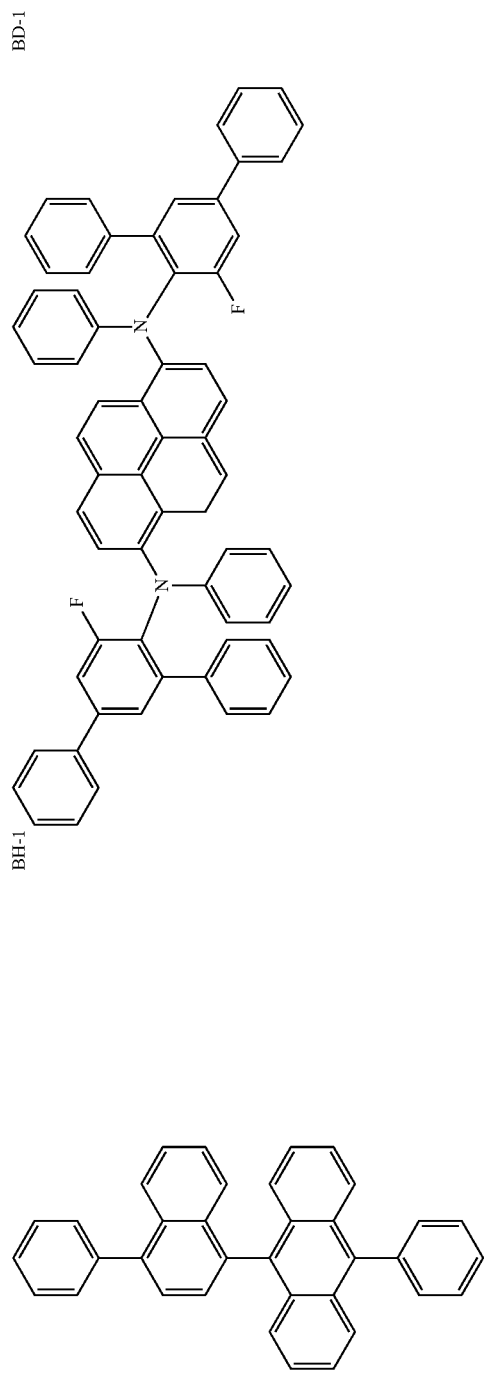
BH-1
Light-Emitting Layer TABLE 4-continued Compounds used in Comparative Examples and Device Examples

| Electron Buffer Layer | BF-1 | B-72 |
| --- | --- | --- |
| | B-7 | B-66 |

TABLE 4-continued
Compounds used in Comparative Examples and Device Examples
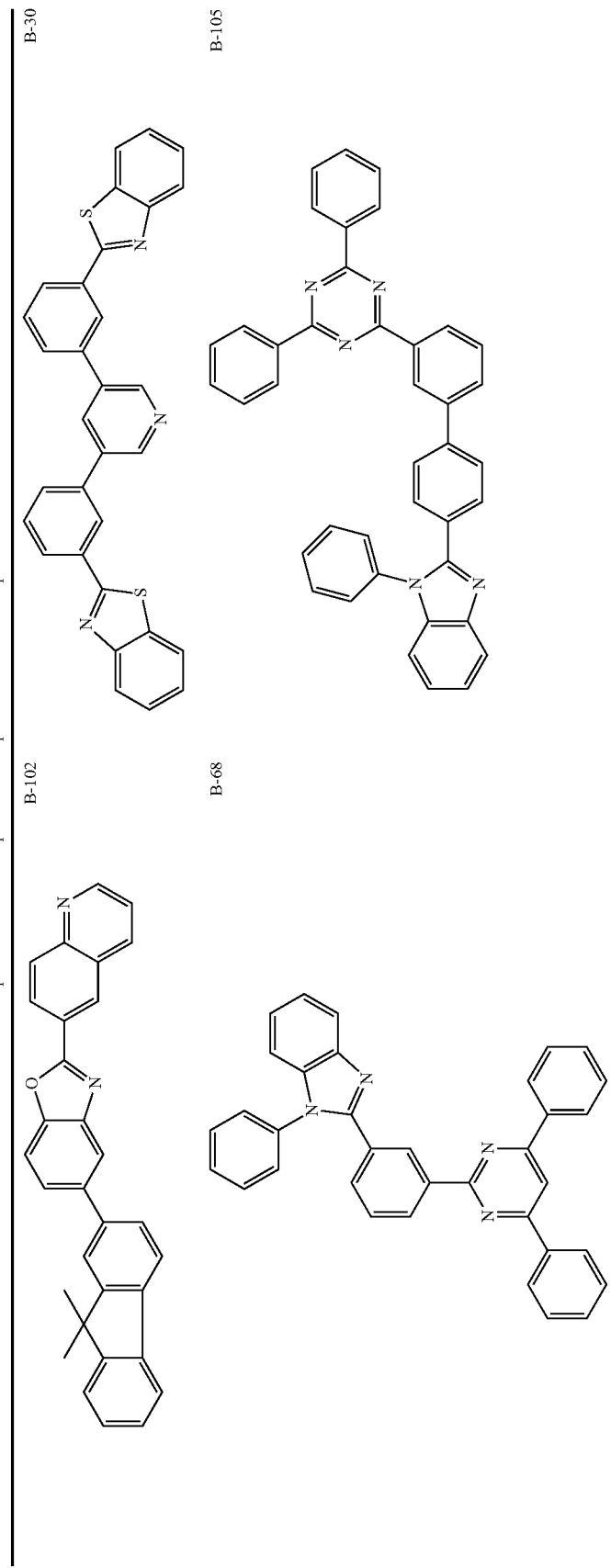

TABLE 4-continued
Compounds used in Comparative Examples and Device Examples
| | | |
|---|---|---|
| Electron Transport Layer/ Electron Injection Layer | ETL-1 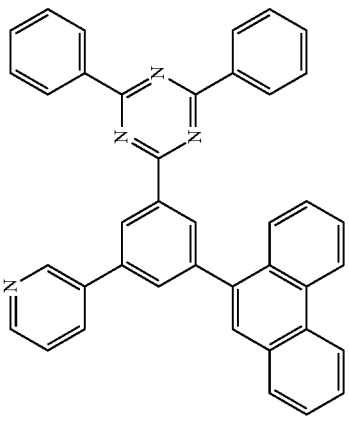 | ETL-2 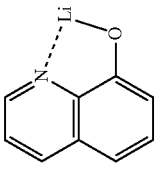<br><br>EIL-1 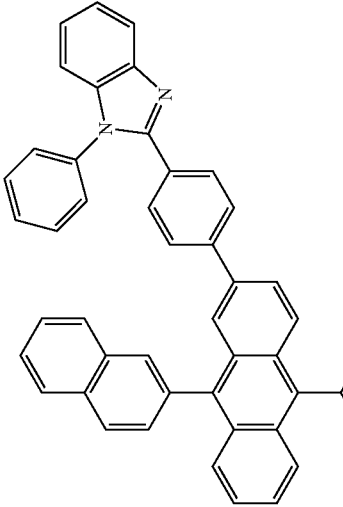 |

DESCRIPTION OF REFERENCE NUMBERS

| | |
|---|---|
| 100: Organic EL Device | 101: Substrate |
| 110: First Electrode | 120: Organic Layer |
| 122: Hole Injection Layer | 123: Hole Transport Layer |
| 125: Light-Emitting Layer | 126: Electron Buffer Layer |
| 127: Electron Transport Layer | 128: Electron Injection Layer |
| 129: Electron Transport Zone | 130: Second Electrode |

The invention claimed is:

1. An electron buffer material selected from the group consisting of the following compounds:

B-1
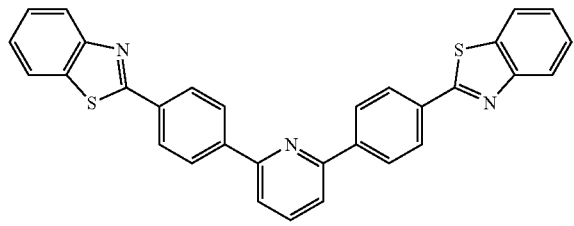

B-2
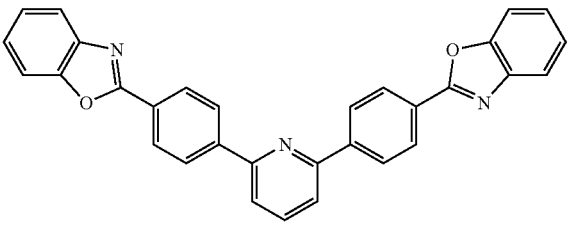

B-3
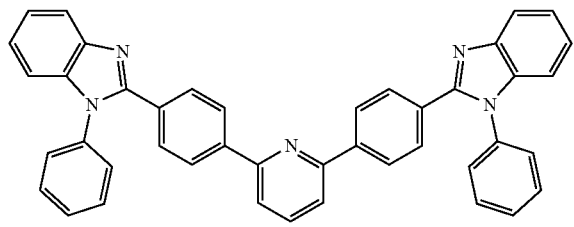

B-4
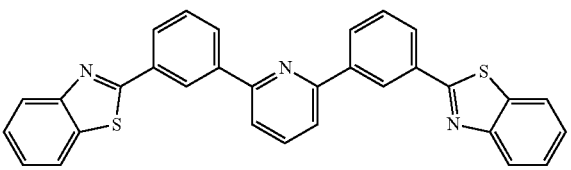

B-5
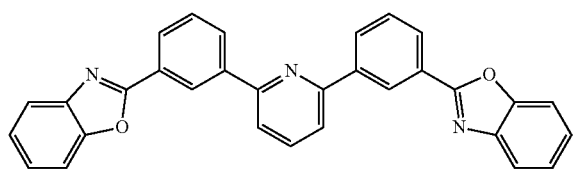

B-6
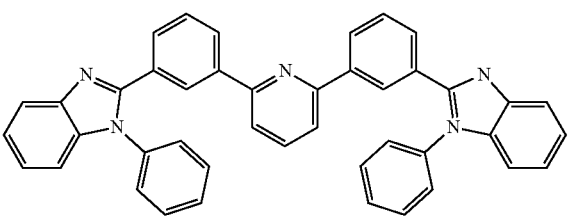

B-7
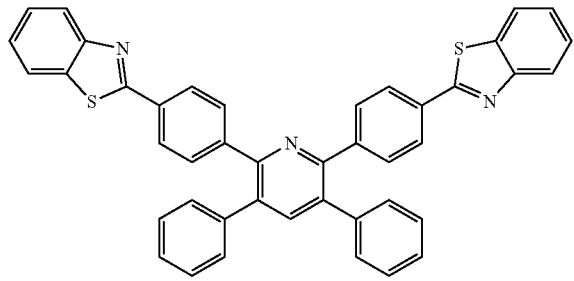 [SMILES: c1ccc(-c2cc(-c3ccccc3)c(-c3ccc(-c4nc5ccccc5s4)cc3)nc2-c2ccc(-c3nc4ccccc4s3)cc2)cc1]

B-8
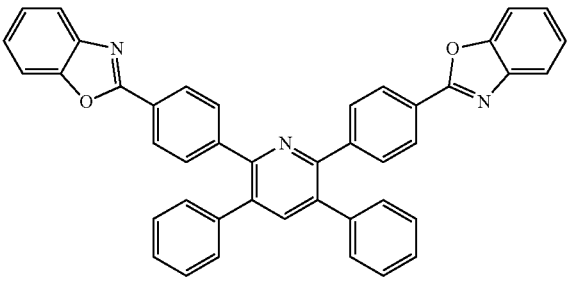

B-9
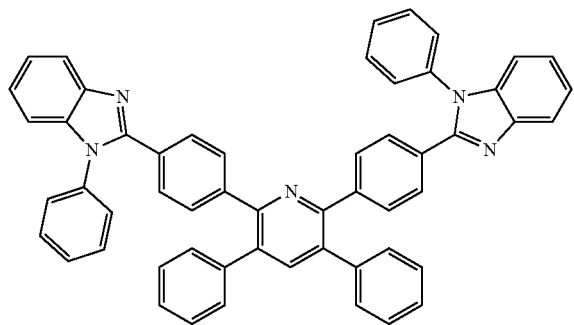

B-10
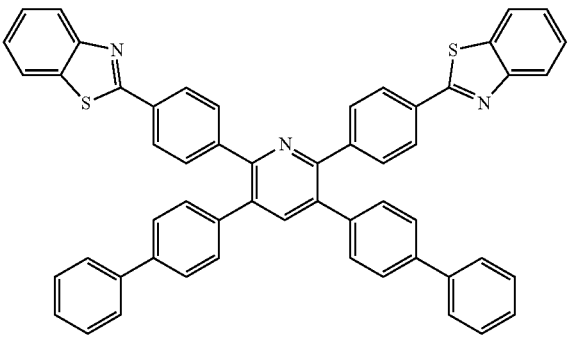

-continued
B-11
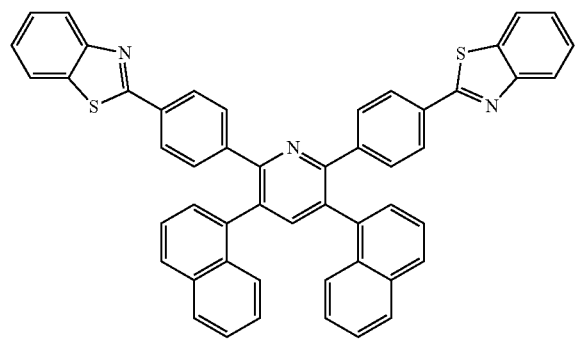
B-12
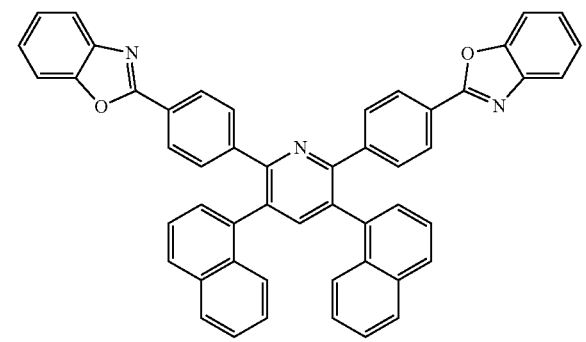
B-13
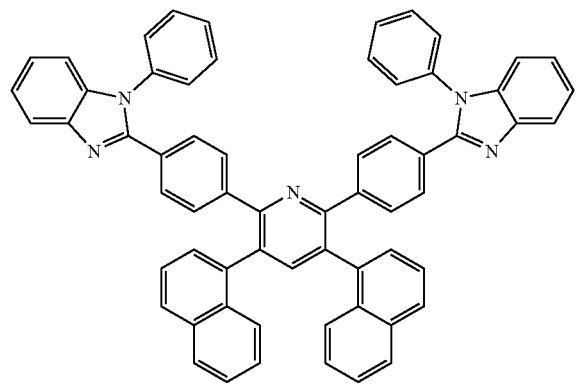
B-14
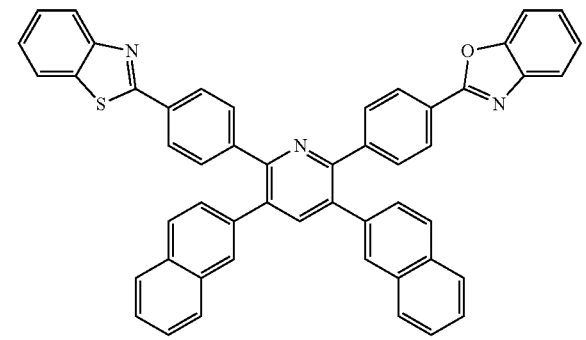
B-15
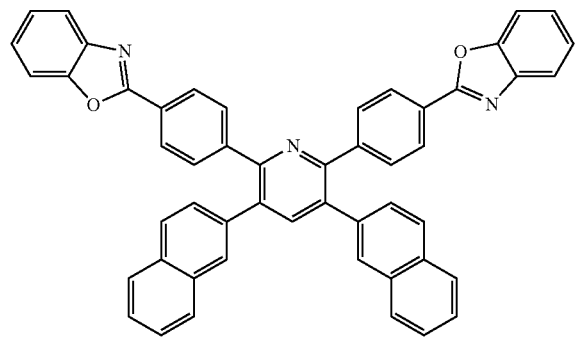
B-16
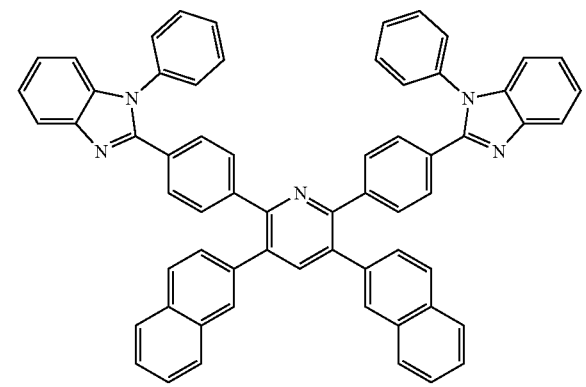
B-17
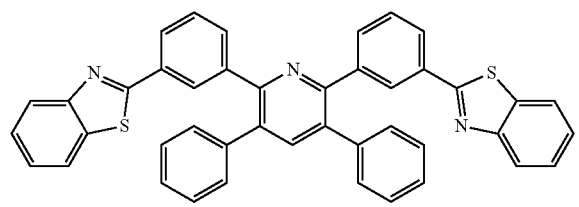
B-18
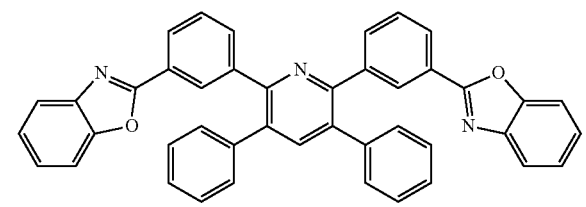

-continued
B-19
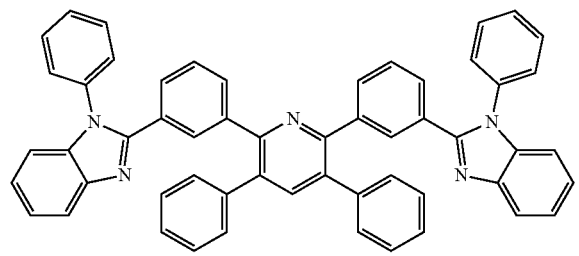
B-20
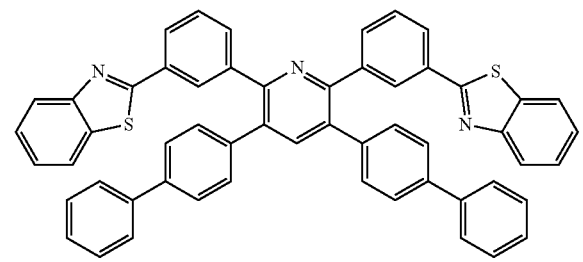
B-21
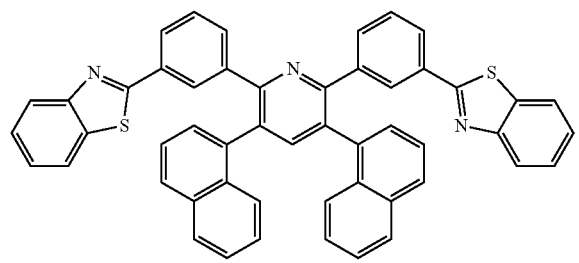
B-22
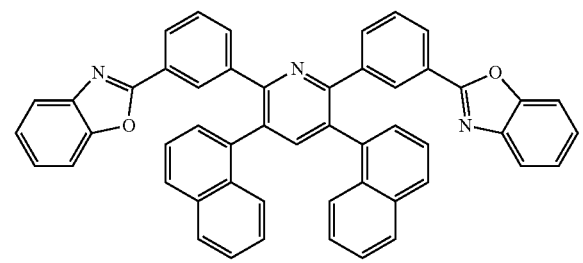
B-23
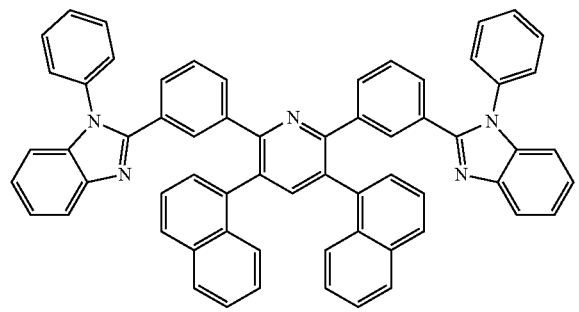
B-24
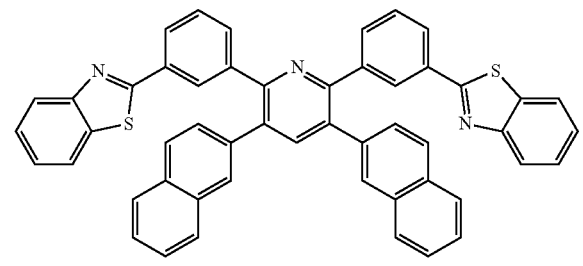
B-25
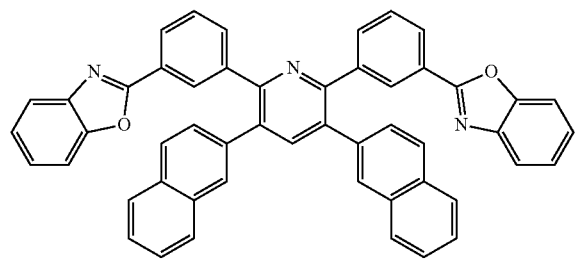
B-26
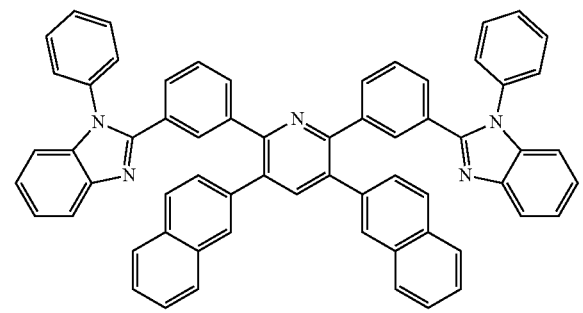
B-27
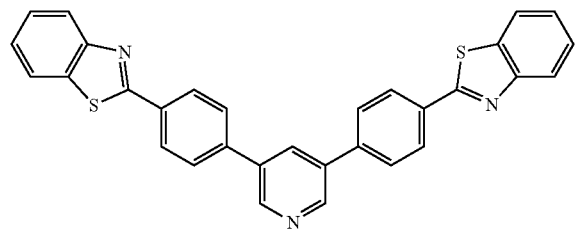
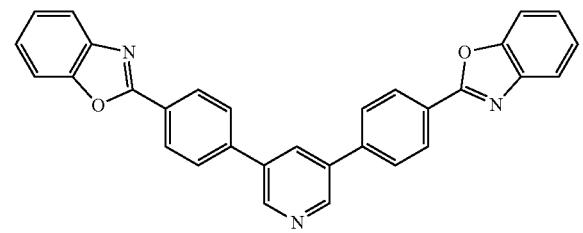

-continued
B-29
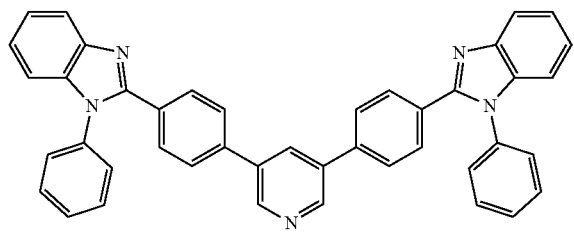
B-30
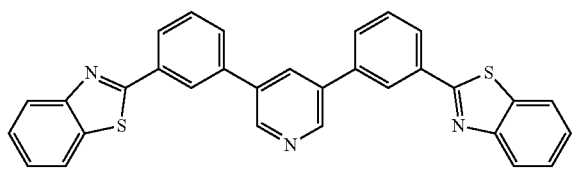
B-31
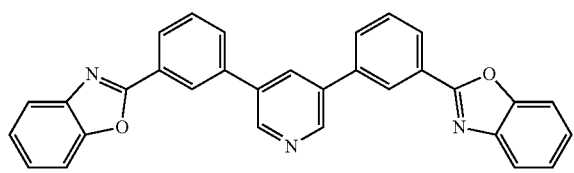
B-32
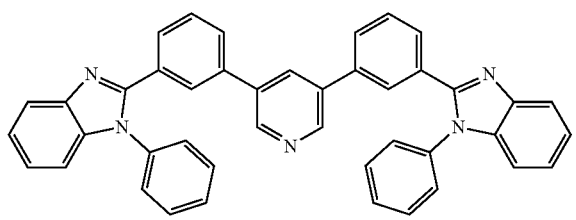
B-33
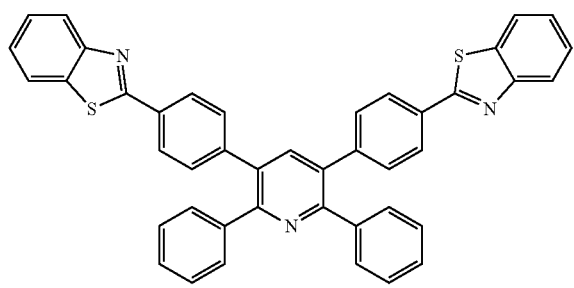
B-34
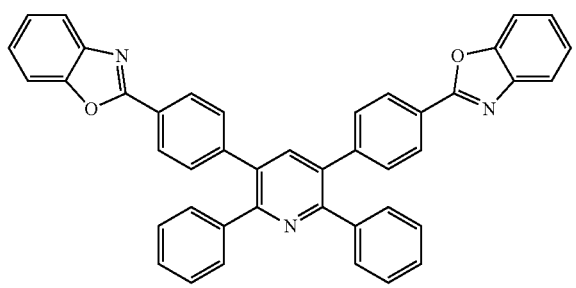
B-35
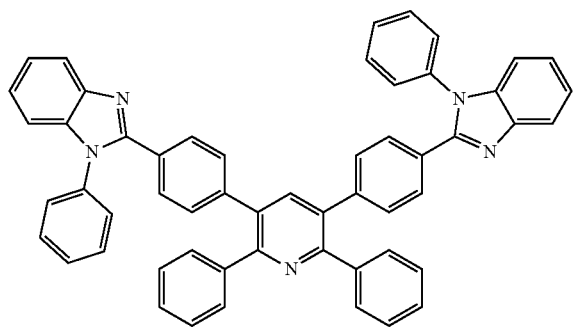
B-36
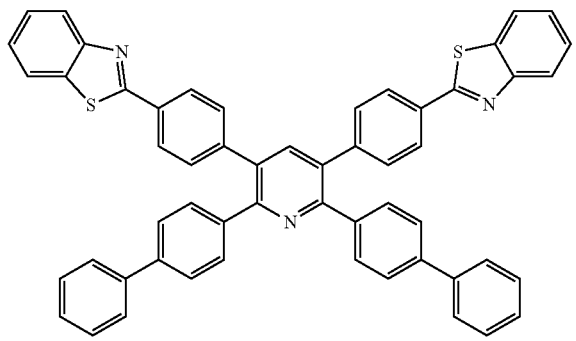
B-37
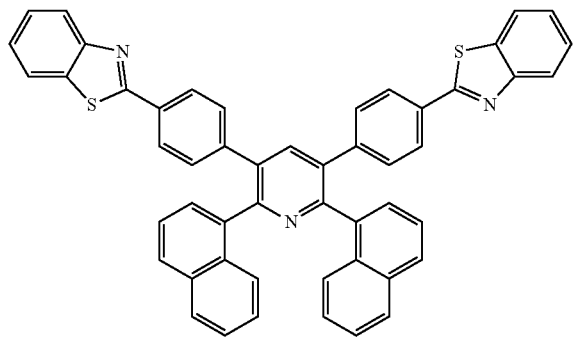
B-38
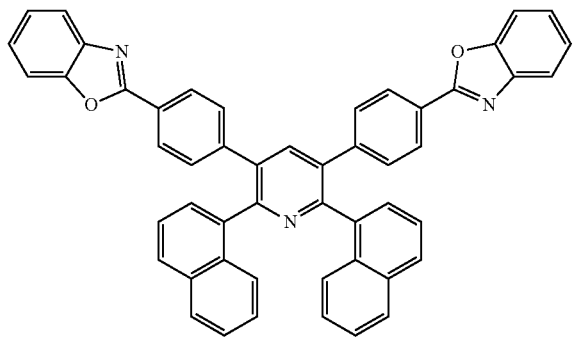

-continued
B-39
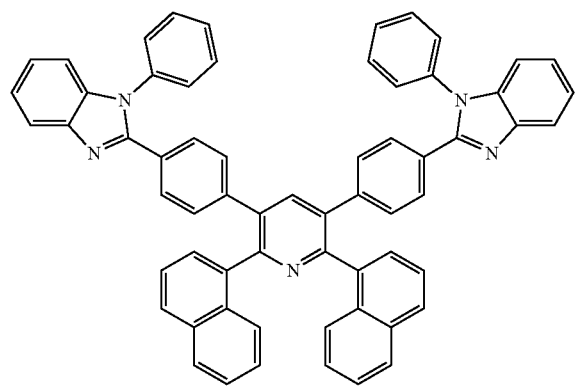
B-40
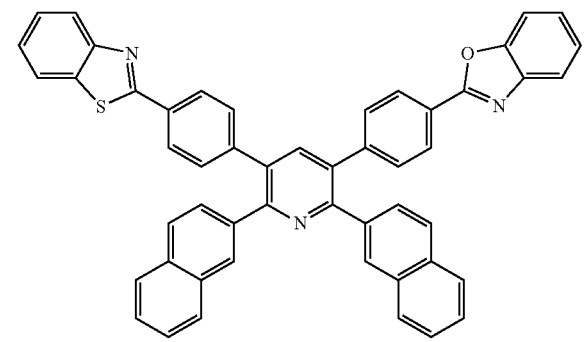
B-41
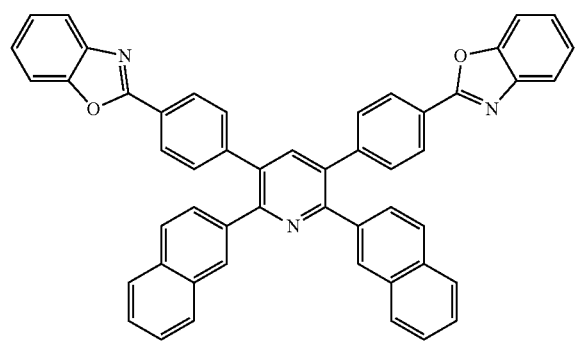
B-42
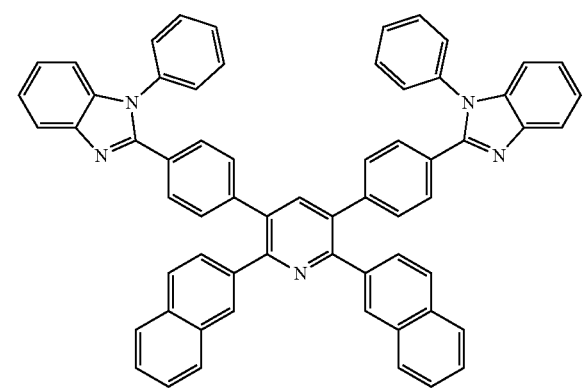
B-43
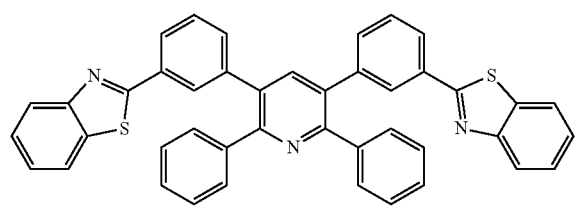
B-44
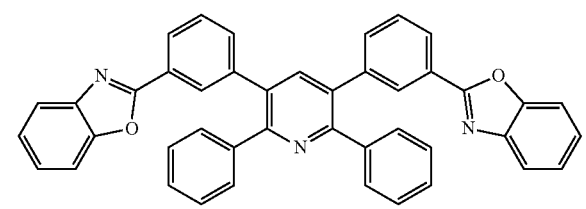
B-45
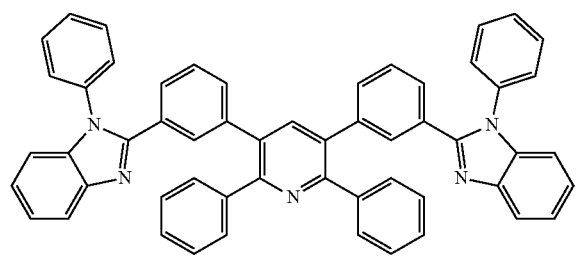
B-46
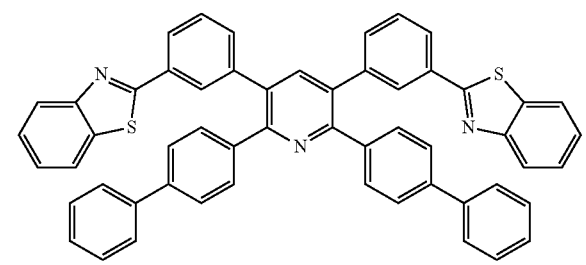
B-47
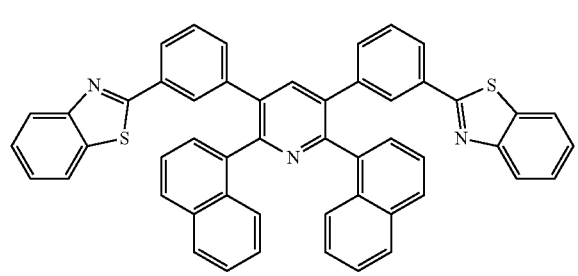
B-48
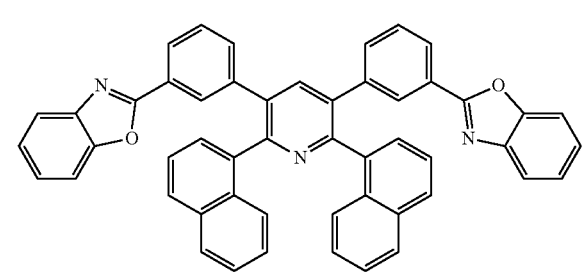

-continued
B-49
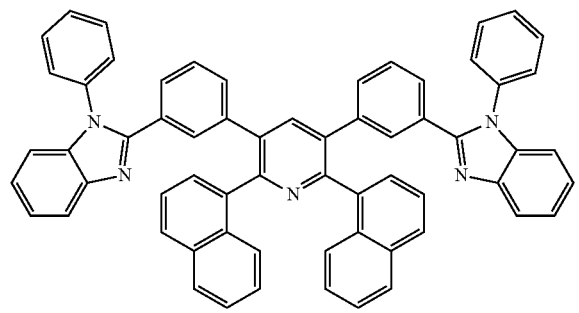
B-50
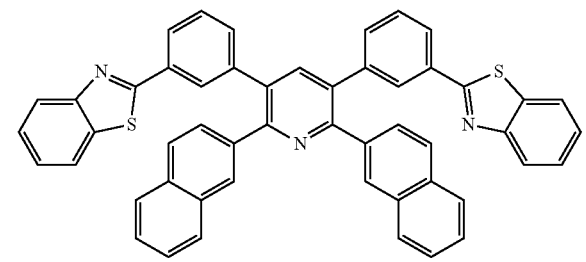
B-51
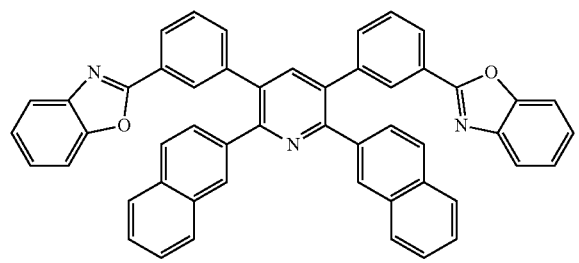
B-52
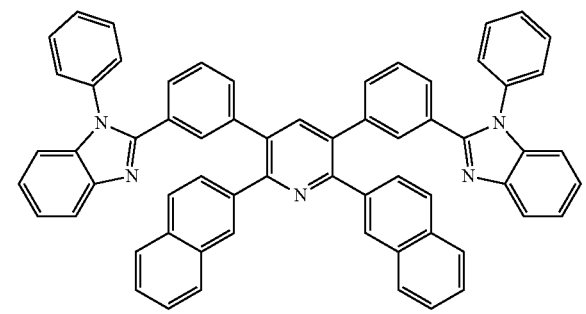
B-53
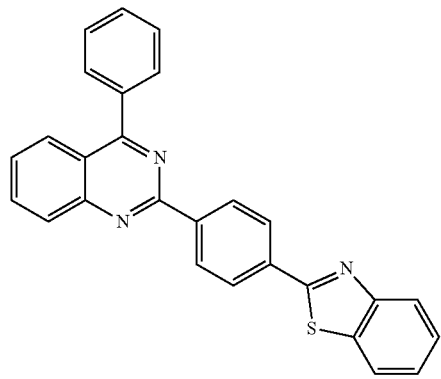
B-54
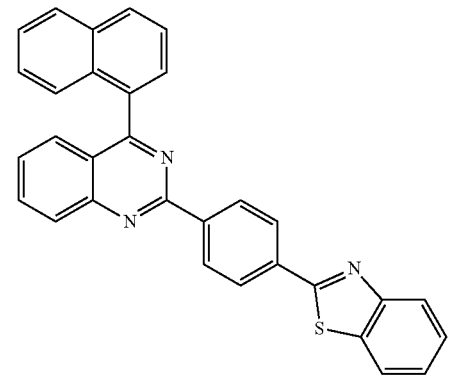
B-55
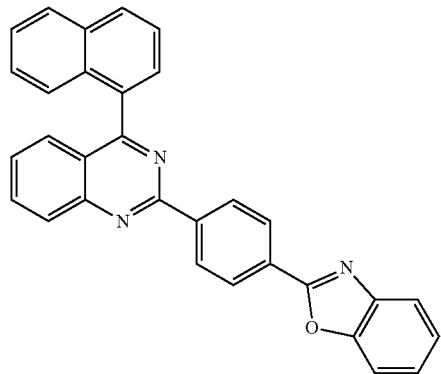
B-56
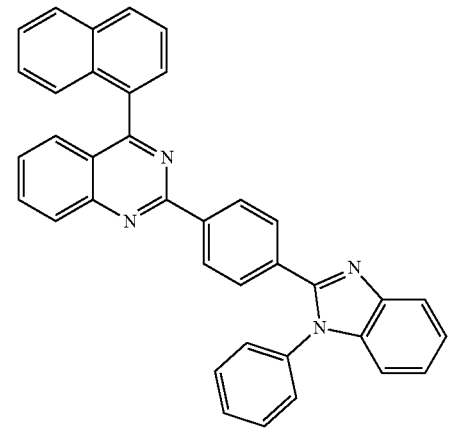

B-57
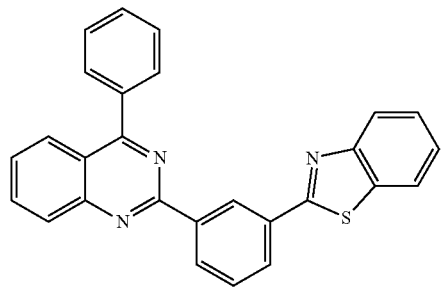
B-58
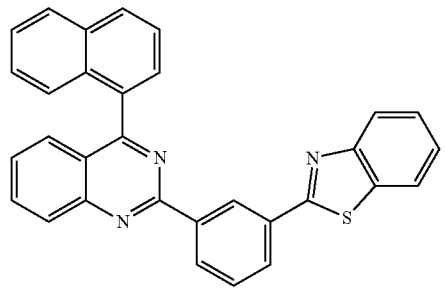
B-59
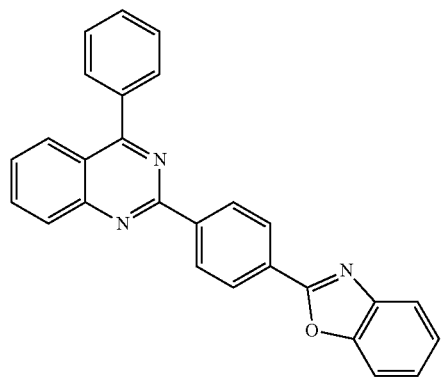
B-60
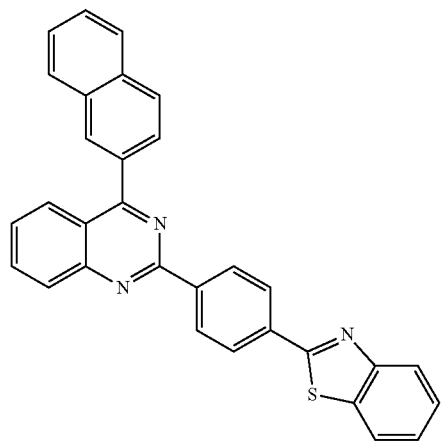
B-61
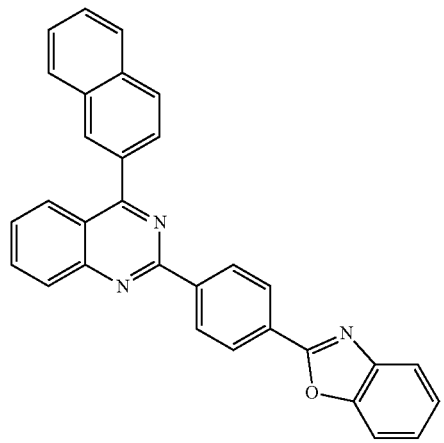
B-62
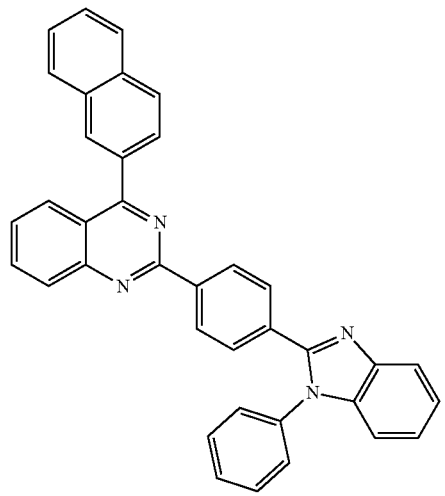
B-63
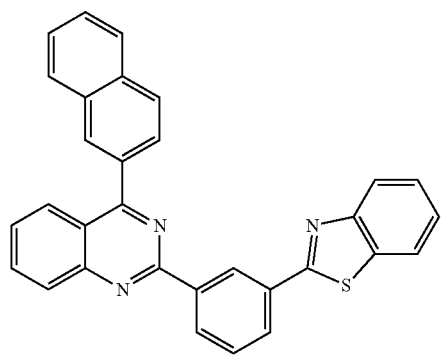
B-64
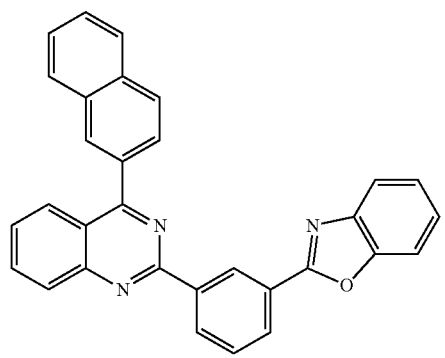

-continued
B-65
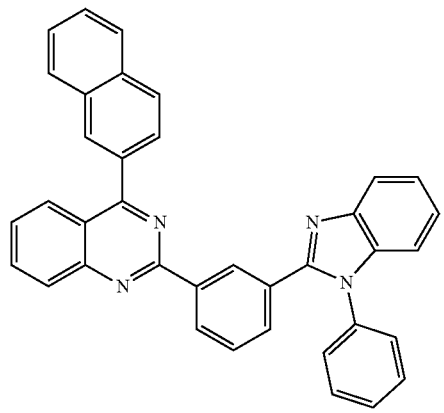
B-66
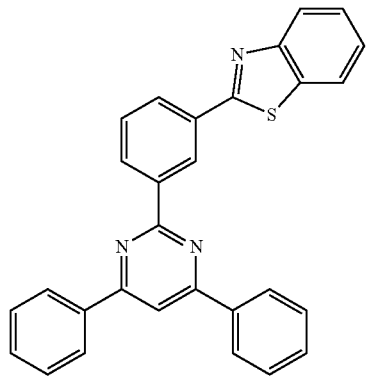 [SMILES: c1ccc(-c2cc(-c3ccccc3)nc(-c3cccc(-c4nc5ccccc5s4)c3)n2)cc1]
B-67
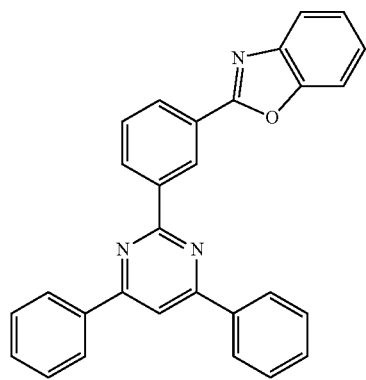
B-68
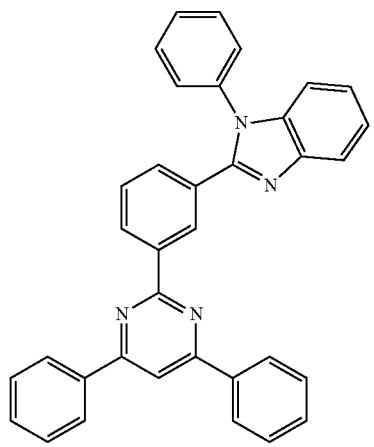
B-69
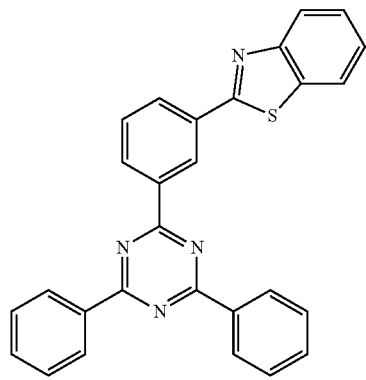
B-70
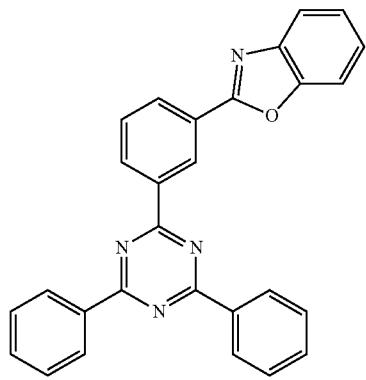

-continued
B-71
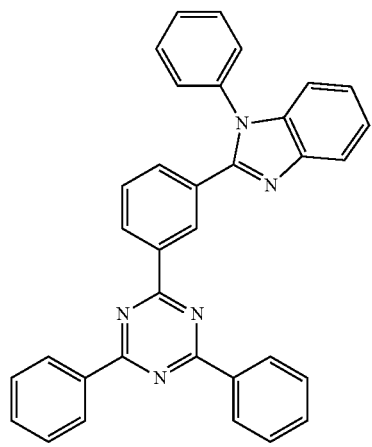
B-72
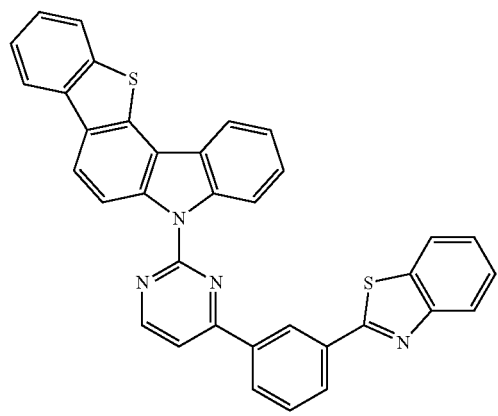
B-73
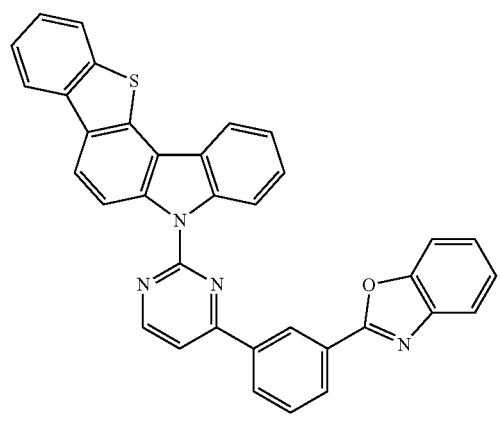
B-74
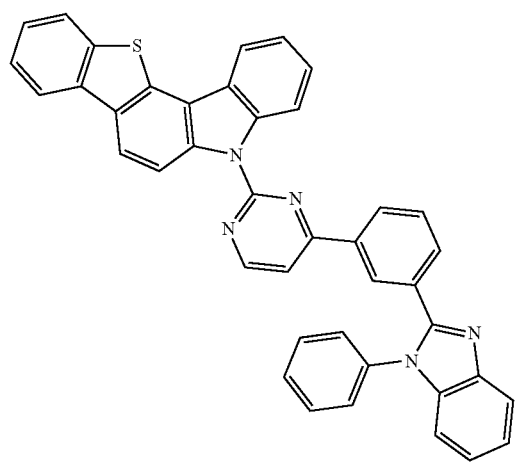
B-75
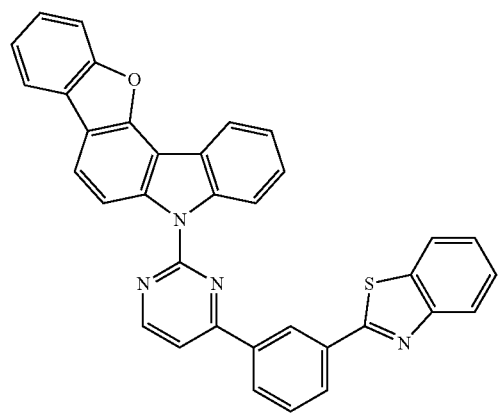
B-76
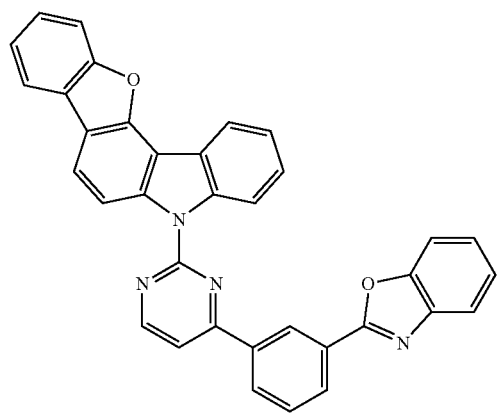

-continued
B-77
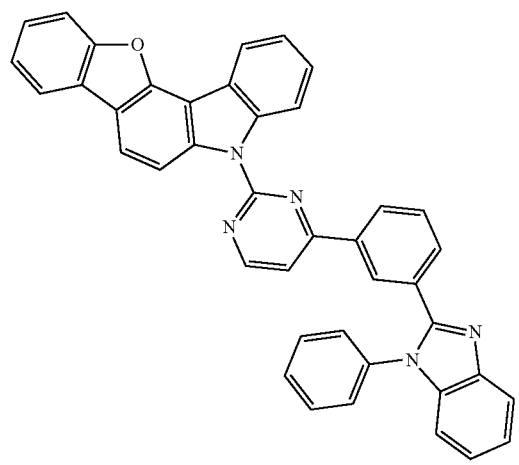
B-78
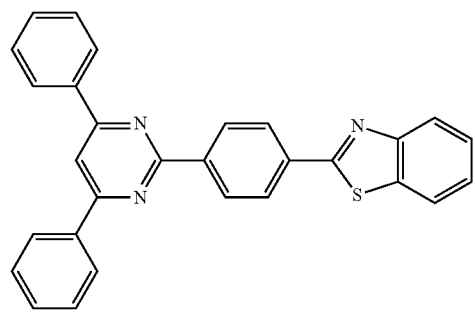
B-79
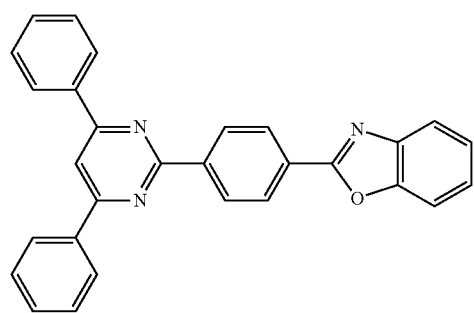
B-80
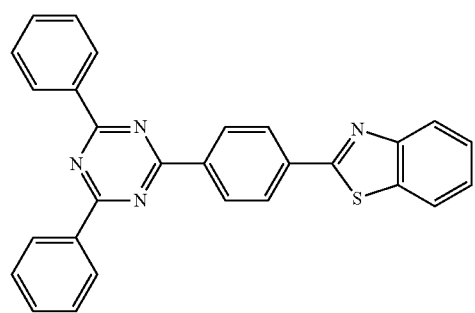
B-81
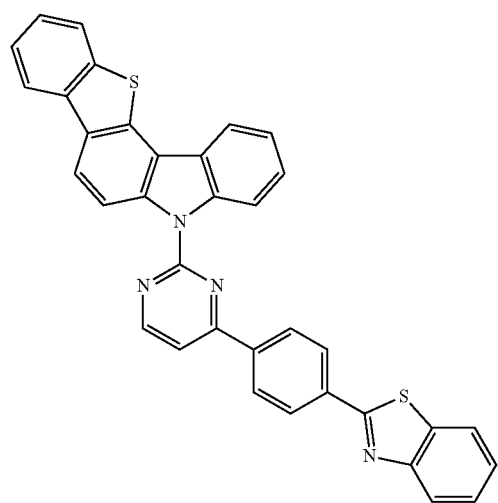
B-82
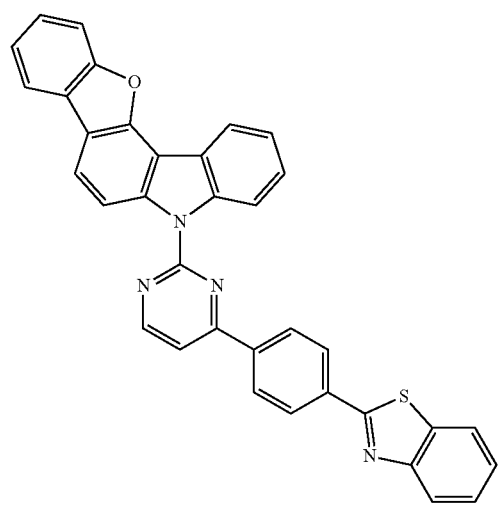

B-83
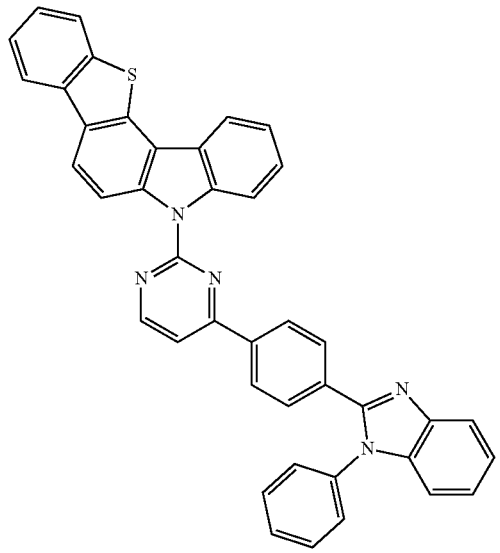
B-84
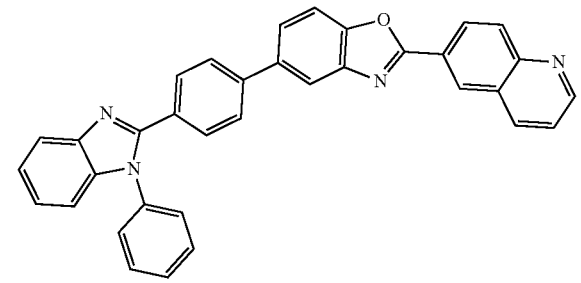
B-85
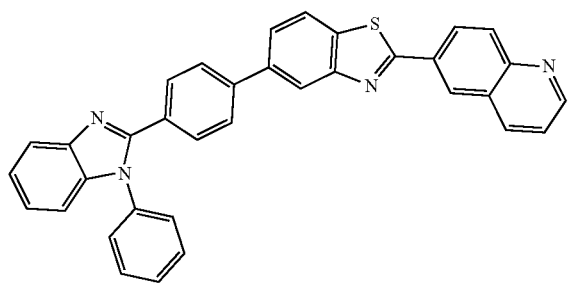
B-86
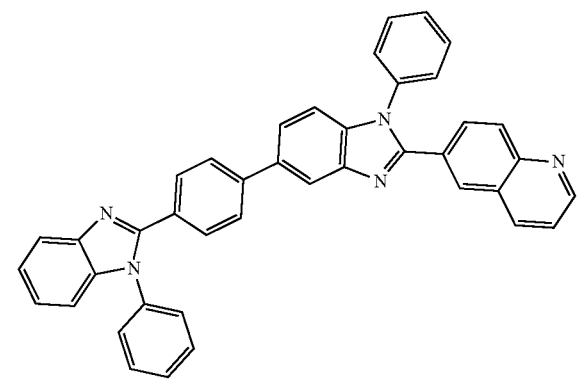
B-87
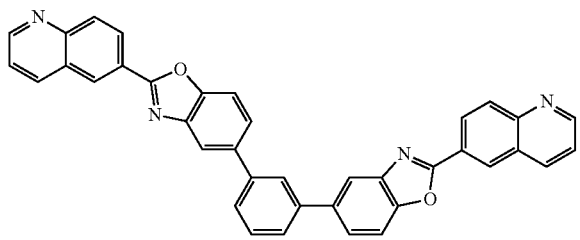
B-88
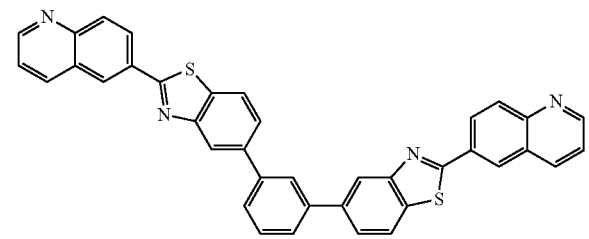
B-89
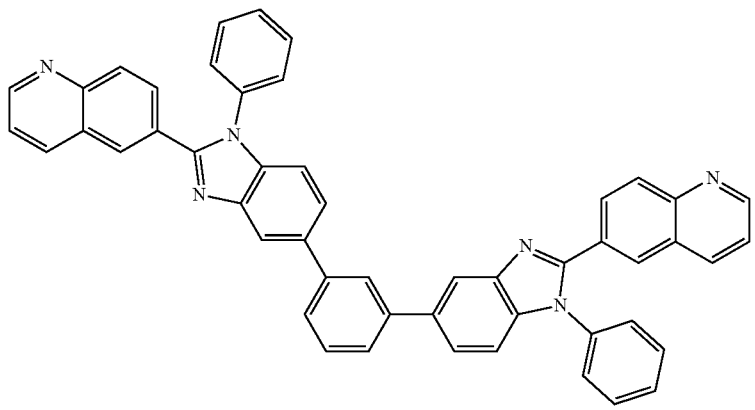

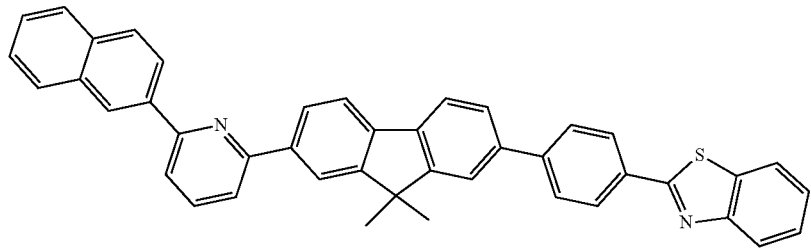
B-90
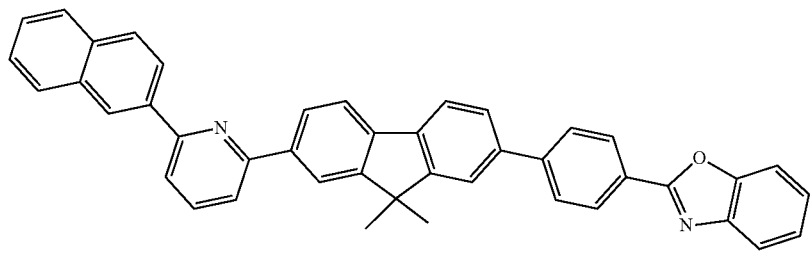
B-91
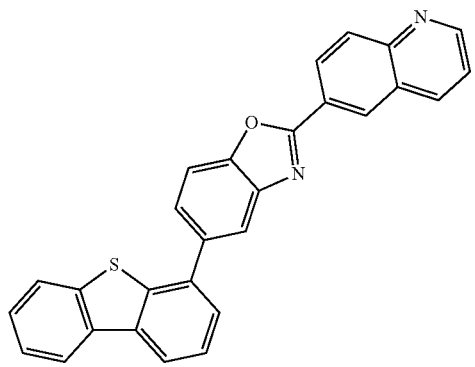
B-92
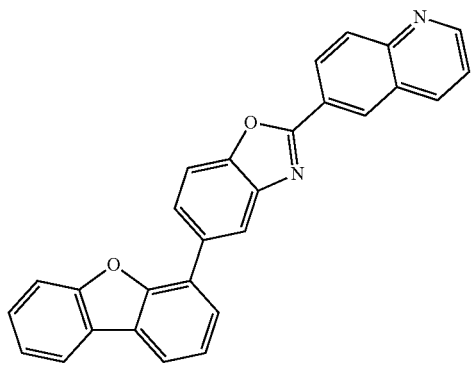
B-93
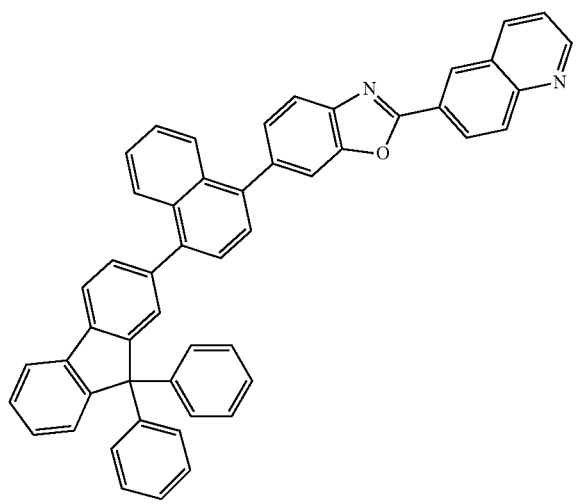
B-94
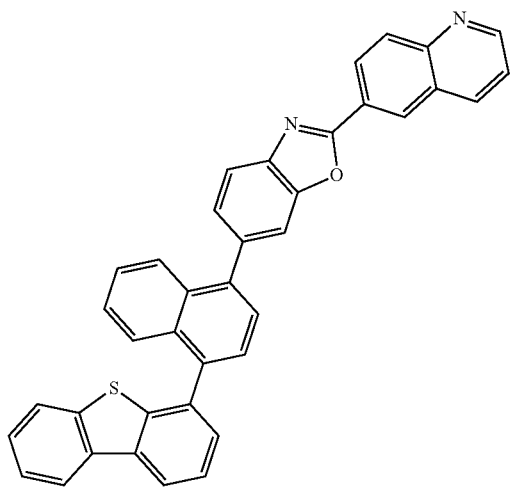
B-95

B-96
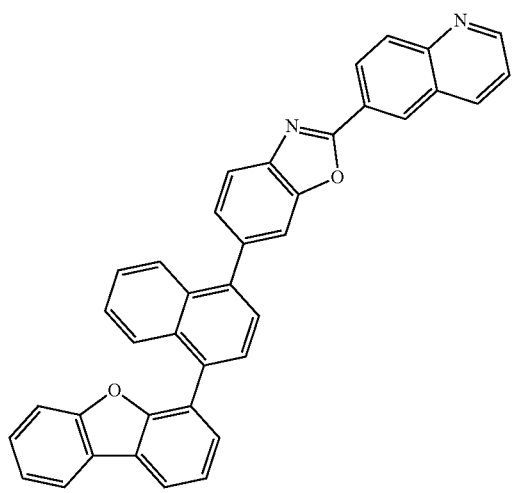
B-97
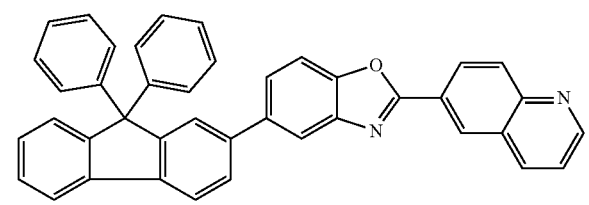
B-98
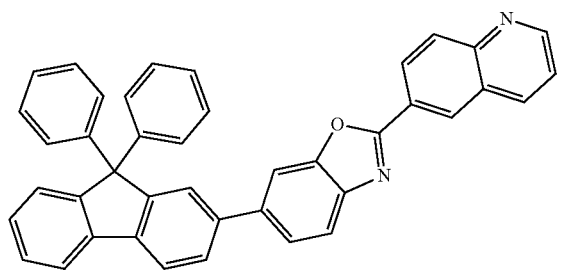
B-99
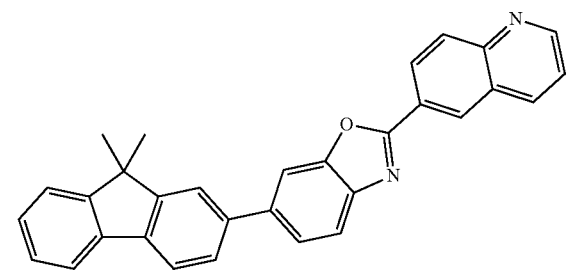
B-100
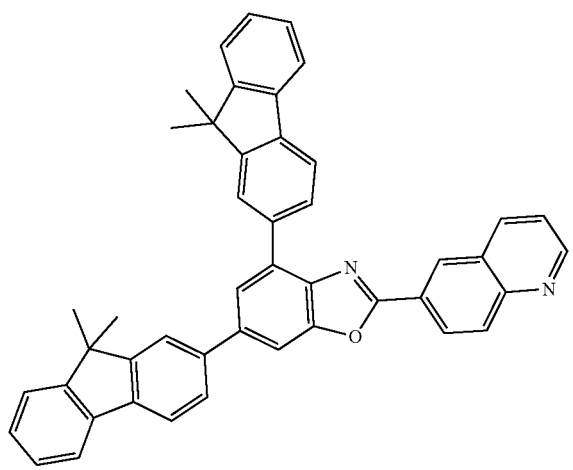
B-101
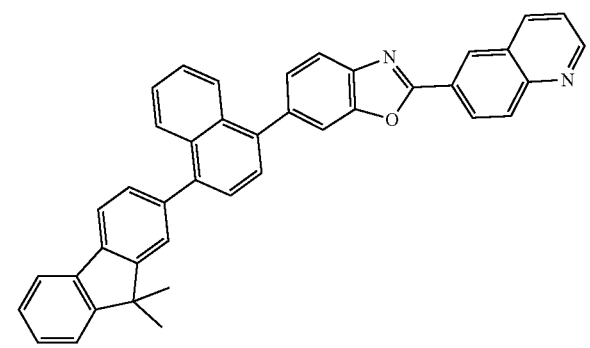
B-102
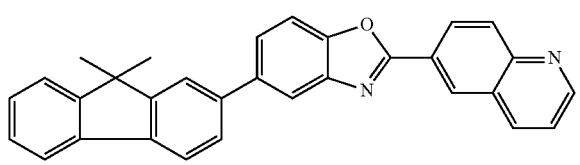 [SMILES: CC1(C)c2ccccc2-c2ccc(-c3ccc4oc(-c5ccc6ncccc6c5)nc4c3)cc21]
B-103
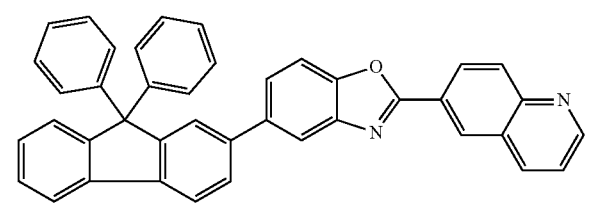

-continued
B-104
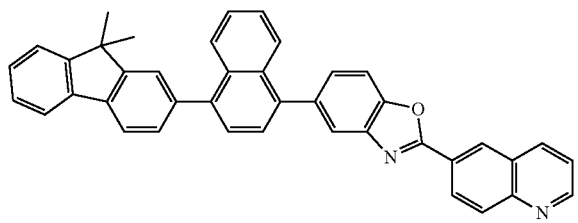
B-105
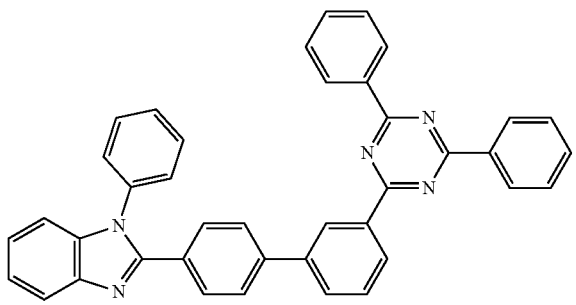
B-106
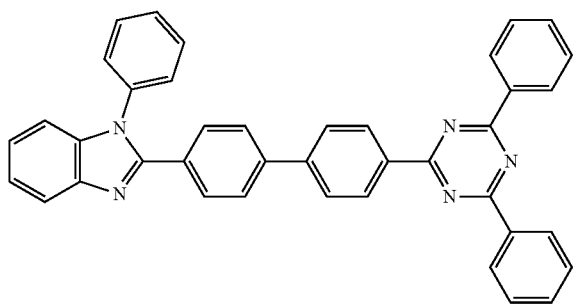
B-107
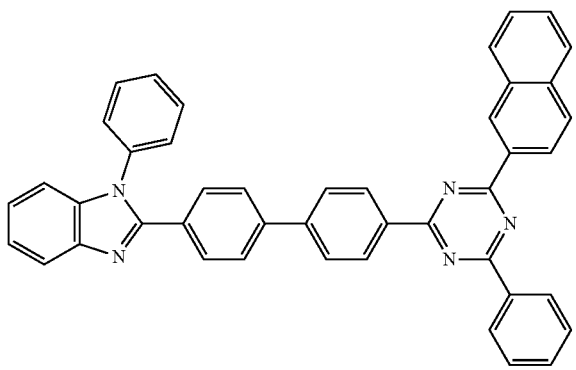
B-108
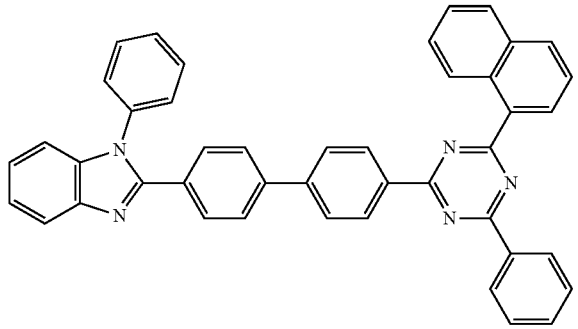
B-109
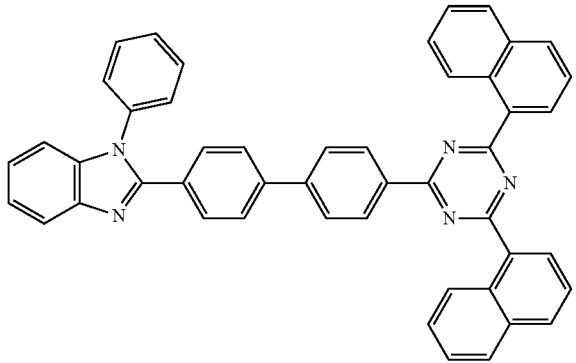
B-110
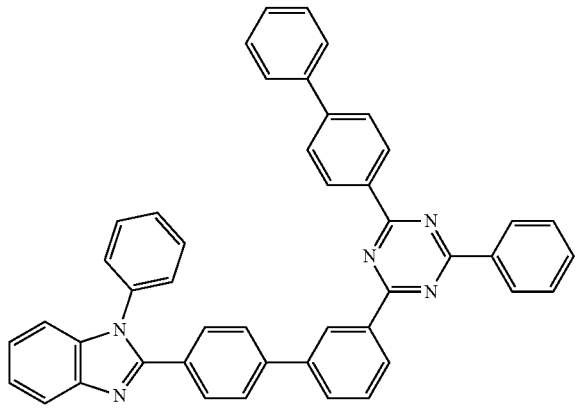
B-111
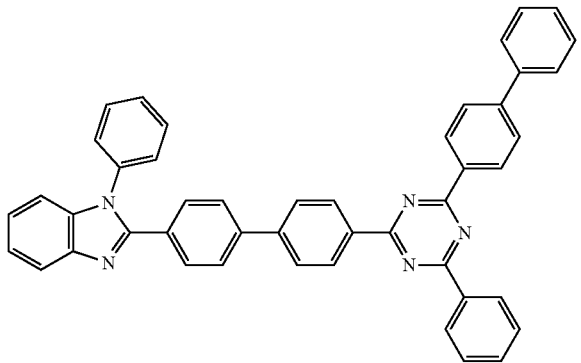

-continued
B-112
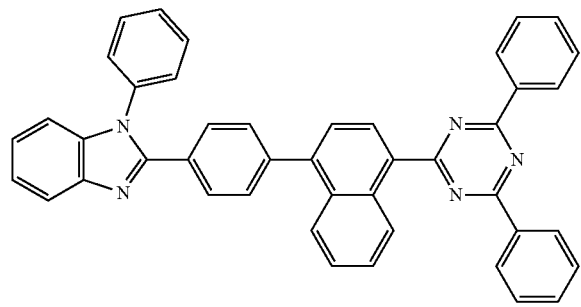
B-113
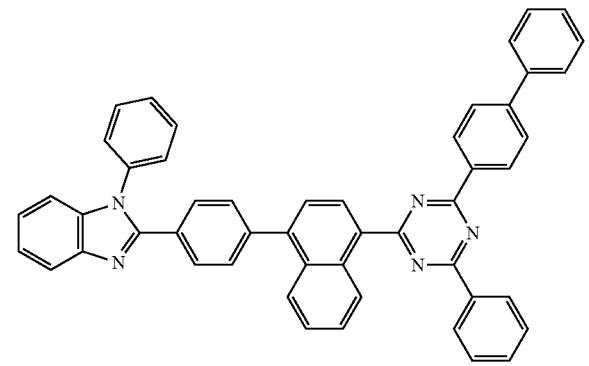
B-114
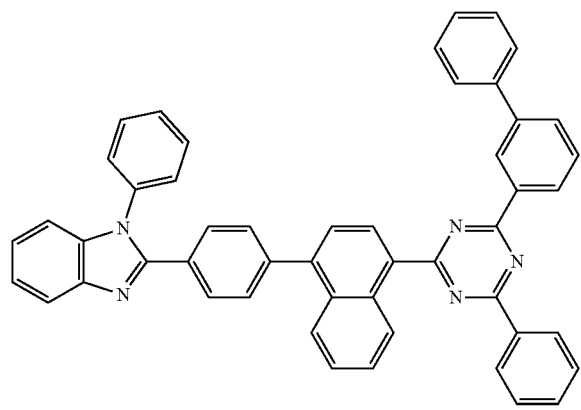
B-115
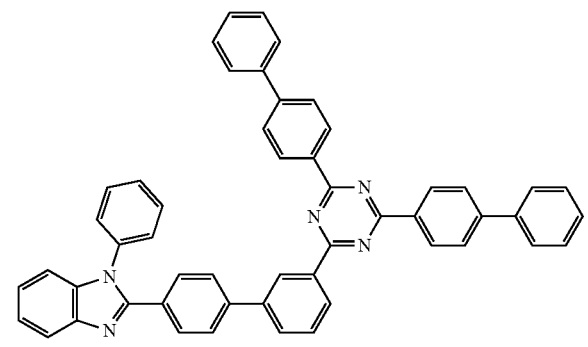
B-116
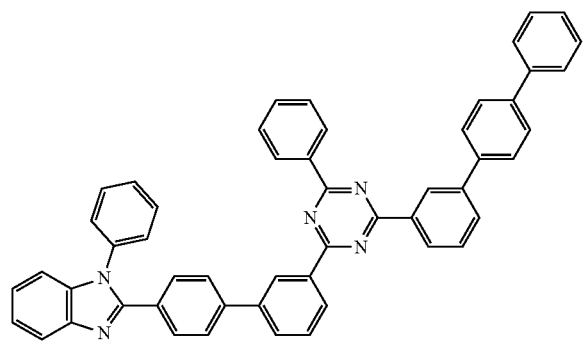
B-117
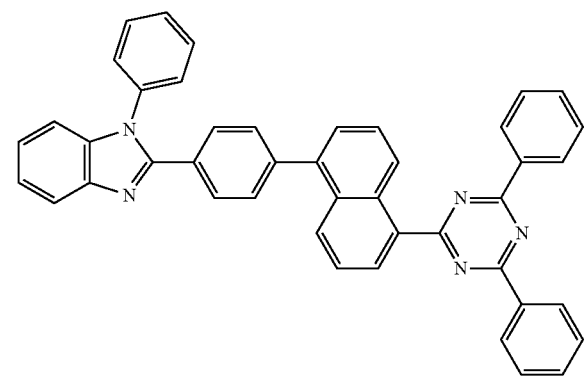
B-118
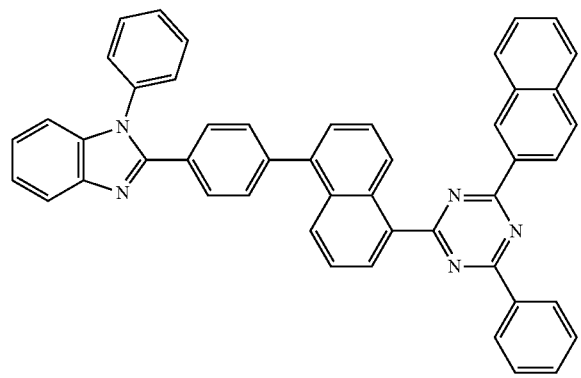
B-119
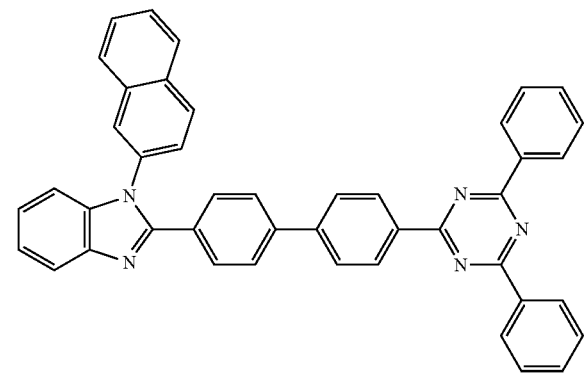

-continued
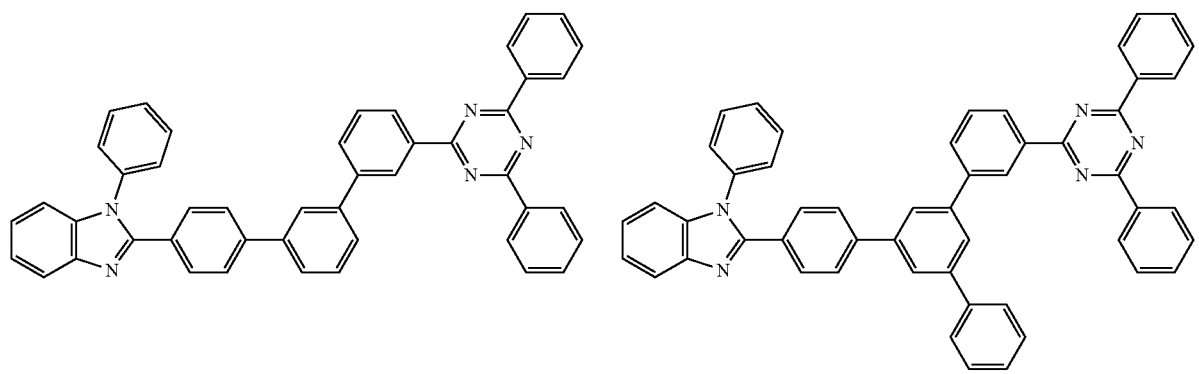
B-120    B-121
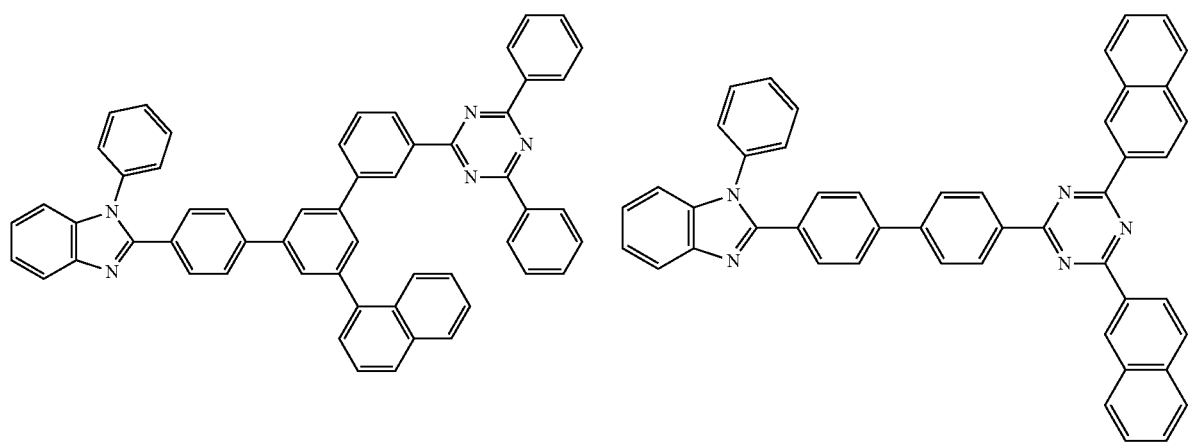
B-122    B-123
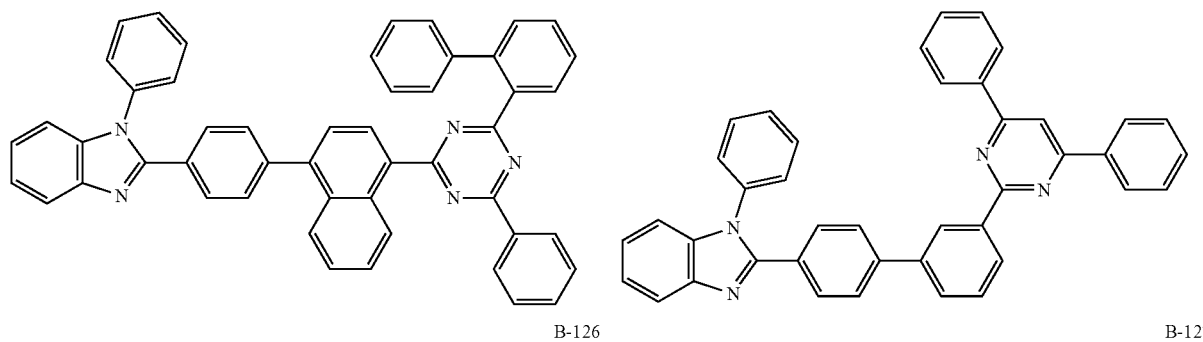
B-124    B-125
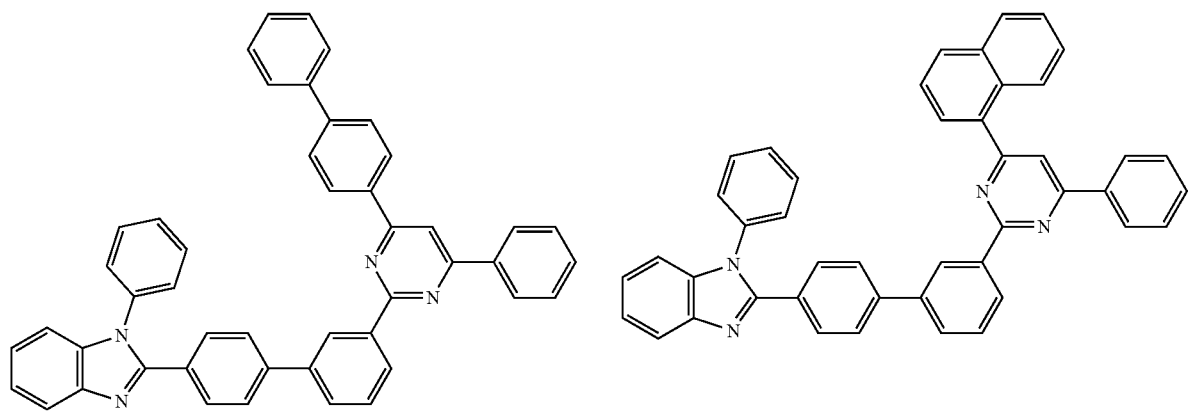
B-126    B-127

B-128

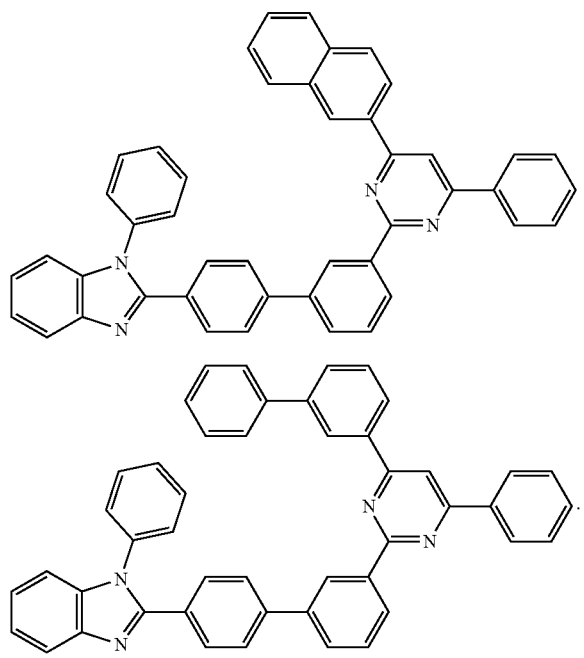

B-129

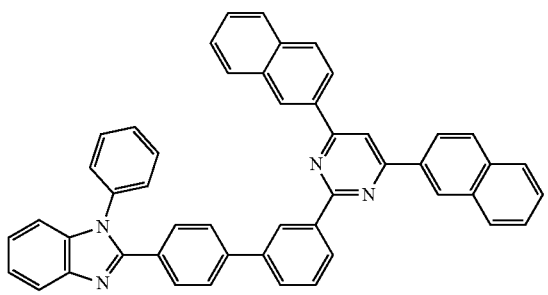

and

B-130

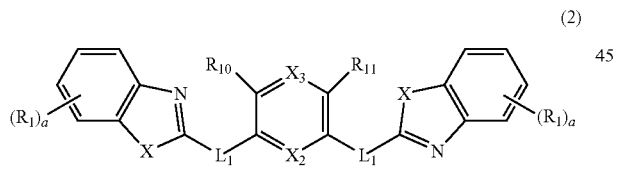

2. An organic electroluminescent device comprising a first electrode, a second electrode opposing the first electrode, a light-emitting layer disposed between the two electrodes, and an electron transport zone and an electron buffer layer disposed between the light-emitting layer and the second electrode, wherein the electron transport zone comprises an electron injection layer and an electron transport layer, wherein the electron buffer layer comprises the compound represented by the following formula 2 or 5:

(2)

(5)

wherein $X_2$ represents N or $CR_8$;

$X_3$ represents N or $CR_9$;

with the proviso that when $X_2$ represents N, $X_3$ represents $CR_9$, and if $X_2$ represents $CR_8$, $X_3$ represents N;

$R_8$ and $R_9$ each independently represent hydrogen or deuterium;

$L_1$ represents a single bond, an unsubstituted (C6-C30) arylene group, or an unsubstituted 3- to 30-membered heteroarylene group;

X represents O, S, or $NR_2$;

$R_1$, $R_2$ and $R_{14}$ each independently represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted 3- to 7-membered heterocycloalkyl group, a substituted or unsubstituted (C6-C30)aryl group, a substituted or unsubstituted 3- to 30-membered heteroaryl group, $-NR_3R_4$, or $-SiR_5R_6R_7$; or are linked to an adjacent substituent(s) to form a substituted or unsubstituted mono- or polycyclic (C3-C30) alicyclic or aromatic ring whose carbon atom(s) may be replaced with at least one hetero atom selected from nitrogen, oxygen, and sulfur;

$R_3$ to $R_7$, $R_{10}$ and $R_{11}$ each independently represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted 3- to 7-membered heterocycloalkyl group, a substituted or unsubstituted (C6-C30) aryl group, or a substituted or unsubstituted 3- to 30-membered heteroaryl group;

a and c each independently represents an integer of 1 to 4; where a is an integer of 2 or more, each $R_1$ is the same or different; where c is an integer of 2 or more, each $R_{14}$ is the same or different; and the heteroaryl(ene) and heterocycloalkyl groups each independently contain at least one hetero atom selected from B, N, O, S, P(=O), Si, and P.

3. The organic electroluminescent device according to claim 2, wherein the light-emitting layer comprises a host compound and a dopant compound, and LUMO (lowest unoccupied molecular orbital) energy value of the electron buffer layer is higher than that of the host compound.

4. The organic electroluminescent device according to claim 2, wherein the electron transport zone comprises an electron transport compound, a reducing dopant, or the combination thereof.

5. The organic electroluminescent device according to claim 4, wherein the electron transport compound is at least one selected from the group consisting of oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes, and the reducing dopant is at least one selected from the group consisting of an alkaline metal, an alkaline metal compound, an alkaline earth metal, a rare-earth metal, halides thereof, oxides thereof, and complexes thereof.

6. The organic electroluminescent device according to claim 2, wherein a hole injection layer, a hole transport layer, or both of them are further included between the first electrode and the light-emitting layer.

7. The compound according to claim 2, wherein X represents $NR_2$.

8. The compound according to claim 2, wherein X represents O or S.

9. The compound according to claim 2, wherein the substituents of the substituted alkyl group, the substituted aryl(ene) group, the substituted heteroaryl(ene) group, the substituted cycloalkyl group, the substituted cycloalkenyl group, the substituted heterocycloalkyl group, or the substituted mono- or polycyclic (C3-C30) alicyclic or aromatic ring in formula 2 or 5 are each independently at least one selected from the group consisting of deuterium; a halogen; a cyano group; a carboxyl group; a nitro group; a hydroxyl group; a (C1-C30)alkyl group; a halo(C1-C30)alkyl group; a (C2-C30)alkenyl group; a (C2-C30)alkynyl group; a (C1-C30)alkoxy group; a (C1-C30)alkylthio group; a (C3-C30)cycloalkyl group; a (C3-C30)cycloalkenyl group; a 3- to 7-membered heterocycloalkyl group; a (C6-C30)aryloxy group; a (C6-C30)arylthio group; a 5- to 30-membered heteroaryl group which is unsubstituted or substituted with a (C6-C30)aryl group; a (C6-C30)aryl group which is unsubstituted or substituted with a 5- to 30-membered heteroaryl group; a tri(C1-C30)alkylsilyl group; a tri(C6-C30)arylsilyl group; a di(C1-C30)alkyl(C6-C30)arylsilyl group; a (C1-C30)alkyldi(C6-C30)arylsilyl group; an amino group; a mono- or di(C1-C30)alkylamino group; a mono- or di(C6-C30)arylamino group; a (C1-C30)alkyl(C6-C30)arylamino group; a (C1-C30)alkylcarbonyl group; a (C1-C30)alkoxycarbonyl group; a (C6-C30)arylcarbonyl group; a di(C6-C30)arylboronyl group; a di(C1-C30)alkylboronyl group; a (C1-C30)alkyl(C6-C30)arylboronyl group; a (C6-C30)aryl(C1-C30)alkyl group; and a (C1-C30)alkyl(C6-C30)aryl group.

10. The compound according to claim 2, wherein the compound represented by formula 2 or 5: is selected from the group consisting of the following compounds:

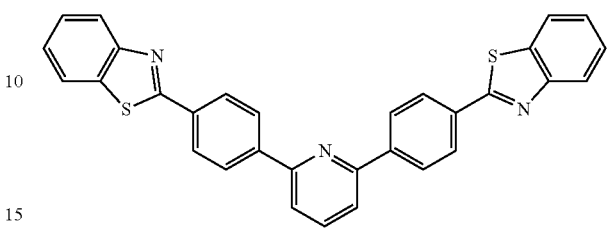

B-1

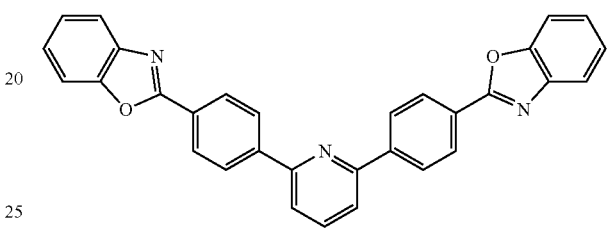

B-2

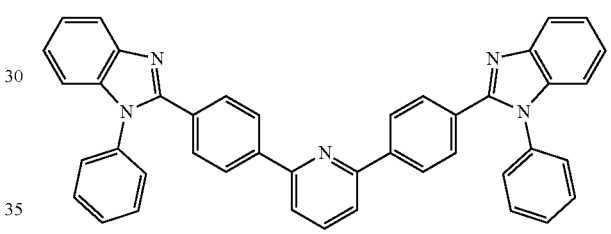

B-3

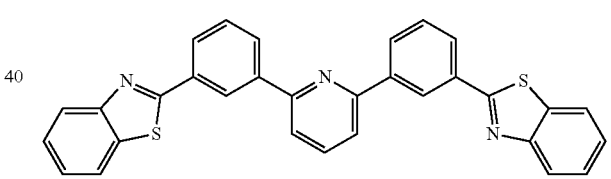

B-4

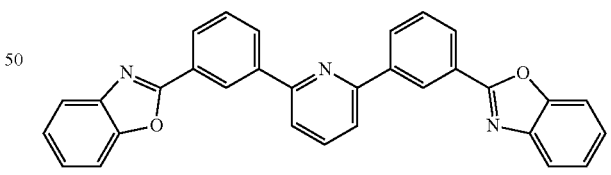

B-5

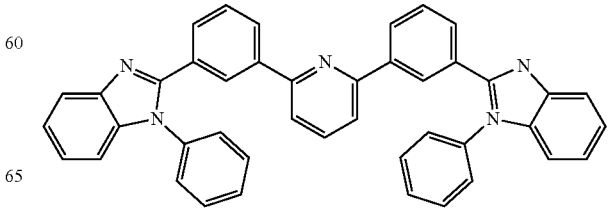

B-6

-continued
B-7
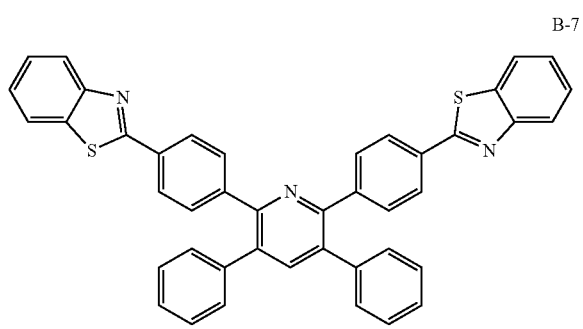
B-8
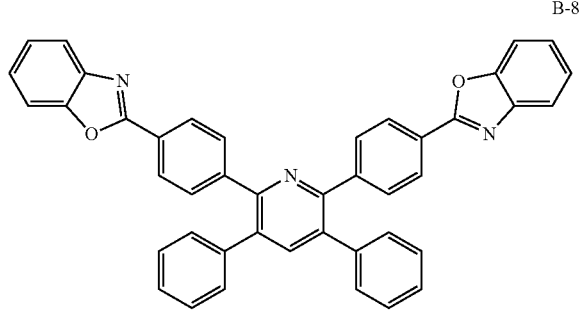
B-9
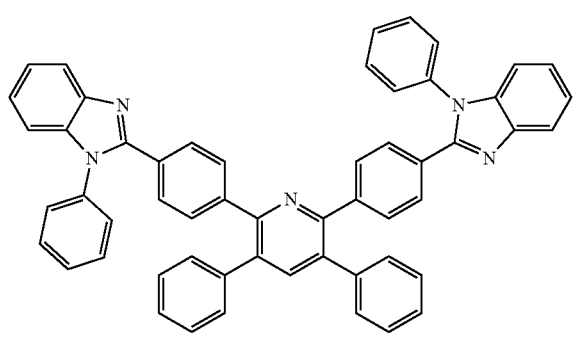
B-10
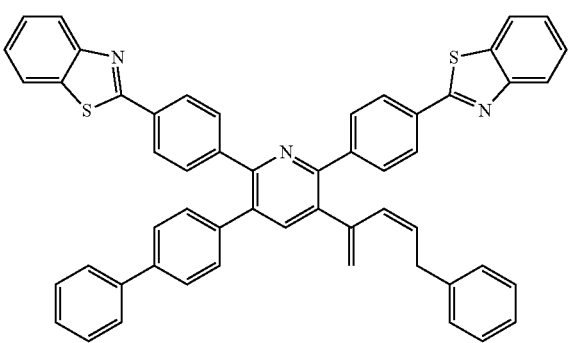
-continued
B-11
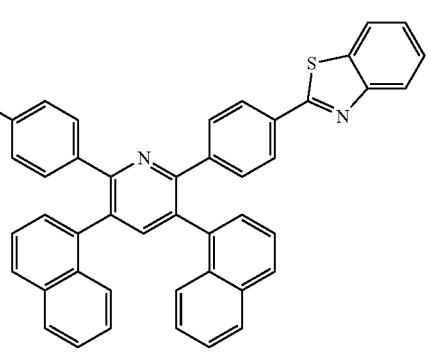
B-12
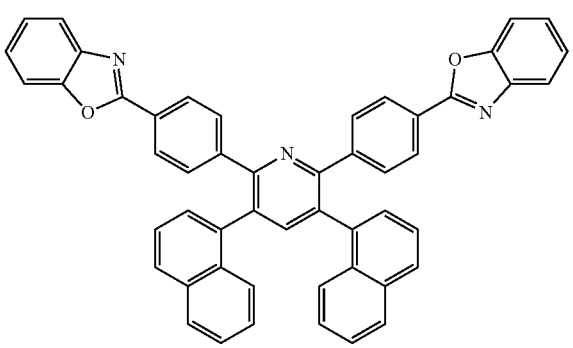
B-13
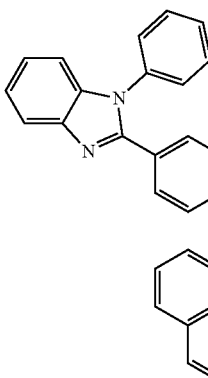
B-14
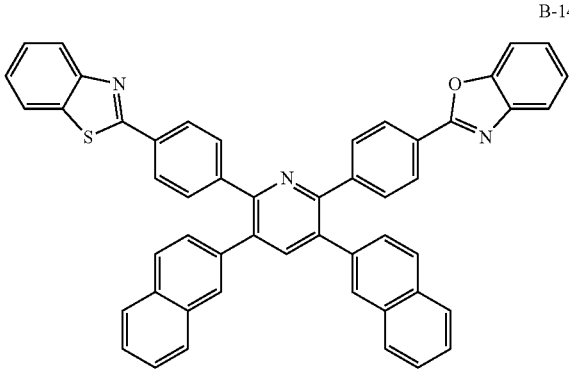

-continued
B-15
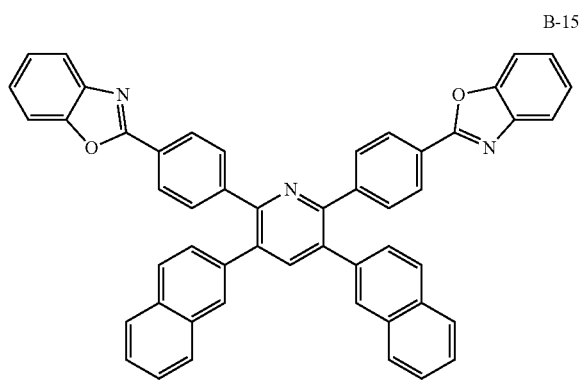
B-16
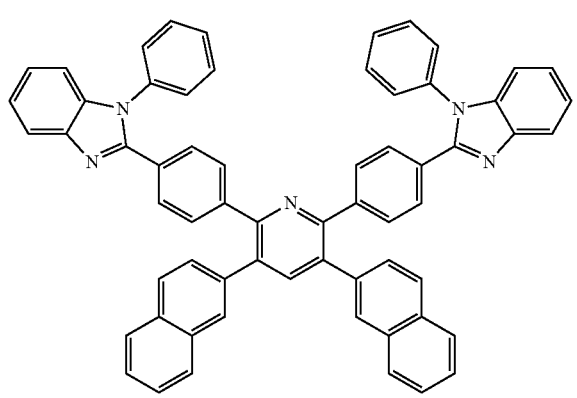
B-17
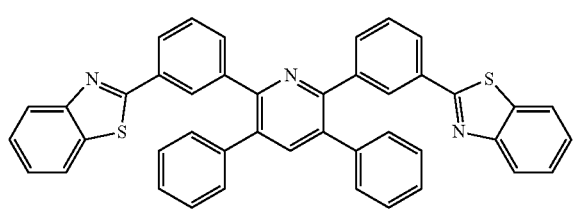
B-18
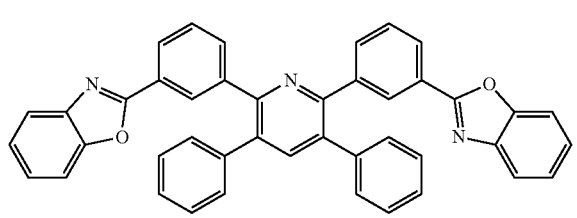
B-19
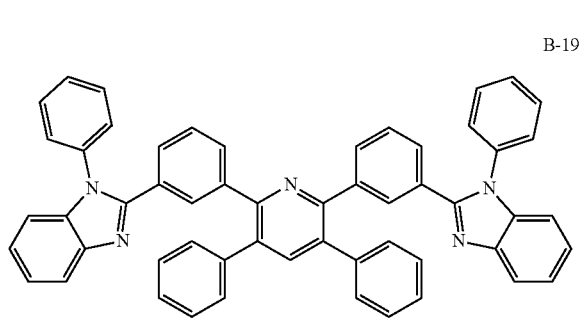
-continued
B-20
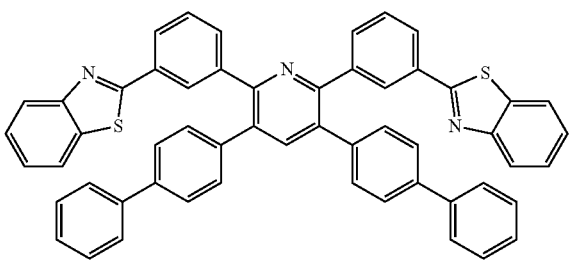
B-21
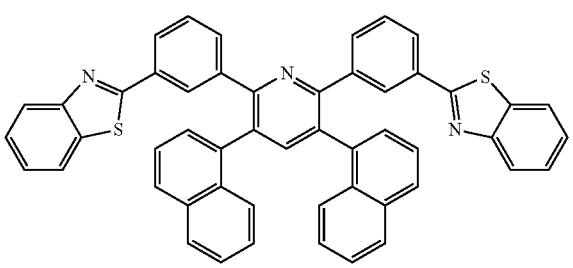
B-22
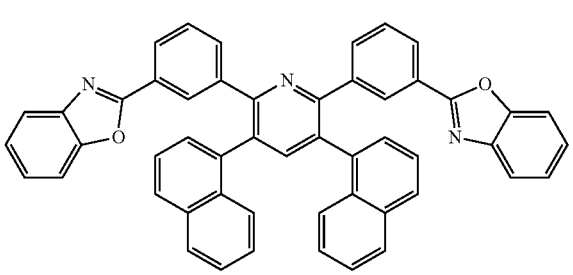
B-23
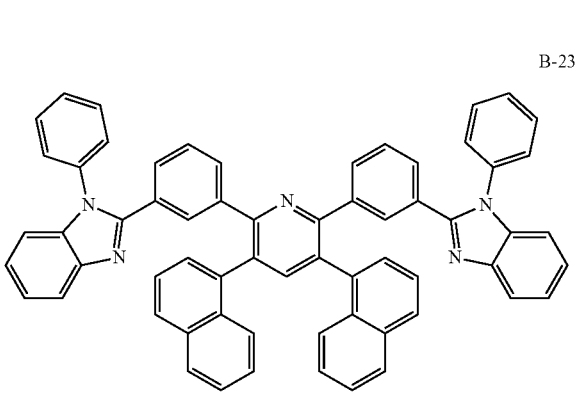
B-24
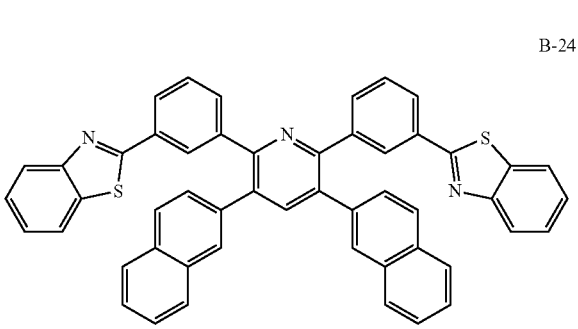

-continued
B-25
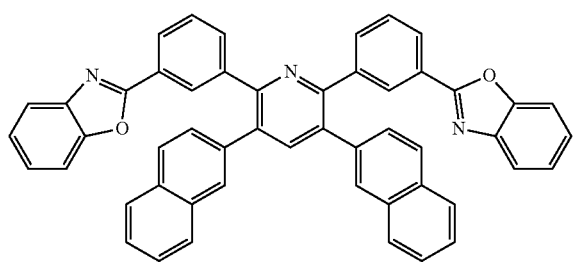
B-26
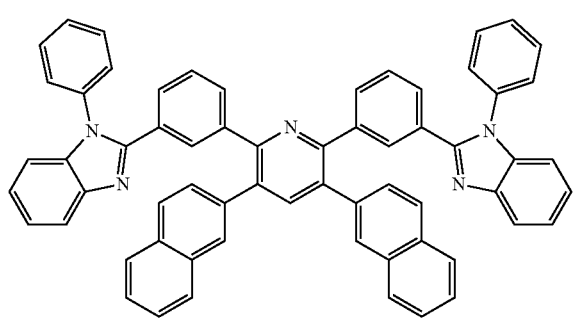
B-27
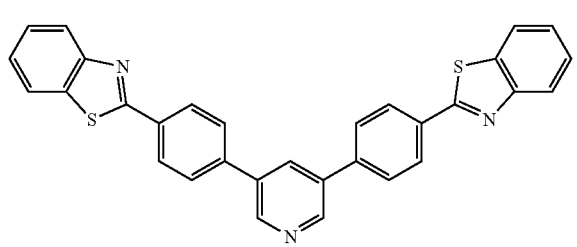
B-28
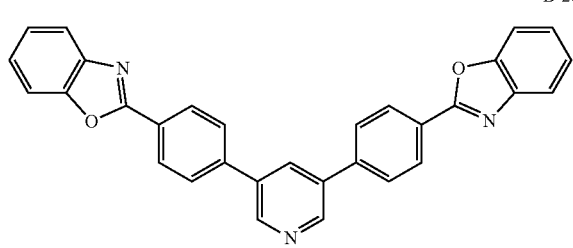
B-29
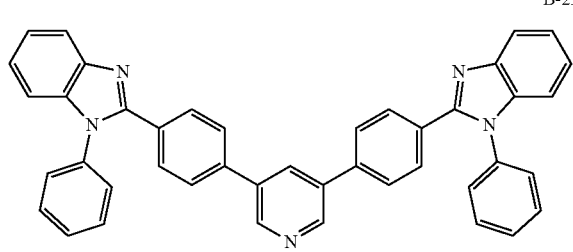
B-30
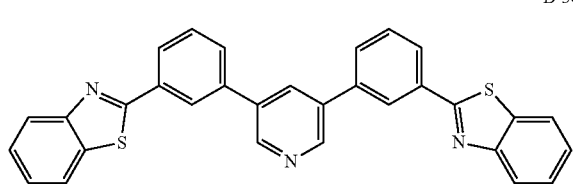
-continued
B-31
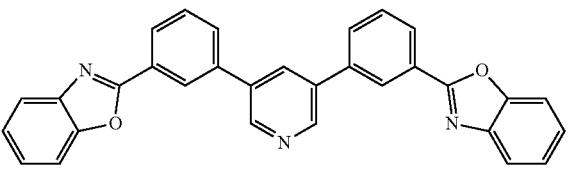 [SMILES: c1cc(-c2cncc(-c3cccc(-c4nc5ccccc5s4)c3)c2)cc(-c2nc3ccccc3s2)c1]
B-32
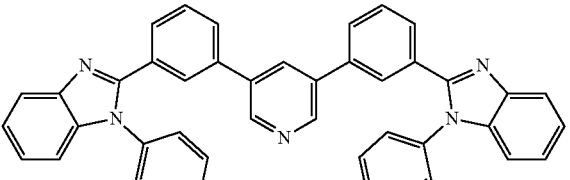
B-33
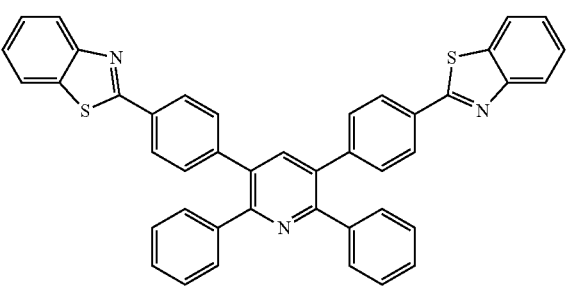
B-34
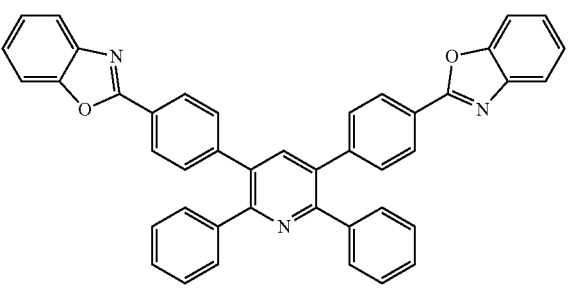
B-35
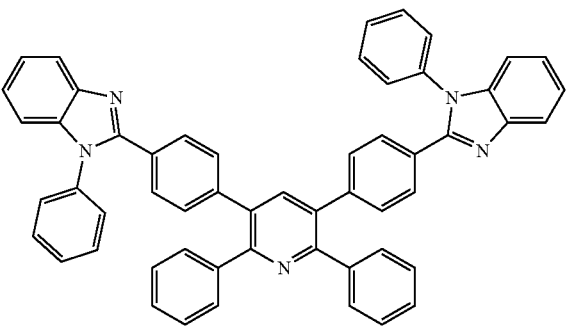

-continued
B-36
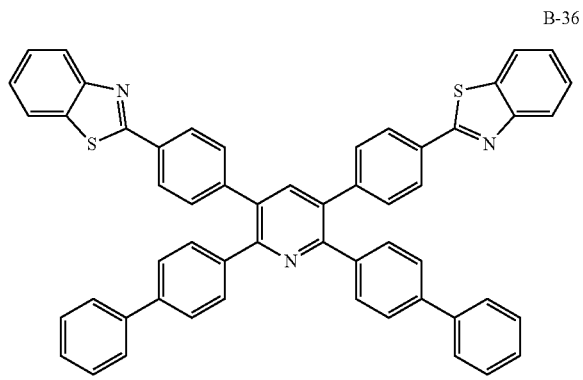
B-40
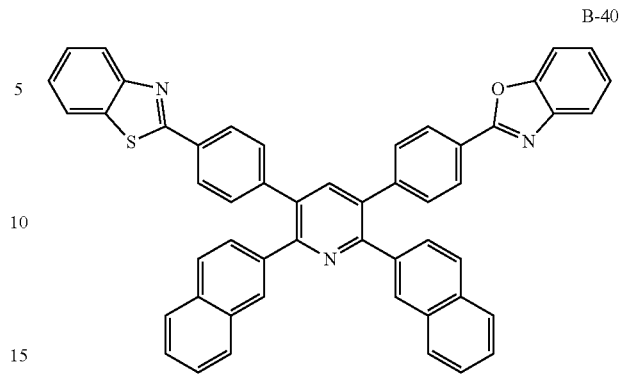
B-37
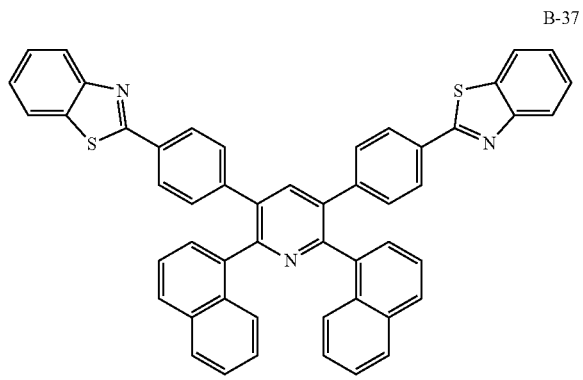
B-41
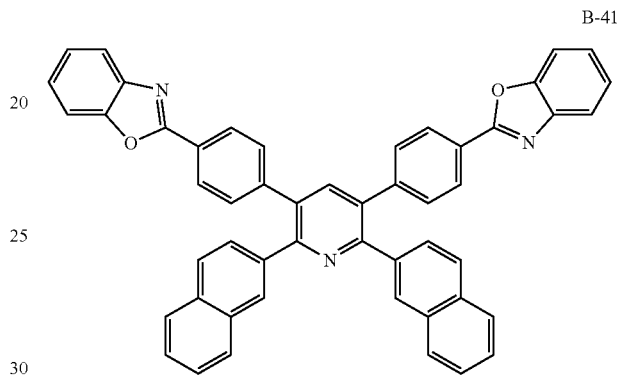
B-38
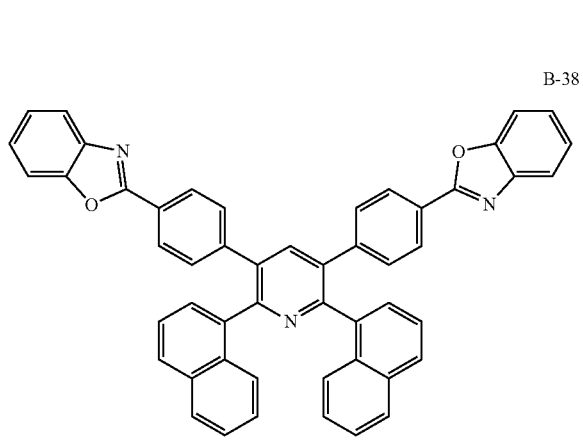
B-42
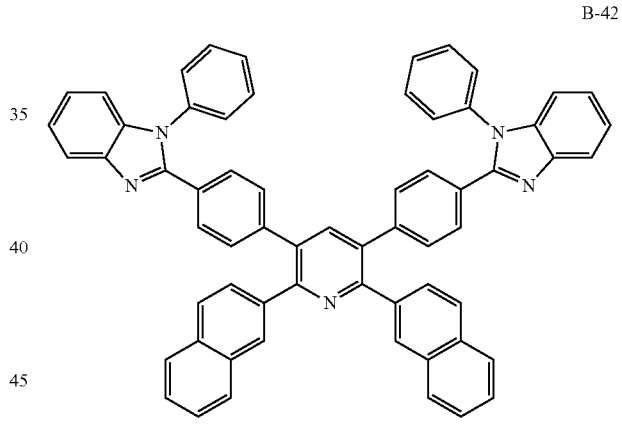
B-39
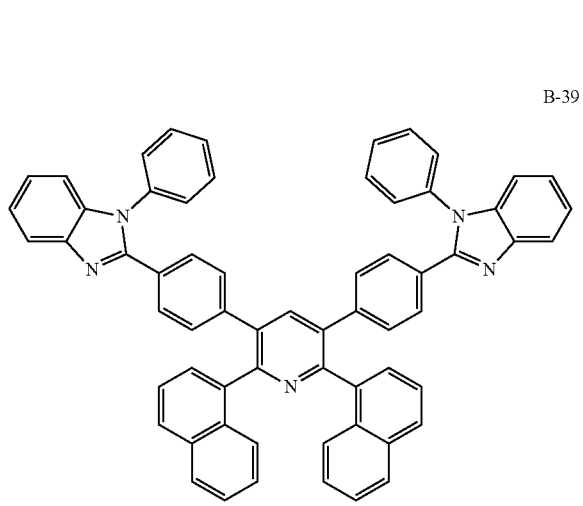
B-43
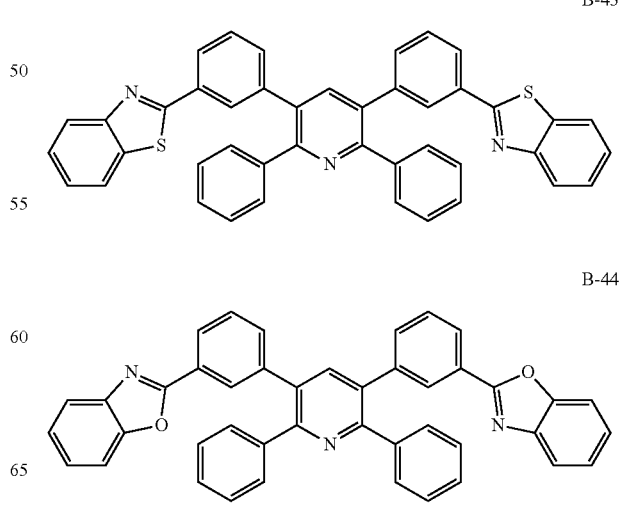
B-44

-continued
B-45
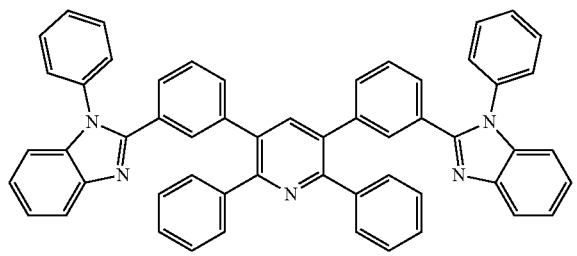
B-46
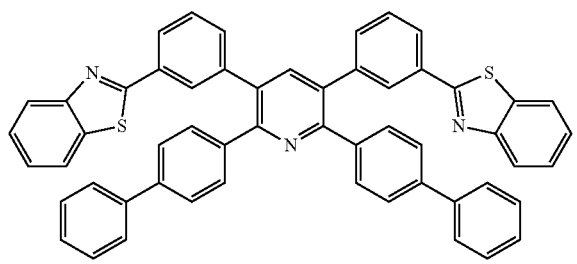
B-47
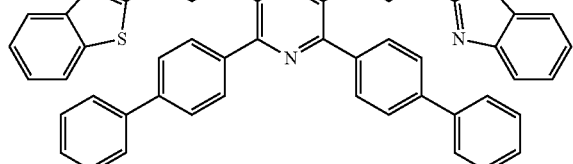
B-48
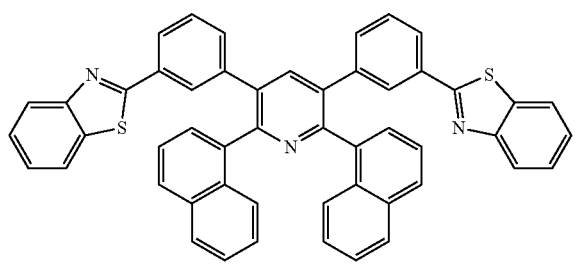
B-49
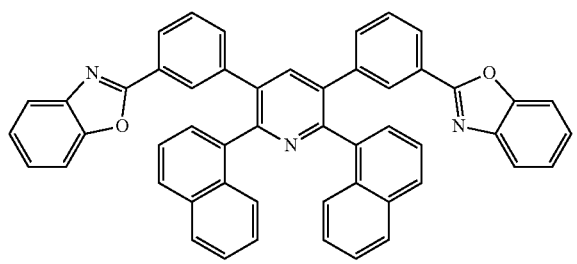
-continued
B-50
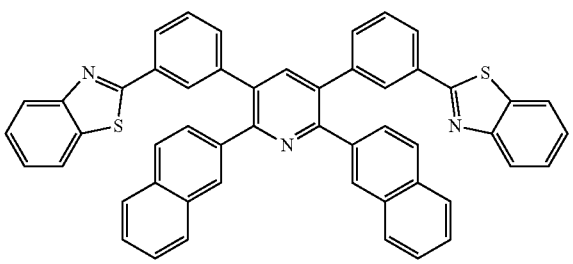
B-51
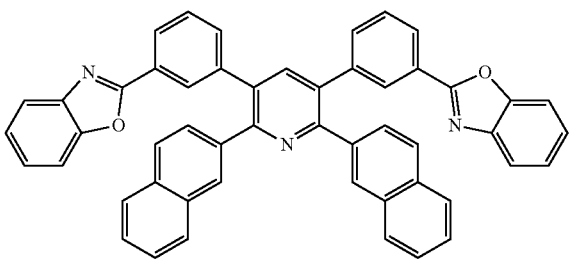
B-52
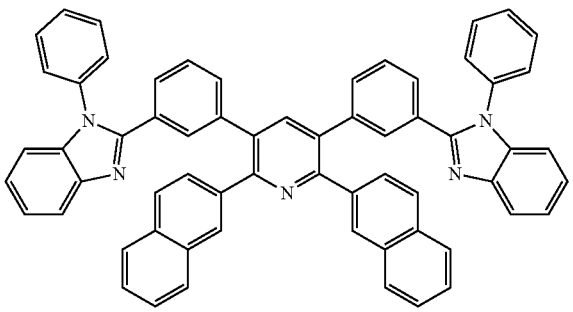
B-84
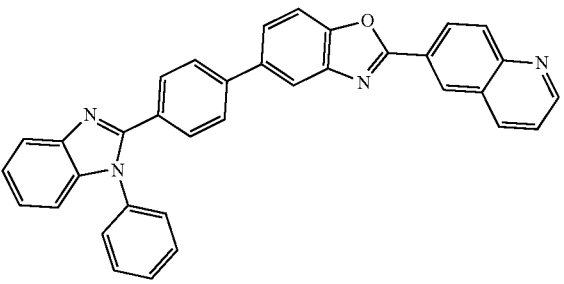
B-85
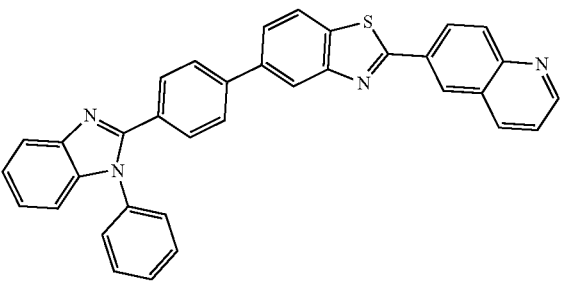

B-86
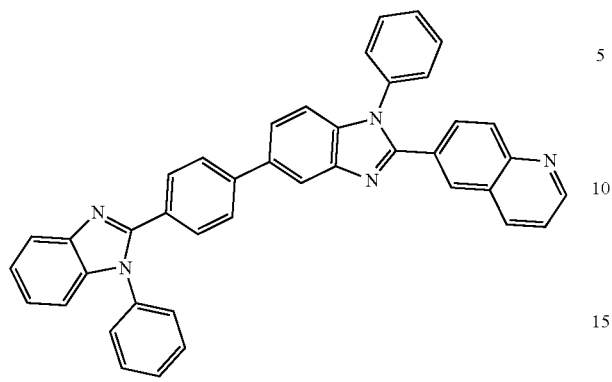
B-87
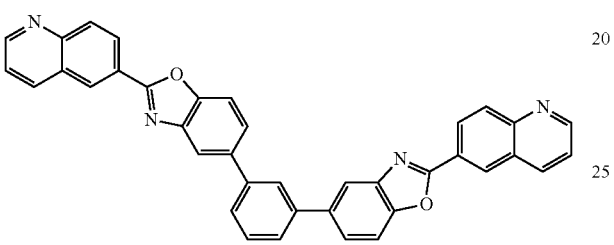
B-88
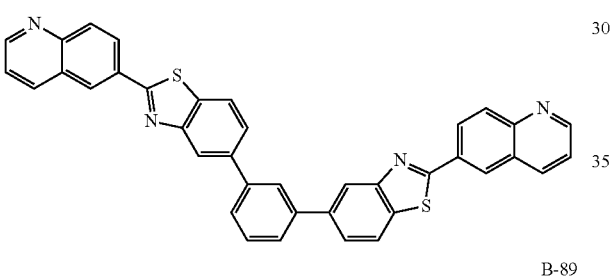
B-89
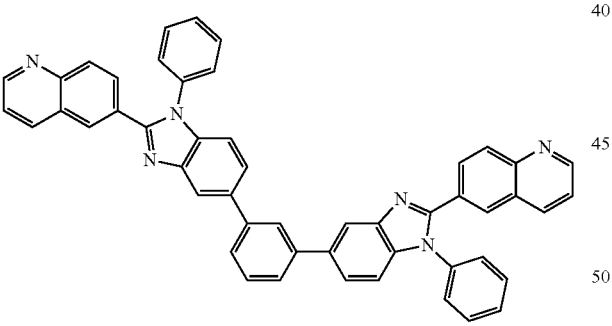
B-92
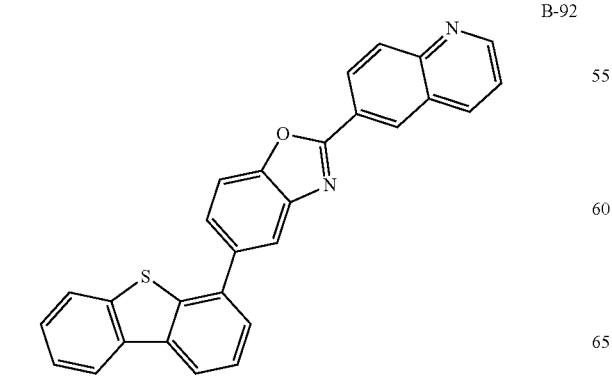
B-93
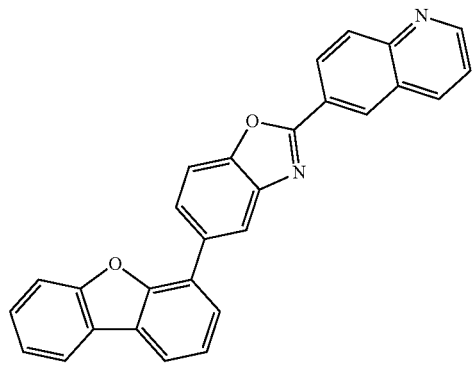
B-94
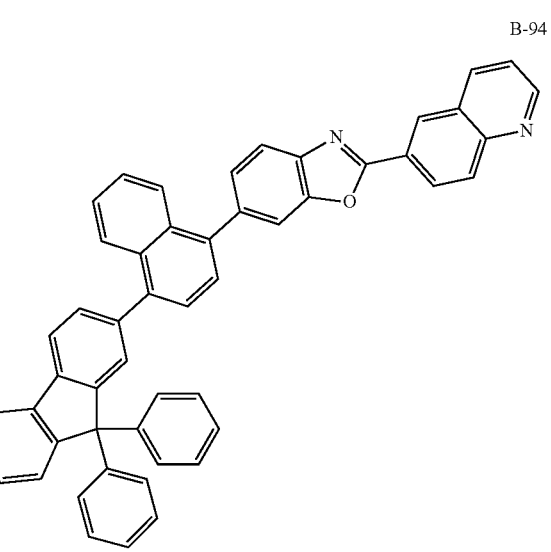
B-95
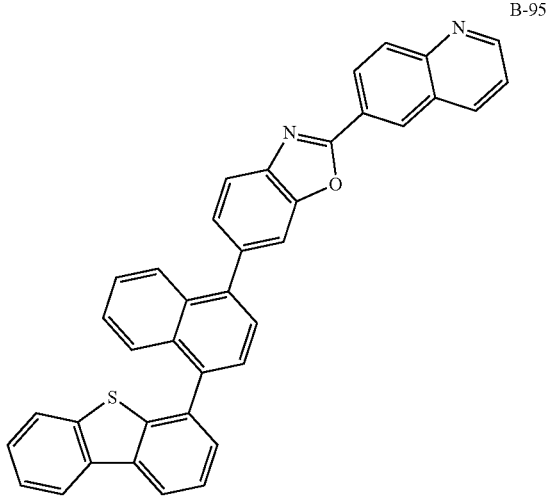

B-96
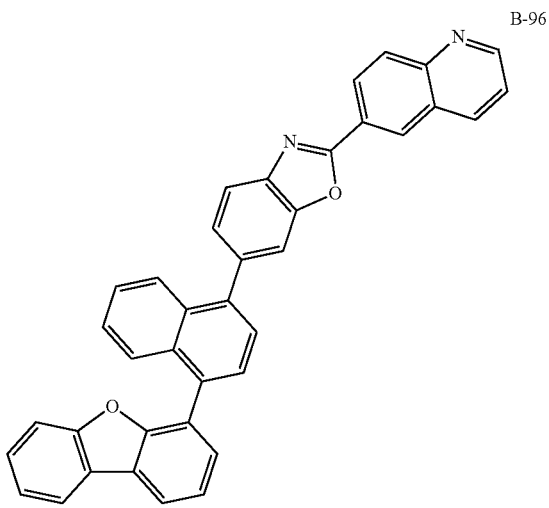
B-97
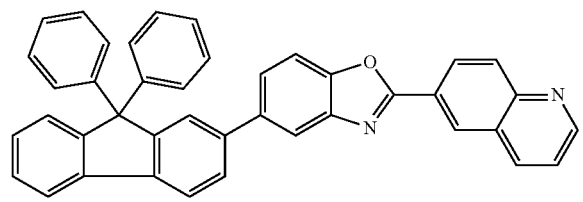
B-98
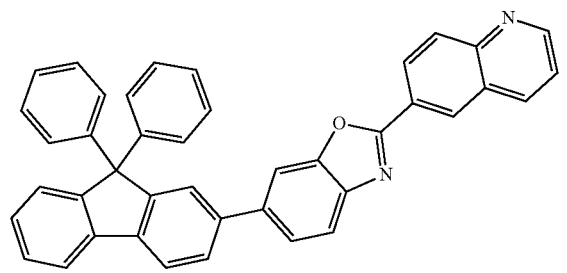
B-99
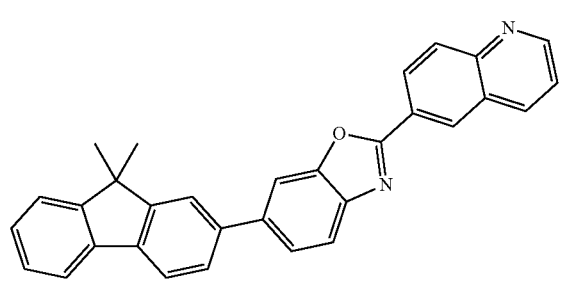
B-100
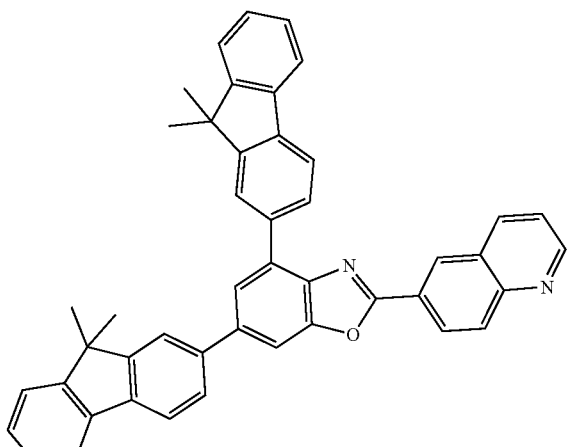
B-101
B-102
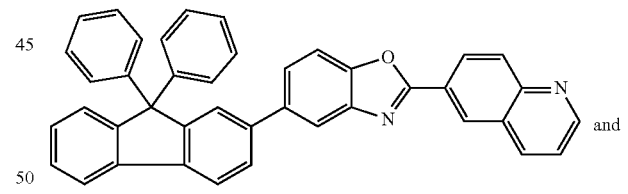
B-103
and
B-104
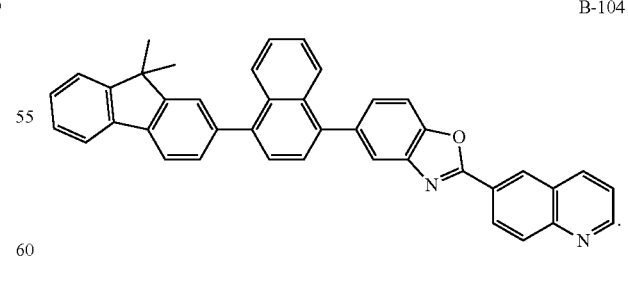
* * * * *

UNITED STATES PATENT AND TRADEMARK OFFICE
CERTIFICATE OF CORRECTION

PATENT NO. : 11,316,114 B2  
APPLICATION NO. : 16/077765  
DATED : April 26, 2022  
INVENTOR(S) : Sang Hee Cho et al.

Page 1 of 1

It is certified that error appears in the above-identified patent and that said Letters Patent is hereby corrected as shown below:

In the Claims

In Claim 10, organic electroluminescent compound, B-10, at Column 119, Line 61:

" 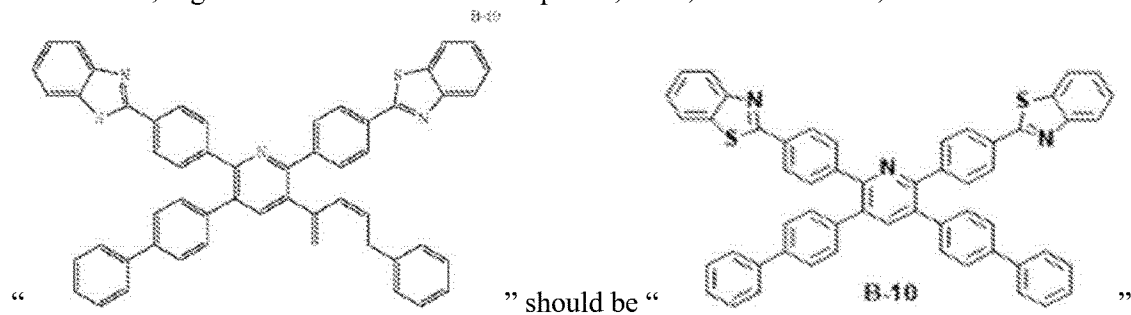 " should be " 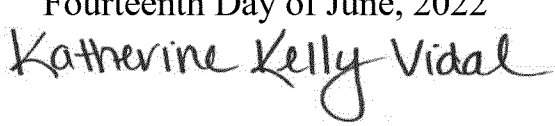 "

Signed and Sealed this  
Fourteenth Day of June, 2022

Katherine Kelly Vidal  
*Director of the United States Patent and Trademark Office*